(12) United States Patent
Yusibov et al.

(10) Patent No.: US 9,115,201 B2
(45) Date of Patent: Aug. 25, 2015

(54) HUMANIZED NEURAMINIDASE ANTIBODY AND METHODS OF USE THEREOF

(71) Applicant: iBio Inc., Newark, DE (US)

(72) Inventors: Vidadi Yusibov, Havertown, PA (US); Vadim Mett, Elma, NY (US); Yoko Shoji, Wilmington, DE (US)

(73) Assignee: iBio Inc., Newark, DE (US)

( * ) Notice: Subject to any disclaimer, the term of this patent is extended or adjusted under 35 U.S.C. 154(b) by 0 days.

(21) Appl. No.: 14/254,176

(22) Filed: Apr. 16, 2014

(65) Prior Publication Data

US 2014/0314754 A1    Oct. 23, 2014

Related U.S. Application Data

(62) Division of application No. 13/121,235, filed as application No. PCT/US2009/058640 on Sep. 28, 2009, now Pat. No. 8,734,803.

(60) Provisional application No. 61/100,740, filed on Sep. 28, 2008.

(51) Int. Cl.
| | |
|---|---|
| *A61K 39/42* | (2006.01) |
| *A61K 39/00* | (2006.01) |
| *C07K 16/40* | (2006.01) |
| *C07K 16/10* | (2006.01) |

(52) U.S. Cl.
CPC ............. *C07K 16/40* (2013.01); *C07K 16/1018* (2013.01); *A61K 2039/505* (2013.01); *C07K 2317/24* (2013.01); *C07K 2317/41* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,196,265 | A | 4/1980 | Koprowski et al. |
| 4,270,537 | A | 6/1981 | Romaine |
| 4,596,556 | A | 6/1986 | Morrow et al. |
| 4,653,728 | A | 3/1987 | Mochizuki et al. |
| 4,790,824 | A | 12/1988 | Morrow et al. |
| 4,816,567 | A | 3/1989 | Cabilly et al. |
| 4,886,499 | A | 12/1989 | Cirelli et al. |
| 4,935,496 | A | 6/1990 | Kudo et al. |
| 4,940,460 | A | 7/1990 | Casey et al. |
| 4,941,880 | A | 7/1990 | Burns |
| 5,015,235 | A | 5/1991 | Crossman |
| 5,064,413 | A | 11/1991 | McKinnon et al. |
| 5,141,496 | A | 8/1992 | Dalto et al. |
| 5,190,521 | A | 3/1993 | Hubbard et al. |

(Continued)

FOREIGN PATENT DOCUMENTS

| | | |
|---|---|---|
| CZ | 20 031 859 | 2/2005 |
| EP | 404097 | 6/1990 |

(Continued)

OTHER PUBLICATIONS

Accession CAA4959, Apr. 18, 2005.

(Continued)

*Primary Examiner* — Zachariah Lucas
*Assistant Examiner* — M. Franco Salvoza
(74) *Attorney, Agent, or Firm* — Fish & Richardson P.C.

(57) ABSTRACT

Antibodies against influenza neuraminidase, compositions containing the antibodies, and methods of using the antibodies are provided herein.

Figure 1:
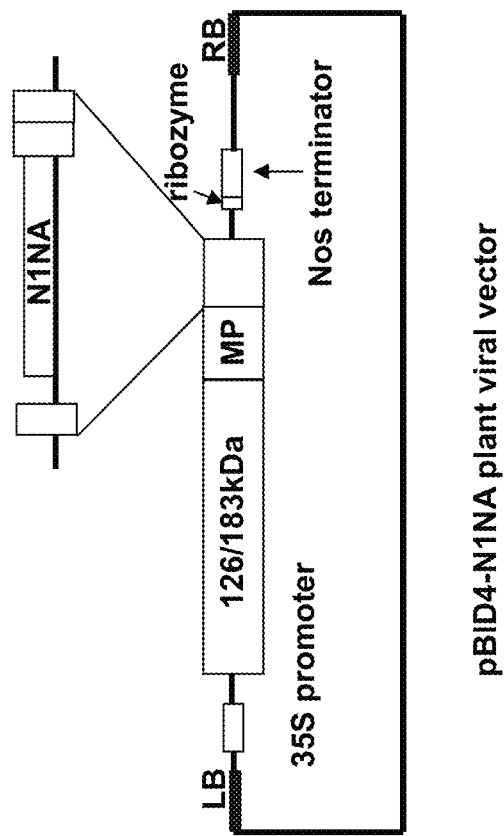

4 Claims, 7 Drawing Sheets pBID4-N1NA plant viral vector

(56) References Cited

U.S. PATENT DOCUMENTS

| | | |
|---|---|---|
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brenneman |
| 5,480,381 A | 1/1996 | Weston |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,569,825 A | 10/1996 | Lonberg et al. |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,625,126 A | 4/1997 | Lonberg et al. |
| 5,633,425 A | 5/1997 | Lonberg et al. |
| 5,639,641 A | 6/1997 | Pedersen et al. |
| 5,649,912 A | 7/1997 | Peterson |
| 5,658,727 A | 8/1997 | Barbas et al. |
| 5,661,016 A | 8/1997 | Lonberg et al. |
| 5,667,988 A | 9/1997 | Barbas et al. |
| 5,681,722 A | 10/1997 | Newman et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,698,426 A | 12/1997 | Huse |
| 5,702,892 A | 12/1997 | Mulligan-Kehoe |
| 5,704,911 A | 1/1998 | Parsons |
| 5,705,154 A | 1/1998 | Dalie et al. |
| 5,733,743 A | 3/1998 | Johnson et al. |
| 5,750,078 A | 5/1998 | Shitara et al. |
| 5,759,817 A | 6/1998 | Barbas |
| 5,770,403 A | 6/1998 | Dalie et al. |
| 5,770,429 A | 6/1998 | Lonberg et al. |
| 5,855,866 A | 1/1999 | Thorpe et al. |
| 5,877,289 A | 3/1999 | Thorpe et al. |
| 5,888,789 A | 3/1999 | Rodriguez |
| 5,893,397 A | 4/1999 | Peterson et al. |
| 5,965,132 A | 10/1999 | Thorpe et al. |
| 5,993,412 A | 11/1999 | Deily et al. |
| 6,004,555 A | 12/1999 | Thorpe et al. |
| 6,042,832 A | 3/2000 | Koprowski et al. |
| 6,093,399 A | 7/2000 | Thorpe et al. |
| 6,103,511 A | 8/2000 | Li et al. |
| 6,261,535 B1 | 7/2001 | Thorpe et al. |
| 6,524,825 B1 | 2/2003 | Mizzen et al. |
| 6,649,172 B2 | 11/2003 | Johnson |
| 6,734,173 B1 | 5/2004 | Wu et al. |
| 6,740,740 B2 | 5/2004 | Garger et al. |
| 6,797,491 B2 | 9/2004 | Neefe, Jr. et al. |
| 6,841,659 B2 | 1/2005 | Turpen et al. |
| 7,888,135 B2 | 2/2011 | Tarleton et al. |
| 8,058,511 B2 | 11/2011 | Fedorkin et al. |
| 8,124,103 B2 | 2/2012 | Yusibov et al. |
| 8,173,408 B2 | 5/2012 | Yusibov et al. |
| 8,277,816 B2 | 10/2012 | Yusibov et al. |
| 8,404,252 B2 | 3/2013 | Yusibov et al. |
| 8,591,909 B2 | 11/2013 | Yusibov et al. |
| 8,597,942 B2 | 12/2013 | Fedorkin et al. |
| 8,734,803 B2 | 5/2014 | Yusibov et al. |
| 8,778,348 B2 | 7/2014 | Knapp et al. |
| 8,784,819 B2 | 7/2014 | Yusibov et al. |
| 2004/0093643 A1 | 5/2004 | Ensley |
| 2004/0170606 A1 | 9/2004 | Palmer et al. |
| 2004/0268442 A1 | 12/2004 | Miller et al. |
| 2005/0026291 A1 | 2/2005 | Fedorkin et al. |
| 2005/0042229 A1 | 2/2005 | Yang et al. |
| 2005/0048074 A1 | 3/2005 | Cardineau et al. |
| 2005/0054820 A1 | 3/2005 | Wu et al. |
| 2005/0114920 A1 | 5/2005 | Yusibov et al. |
| 2005/0186621 A1 | 8/2005 | Galarza et al. |
| 2006/0008473 A1 | 1/2006 | Yang et al. |
| 2006/0265787 A1 | 11/2006 | Piruzian et al. |
| 2007/0275014 A1 | 11/2007 | Yusibov et al. |
| 2008/0124272 A1 | 5/2008 | Yusibov et al. |
| 2008/0279877 A1 | 11/2008 | Yusibov et al. |
| 2009/0324634 A1 | 12/2009 | Knapp et al. |
| 2010/0227373 A1 | 9/2010 | Yusibov et al. |
| 2010/0239594 A1 | 9/2010 | Yusibov et al. |
| 2011/0027304 A1 | 2/2011 | Yusibov et al. |
| 2011/0059130 A1 | 3/2011 | Yusibov |
| 2011/0070609 A1 | 3/2011 | Yusibov et al. |
| 2011/0142870 A1 | 6/2011 | Yusibov |
| 2011/0314575 A1 | 12/2011 | Yusibov et al. |
| 2012/0034253 A1 | 2/2012 | Yusibov et al. |
| 2012/0282288 A1 | 11/2012 | Yusibov et al. |
| 2013/0149327 A1 | 6/2013 | Yusibov et al. |
| 2014/0141508 A1 | 5/2014 | Yusibov et al. |

FOREIGN PATENT DOCUMENTS

| | | |
|---|---|---|
| WO | WO 9311161 | 6/1993 |
| WO | WO 9602555 | 2/1996 |
| WO | WO 9612028 | 4/1996 |
| WO | WO 9713537 | 4/1997 |
| WO | WO 9737705 | 10/1997 |
| WO | WO 9814595 | 4/1998 |
| WO | WO 9845331 | 10/1998 |
| WO | WO 9907860 | 2/1999 |
| WO | WO 0020612 | 4/2000 |
| WO | WO 0025574 | 5/2000 |
| WO | WO 0046350 | 8/2000 |
| WO | WO 0200892 | 1/2002 |
| WO | WO 03040179 | 5/2003 |
| WO | WO 03057834 | 7/2003 |
| WO | WO 03076568 | 9/2003 |
| WO | WO 2004043886 | 5/2004 |
| WO | WO 2004058797 | 7/2004 |
| WO | WO 2005023177 | 3/2005 |
| WO | WO 2005026375 | 3/2005 |
| WO | WO 2005049839 | 6/2005 |
| WO | WO 2005056052 | 6/2005 |
| WO | WO 2005067620 | 7/2005 |
| WO | WO 2005081905 | 9/2005 |
| WO | WO 2005120567 | 12/2005 |
| WO | WO 2006003018 | 1/2006 |
| WO | WO 2006124712 | 11/2006 |
| WO | WO 2007089753 | 8/2007 |
| WO | WO 2007095304 | 8/2007 |
| WO | WO 2007095318 | 8/2007 |
| WO | WO 2007149715 | 12/2007 |
| WO | WO 2008021959 | 2/2008 |
| WO | WO 2008033105 | 3/2008 |
| WO | WO 2008033159 | 3/2008 |
| WO | WO 2008048945 | 4/2008 |
| WO | WO 2008110937 | 9/2008 |
| WO | WO 2008134643 | 11/2008 |
| WO | WO 2009009759 | 1/2009 |
| WO | WO 2009026397 | 2/2009 |
| WO | WO 2009054708 | 4/2009 |
| WO | WO 2009058355 | 5/2009 |
| WO | WO 2010036970 | 4/2010 |
| WO | WO 2010037046 | 4/2010 |

OTHER PUBLICATIONS

Ahlquist et al., "Gene Expression Vectors Derived from Plant RNA Viruses," Current Communications in Molecular Biology—Viral Vectors, (Ed., Gluzman et al.) 183-189, 1988.

(56) References Cited

OTHER PUBLICATIONS

Air GM, "Mechanism of antigenic variation in an individual epitope on influenza virus N9 neuraminidase," J. Virology, 64(12):5797-5803, 1990.
Akol and Murray, "*Trypanosoma congolense*: Susceptibility of cattle to cyclical challenge," Exp. Parasitol., 55:386-393, 1983.
Alignment of 11706573-6 to SEQ ID No. 6.
Alignment of 11706573-30 to SEQ ID No. 6.
Alignment of 11706576-12 to SEQ ID No. 6.
Alignment of 12110877-30 to SEQ ID No. 6.
Alvarez et al., "Plant-made subunit vaccine against pneumonic and bubonic plague is orally immunogenic in mice," Vaccine, 24(14):2477-2490, 2006.
Anderson et al., Infect. Immun., 64:4580-5, 1996.
Andrews et al., Infect. Immun., 64:2180-7, 1996.
Ay et al., "Crystal structures and properties of de novo circularly permuted 1,3-1,4-beta-glucanases," Proteins, 30(2):155-67, 1998.
Aymard et al., "Role of antineuraminidase antibodies in protection against influenza," Bulletin de l'Academie nationale de medicine, 182(8): 1723-1736 (1998).
Aymard et al., "Neuraminidase assays," *Developments in Biologicals*, 115:75-83 (2003).
Barbas et al., *Proc. Natl. Acad. Sci. USA* 88:7978, 1991.
Barbas et al., *Proc. Natl. Acad. Sci. USA* 89:4457, 1992.
Barfield et al., "Gene transfer in plants of *Brassica juncea* using *Agrobacterium tumefaciens* mediated transformation," *Plant Cell Reports* 1991, 10(6/7): 308-14.
Bates, "Genetic transformation of plants by protoplast electroporation," *Molecular Biotechnol.*, 1994, 2(2):135-145.
Beachy et al., "A genetic map for the cowpea strain of TMV" *Virology* 1976, 73: 498-507.
Berger M, et al., "Therapeutic applications of monoclonal antibodies" Am J Med Sci, Jul. 2002;324(1):14-30.
Bedell et al., "The E6-E7 Region of Human Papillomavirus Type 18 Is Sufficient for Transformation of NIH 3T3 and Rat-1 Cells," *J. Virol.*, 1987, 61:3635-40.
Bisaro et al., "Genetic Analysis of Tomato Golden Mosaic Virus," Current Communications in Molecular Biology: Viral Vectors, Cold Spring Harbor Laboratory, Cold Spring Harbor, NY, pp. 172-189, 1988.
Bol et al., "A Functional Equivalence of Top Component a RNA and Coat Protein in the Initiation of Infection by Alfalfa Mosaic Virus," *Virology*, 46:73-85, 1971.
Bol et al., "Alfalfa Mosaic Virus and Ilarviruses: Involvement of Coat Protein in Multiple Steps of the Replication Cycle" *J. Gen. Virol.* 1999, 80: 1089-1102.
Boyd, M. R. and Beeson, M. F., "Animal models for evaluation of compounds against influenza viruses," Journal of Antimicrobial Chemotherapy, (1975) 1 (Suppl.), 43-47.
Brett et al., "Immunization against influenza A virus: comparison of conventional inactivated, live-attenuated and recombinant baculovirus produced purified hemagglutinin and neuraminidase vaccines in a murine model system," *Virology*, vol. 339, No. 2, 273-280 (2005).
Brodzik et al., "Advances in alfalfa mosaic virus-mediated expression of anthrax antigen in planta," Biochem. Biophys. Res. Commun., Dec. 16, 2005, vol. 338, No. 2, pp. 717-722.
Broothaerts et al. (2005), Nature, 433:629-33.
Bruening et al., "In Vitro and In Vivo Translation of the Ribonucleic Acids of a Cowpea Strain of Tobacco Mosaic Virus" *Virology* 1976, 71: 498-517.
Burke et al. (1987) Science 236:806.
Buscaglia et al., "Tandem amino acid repeats from *Trypanosoma cruzi* shed antigens increase the half-life of proteins in blood," *Blood*, vol. 93(6), pp. 2025-2032, Mar. 15, 1999.
Calandrelli et al., "Purification and characterization of thermostable xylanase and beta-xylosidase by the thermophilic bacterium *Bacillus thermantarcticus*," Res. Microbiol., 155(4): 283-9, 2004.
Canizares et al., "Use of viral vectors for vaccine production in plants," *Immunol. Cell Biol*., 2005, 83:263-270.
Chain et al., J. Bacteriol. 188:4453-63, 2006.
Chen et al., "Complete sequence of the binary vector pB1121 and its application in cloning T-DNA insertion from transgenic plants," Mol. Breed., 2003, 11, 287-293.
Chen et al., "Induction and relief of nasal congestion in ferrets infected with influenza virus," *Int. J. Exp. Path*., (1995), 76, pp. 55-64.
Chica et al., "Semi-rational approaches to engineering enzyme activity: combining the benefits of directed evolution and rational design," Current Opinion in Biotechnology, 16:378-384, 2005.
Chichester et al., "Immunogenicity of a subunit vaccine against *Bacillus anthracis*," Vaccine, 2007, 25:3111-3114.
Chichester et al., Different response requirements for IFNγ production in ELISPOT assays by CD4+ T cells from mice early and late after submission (2006), J. Immunol Methods, 309:99-107.
Corbel, M. J., "Reasons for instability of bacterial vaccines," *Developments in Biological Standardization*, vol. 87, pp. 113-124, 1996.
Costa et al., "Conformational stability and antibody response to the 18kDa heat-shock protein formulated into different vehicles," *Applied Biochemistry and Biotechnology*, vol. 73(1), pp. 19-28, Apr. 1998.
Crossway, A., et al., "Integration of foreign DNA following microinjection of tobacco mesophyll protoplasts," *Mol. Gen. Genet*., 1986, 202:179-185.
Curtis and Nam, "Transgenic radish (*Raphanus sativus* L. longipinnatus Bailey) by floral-dip method—plant development and surfactant are important in optimizing transformation efficiency," *Transgenic Research*, 2001, 10(4):363-371.
Davies et al., "Affinity improvement of single antibody VH domains: residues in all three hypervariable regions affect antigen binding," Immunotechnology, 2(3):169-179, 1996.
Dawson et al., "cDNA cloning of the complete genome of tobacco mosaic virus and production of infectious transcripts," Proc. Natl. Acad. Sci., USA, 1986, 83:1832.
DeGraff, et al., "In Vitro Evidence That the Coat Protein of Alfalfa Mosaic Virus Plays a Direct Role in the Regulation of Plus and Minus RNA Synthesis Implications for the Life Cycle of Alfalfa Mosaic Virus" *Virology* 1995, 208: 583-589.
de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20(29-30):3456-3464, 2002.
Deng et al., 2002, J. Bacteriol., 1984:4601-11.
Desfeux et al., "Female Reproductive Tissues Are the Primary Target of *Agrobacterium*-Mediated Transformation by the *Arabidopsis* Floral-Dip Method," Plant Physiology, 2000, 123(3):895-904.
Dréau et al., "Human Papilloma Virus in Melanoma Biopsy Specimens and Its Relation to Melanoma Progression," Annals of Surgery, 2000, 231:664-671.
Fenton et al., "Immunity to Influenza in Ferrets. XIV: Comparative Immunity Following Infection or Immunization With Live or Inactivated Vaccine," *Br. J. exp. Path*., (1981) 62, 297.
Fernando et al., "Expression, purification and immunological characterization of the transforming protein E7, from cervical cancer-associated human papillomavirus type 16," *Clin Exp Immunol*, 1999, 115:397-403.
Flick-Smith et al., "A Recombinant Carboxy-Terminal Domain of the Protective Antigen of *Bacillus anthracis* Protects Mice against Anthrax Infection," Infect. Immun., 2002, 70:1653-1656.
Floss, D. M. et al., "Production of vaccines and therapeutic antibodies for veterinary applications in transgenic plants: an overview," Transgenic Research, vol. 16, No. 3, Jun. 2007, pp. 315-332.
Fraley et al., "Liposome-Mediated Delivery of Tobacco Mosaic Virus RNA Into Tobacco Protoplasts: A Sensitive Assay for Monitoring Liposome-Protoplast Interactions" *Proc. Natl. Acad. Sci. USA* 1982, 79: 1859-1863.
Fraley et al., "Expression of Bacterial Genes in Plant Cells" *Proc. Natl. Acad. Sci. USA* 1983, 80: 4803-4807.
Franconi et al., "Plant-derived Human Papillomavirus 16 E7 Oncoprotein Induces Immune Response and Specific Tumor Production," *Cancer Res*., 2002, 62:3654.

(56) References Cited

OTHER PUBLICATIONS

Fromm et al., "Expression of Genes Transferred Into Monocot and Dicot Plant Cells by Electroporation" Proc. Natl. Acad. Sci. USA 1985, 82: 5824, 1985.
Fütterer et al., "Use of DNA Plant Viruses and Plant Viral Expression Signals for Gene Expression in Plants and Plant Protoplasts," Current Communications in Molecular Biology—Viral Vectors, (Ed., Gluzman et al.) 1988, 178-182.
Gelvin, "*Agrobacterium*-Mediated Plant Transformation: the Biology behind the 'Gene-Jockeying' Tool," Microbiol. Mol Biol. Rev., 2003, 67(1):16-37.
Gin and Narasu, "Transgenic hairy roots: recent trends and applications," Biotechnol. Adv., 2000, 18:1-22.
Gleba et al., "Magnifection—a new platform for expressing recombinant vaccines in plants," Vaccine, 2005, 23:2042-2048.
Goldenkova et al., "A Thermostable *Clostridium thermocellum* Lichenase-based Reporter System for Studying the Gene Expression Regulation in Prokaryotic and Eukaryotic Cells," Mol. Biol., 2002, 36:698-704.
Green et al., "Transient protein expression in three *Pisum sativum* (green pea) varieties," Biotechnology Journal, vol. 4, No. 2, Feb. 2009, pp. 230-237.
Grierson et al., "Plant Viruses," Plant Molecular Biology, Blackie, London, pp. 126-146, 1984.
Gu et al., "Protection against anthrax toxin by vaccination with a DNA plasmid encoding anthrax protective antigen," Vaccine, 1999, 17:340.
Hahn et al., "Native-like in-vivo folding of a circularly permuted jellyroll protein shown by crystal structure analysis," Proc. Natl. Acad. Sci., USA, 1994, 91(22):10417-10421.
Heath et al., 1998, Vaccine, 16:131-7.
Hellens et al., "pGreen: a versatile and flexible binary Ti vector for *Agrobacterium*-mediated plant transformation" Plant Molecular Biology 2000, 42: 819-832.
Herbert and Lumsden, "*Trypanosoma brucei*: A rapid 'matching' method for estimating the host's parasitemia," Exp. Parasitol, 40:427, 1976.
Hobson et al., "The role of serum haemagglutination-inhibiting antibody in protection against challenge infection with influenza A2 and B viruses," J. Hyg., 1972, 70:767.
Holt et al., "Domain antibodies: proteins for therapy," Trends in Biotechnology, Elsevier Publications, Cambridge, GB, vol. 21, No. 11, Nov. 2003, pp. 484-490.
Huang et al., "Plant-derived measles virus hemagglutinin protein induces neutralizing antibodies in mice," Vaccine, Feb. 28, 2001, vol. 19, No. 15-16, pp. 2163-2171.
Huber et al., (2006), Clin. Vaccine Immunol, 13:981-90.
Hull et al., "Human-derived, plant-produced monoclonal antibody for the treatment of anthrax," Vaccine, 2005, 23:2082-2086.
Hunter et al., "Messenger RNA for the Coat Protein of Tobacco Mosaic Virus" Nature 1976, 260: 759-760.
Huse et al. (1989) Science 246:1275.
Ishikawa et al., "In Vitro Mutagenesis of the Putative Replicase Genes of Tobacco Mosaic Virus" Nucleic Acids Res. 1986, 14: 8291-8308.
Jaspars et al., "Plant Viruses With a Multipartite Genome" Adv. Virus Res. 1974, 19: 37-149.
Jirholt et al., (1998) Gene 215:471.
Johnson et al., Respiratory syncytial virus (RSV) G glycoprotein is not necessary for vaccine-enhanced disease induced by immunization with formalin-inactivated RSV, J. Virol, 78(11):6024-32, 2004.
Jones et al. (1986) Nature 321:522.
Kao et al., "A Method for High-frequency Intergeneric Fusion of Plant Protoplasts," *Planta*, 1974, 115:355.
Kang et al. (1991) Proc. Natl. Acad. Sci USA 88:4363.
Kapila et al., "An *Agrobacterium*-mediated transient gene expression system for intact leaves," Plant Sci., 1997, 122:101-108.
Kapusta et al., "A plant-derived edible vaccine against hepatitis B virus," FASEB J., 1999, 13:1796-1799.
Katayama and Mine, 2006, J. Agric. Food Chem., 54:3271-6.

Kikkert et al., "Biological Projectiles (Phage, Yeast, Bacteria) for Genetic Transformation of Plants," In Vitro Cell. Dev. Bio.—Plant, 1999. 35(1):43-50.
Klein et al., "High-velocity microprojectiles for delivering nucleic acids into living cells," Nature, 1987, 327:70-73.
Knapp et al., "Conundrum of the Lack of Defective RNAs (dRNAs) Associated with Tobamovirus Infections: dRNAs That Can Move Are Not Replicated by the Wild-Type Virus; dRNAs That Are Replicated by the Wild-Type Virus Do Not Move," J. Virol., 2001, 75:5518.
Knudsen and Muller, "Transformation of the developing barley endosperm by particle bombardment," *Planta*, 1991, 185:330-336.
Konieczny et al. (1981) Haematologia (Budap.) 14:95.
Krebber et al., J Immunol Methods 201:35-55, 1997.
Krens et al., "In vitro transformation of plant protoplasts with Ti-plasmid DNA," Nature, 1982, 296:72-74.
Kubler-Kielb, J. et al., "Long-lasting and transmission-blocking activity of antibodies to *Plasmodium falciparum* elicited in mice by protein conjugates of Pfs25," Proceedings of the National Academy of Sciences of USA, vol. 104, No. 1, Jan. 1, 2007, pp. 293-298.
Kumagai, et al., "Rapid, High-Level Expression of Glycosylated Rice α-Amylase in Transfected Plants by an RNA Viral Vector" Gene 2000, 245: 169-174.
Lambkin et al., "Strong local and systemic protective immunity induced in the ferret model by an intranasal virosome-formulated influenza subunit vaccine," Vaccine, 2004, 22:4390.
Lawton et al., "Expression of a Soybean (3-Conclycinin Gene Under the Control of the Cauliflower Mosaic Virus 35S and 19S Promoters in Transformed Petunia Tissues" Plant Mol. Biol. 1987, 9: 315-324.
Lee, J. T. and Air, G. M., "Contacts between influenza virus N9 neuraminidase and monoclonal antibody NC10," Virology, 300(2): 255-268, Sep. 1, 2002.
Leite et al., "Expression of correctly processed human growth hormone in seeds of transgenic tobacco plants," Molecular Breeding, 2000, 6: 47-53.
Lensen, A. et al., "Measurement by membrane feeding of reduction in *Plasmodium falciparum* transmission induced by endemiuc sera," Trans R Soc Trop Med Hyg. Jan.-Feb. 1996;90(1):20-2.
Lewandowski and Dawson, "Deletion of Internal Sequences Results in Tobacco Mosaic Virus Defective RNAs That Accumulate to High Levels without Interfering with Replication of the Helper Virus," Virology, 1998, 251:427-437.
Li et al. (Parasite Immunology, 2007, 29:191-199, published online Jan. 2007).
Lim et al., "An Anthrax Lethal Factor-Neutralizing Monoclonal Antibody Protects Rats before and after Challenge with Anthrax Toxin," Infection and Immunity, 2005, 73:6547.
Lin et al., "Treatment of Established Tumors with a Novel Vaccine That Enhances Major Histocompatibility Class II Presentation of Tumor Antigen," Cancer Research,1996, 56:21.
Little et al., "Passive Protection by Polyclonal Antibodies against *Bacillus anthracis* Infection in Guinea Pigs," Infect. Immun., 1997, 65:5171-5175.
Little et al., "Of mice and men: hybridoma and recombinant antibodies," Immunology Today, Elsevier Publications, Cambridge, GB, vol. 21, No. 8, Aug. 1, 2000, pp. 364-370.
Loesch-Fries, et al., "Expression of Alfalfa Mosaic Virus RNA 4 cDNA Transcripts In Vitro and In Vivo" Virology 1985, 146: 177-187.
Lorence and Verpoorte (2004), Methods Mol. Biol., 267:329-50.
Lubega et al., "Immunization with a tubulin-rich preparation from *Trypanosoma brucei* confers broad protection against African trypanosomosis," Exp. Parasitol., 2002, 102:9-22.
Lubega et al., "*Trypanosoma brucei*: anti-tubulin antibodies specifically inhibit trypanosome growth in culture," Exp. Parasitol., 2002, 102:134-142.
Maassab et al., "Evaluation of a Cold-Recombinant Influenza Virus Vaccine in Ferrets," The Journal of Infectious Diseases, vol. 146, No. 6, Dec. 1982, pp. 780-790.
Maliga et al., "Transient Cycloheximide Resistance in a Tobacco Cell Line," Mol. Gen. Genet., 1976, 149, 267-271.
Marillonnet Sylvestre et al., "Systemic *Agrobacterium tumefaciens*-mediated transfection of viral replicons for efficient transient expression in plants," Nature Biotechnology, 23(6):718-723, 2005.

(56) References Cited

OTHER PUBLICATIONS

Mathew, Plant Viruses Online—Cassava Indian mosaic bigeminvirus (http://image.fs.uidaho.edu/vide/descr173.htm), downloaded on Feb. 21, 2006, 5 pgs.

Mbawuike et al., 2007, Vaccine, 25:3263-9.

McCormick et al., "Rapid Production of Specific Vaccines for Lymphoma by Expression of the Tumor-Derived Single-Chain Fv Epitopes in Tobacco Plants" *Proc. Natl. Acad. Sci. USA* 1999, 96: 703-708.

McHugh et al., "Improved stability of a protein vaccine through elimination of a partially unfolded state," *Protein Science*, 2004, vol. 13, pp. 2736-2743.

Mellin et al., "Human Papillomavirus (HPV) DNA in Tonsillar Cancer: Clinical Correlates, Rise of Relapse, and Survival," *International Journal of Cancer*, 2000, 89:300-304.

Menczel et al. "Streptomycin Resistant and Sensitive Somatic Hybrids of *Nicotiana tabacum* + *Nicotiana knightiana*: Correlation of Resistance to *N. tabacum* Plastids," *Theor. Appl. Genet.*, 1981, 59, 191-195.

Meshi et al., "Function of the 30 kd Protein of Tobacco Mosaic Virus: Involvement in Cell-To-Cell Movement and Dispensability for Replication" *EMBO J.* 1987, 6: 2557-63.

Mett et al., "A plant-produced influenza subunit vaccine protects ferrets against virus challenge," *Influenza and Other Respiratory Viruses*, Blackwell Publishing Ltd., UK, vol. 2, No. 1, Jan. 1, 2008, pp. 33-40.

Mett, V., et al., "A plant-produced plague vaccine candidate confers protection to monkeys," Vaccine, Apr. 20, 2007, vol. 25, No. 16, pp. 3014-3017.

Mett, V. et al., "Plants as biofactories," Biologicals: Journal of the International Association of Biological Standardization, vol. 36, No. 6, Nov. 2008, pp. 354-358.

Moayeri et al., "The roles of anthrax toxin in pathogenesis," Curr Opin Michrobiol, 7(1):19-24, 2004.

Modelska et al., "Immunization against rabies with plant-derived antigen," *Proc. Natl. Acad. Sci., USA*, 1998, 95:2481-2485.

Moreira et al., "A Thermostable Maltose-tolerant α-anylase from Asperillgus Tamarii," J. Basic Microbiology, 44: 29-35, 2004.

Morrison et al. (1984) Proc. Natl. Acad. Sci USA 81:6851.

Morrison et al. (1986) Mt. Sinai J. Med. 53:175.

Murashige et al., "A Revised Medium for Rapid Growth and Bio Assays with Tobacco Tissue Cultures," *Physiologia Plantarum*, 1962, 15:473.

Musiychuk et al., "A launch vector for the production of vaccine antigens in plants," *Influenza and Other Respiratory Viruses*, 2007, 1:1.

Musiychuk et al., "Preparation and properties of *Clostridium thermocellum* lichenase deletion variants and their use for construction of bifunctional hybrid proteins," *Biochemistry(MOSC)*, vol. 65(12), pp. 1397-1402, Dec. 2000.

Nagy et al., Thermal stability of chemically denatured green fluorescent protein (GFP)—A preliminary study, 2004, Thermochimica Acta, vol. 410, No. 1, abstract.

Nass, "Anthrax Vaccine—Model of a Response to the Biologic Warfare Threat," *Infect. Dis. Clin. North Am.*, 1999, 13,187-208.

NCBI GenBank Accession No. ABP96852, "Influenza A virus" (A/Egypt/2616-NAMRU3/2007(H5N1)) hemagglutinin (HA) gene, complete CDS, Apr. 30, 2007.

NCBI GenBank Accession No. AAS93885, "Influenza A virus" (A/Cheju/274/2002(H3N2)) neuraminidase (NA) gene, complete CDS, Apr. 25, 2004.

Neeleman et al., "Role of Alfalfa Mosaic Virus Coat Protein Gene in Symptom Formation" *Virology* 1991, 181: 687-693.

Neeleman et al., "Infection of Tobacco With Alfalfa Mosaic Virus cDNAs Sheds Light on the Early Function of the Coat Protein" *Virology* 1993, 196: 883-887.

Noah et al., "Qualification of the hemagglutination inhibition assay in support of pandemic influenza vaccine licensure," Clin. Vaccine Immunol, 16(4):558-566, 2009.

Park et al., "Molecular Biology of Cervical Cancer and Its Precursors," Cancer, 1995, 76:1902-1913.

Parkhill et al., 2001, Nature 413:523-7.

Peres et al., 2001, "Shoot regeneration capacity from roots and transgenic hairy roots of tomato cultivars and wild related species," *Plant Cell, Tissue, and Organ Culture*, 2001, 65:37-44.

Petosa et al., "Crystal structure of the anthrax toxin protective antigen," *Nature*, 1997, 385:833-838.

Pfitzner et al., "Isolation and characterization of cDNA clones encoding pathogenesis-related proteins from tobacco mosaic virus infected tobacco plants," Nucleic Acids Research, 15(11):4449-4465, 1987.

Pilon-Smits et al., "Overexpression of ATP Sulfurylase in Indian Mustard Leads to Increased Selenate Uptake, Reduction, and Tolerance" *Plant Physiol*. 1999, 119(1): 123-132.

Piruzian et al., "A reporter system for prokaryotic and eukaryotic cells based on the thermostable lichenase from *Clostridium thermocellum*," Mol Genet Genomics, 266(5): 778-86, Jan. 2002, Epub Nov. 27, 2001.

Piruzian et al., "The use of a thermostable B-glucanase gene from *Clostridium thermocellum* as a reporter gene in plants," Mol Gen Genet 257(50): 561-7, Mar. 1998.

Pokorna et al., "Combined immunization with fusion genes of mutated E7 gene of human papillomavirus type 16 did not enhance antitumor effect," The Journal of Gene Medicine, 7(6): 696-707, 2005.

Potter et al., "Immunity to Influenza in Ferrets II. Influence of Adjuvants on Immunization," *Br. J Exp. Pathol.*, 1972, 53:168.

Potter et al., "Immunity to Influenza in Ferrets VI. Immunization with Adjuvanted Vaccines," *Arch. Gesamte Virusforsch.*, 1973, 42:285.

Potter et al., "Immunity to influenza in ferrets V. Immunization with inactivated virus in adjuvant 65," *J. Hyg. Lond.*, 1973, 71:97.

Pruett PS, et al., "Critical interactions in binding antibody NC41 to influenza N9 neuraminidase: amino acid contacts on the antibody heavy chain," Biochemistry, 37:10660-10670, 1998.

Qian et al., "Conjugating recombinant proteins to *Pseudomonas aeruginosa* ExoProtein A: A strategy for enhancing immunogenicity of malaria vaccine candidate," Vaccine, vol. 25, No. 20, Apr. 24, 2007, pp. 3923-3933.

Qing et al., "Transformation of Pakchoi (*Brassica rapa* L. ssp. *chinensis*) by *Agrobacterium* Infiltration," *Molecular Breeding*, 2000, 1:67-72.

Rao and Ravishankar, "Plant cell cultures: Chemical factories of secondary metabolites," Biotechnol. Adv., 2002, 20:101-153.

Rasooly-Balaban, "Trypanosome microtubule-associated protein p15 as a vaccine for the prevention of African sleeping sickness," *Vaccine*, vol. 22, No. 8, Feb. 25, 2004, pp. 1007-1015.

Reinstein et al., Degradation of the E7 human papillomavirus oncoprotein by the ubiquitin-proteasome system: targeting via ubiquitination of the N-terminal residue, Oncogene, 2000, 19, 5944-5950.

Riechmann et al. (1988) Nature 332:323.

Riva et al., "*Agrobacterium tumefaciens*: a natural tool for plant transformation," EJB Electronic J. Biotech., 1998, 1(3), 118-133.

Rudikoff et al., "Single amino acid substitution altering antigen-binding specificity," PNAS, 1982, 79:1979-1983.

Rowe et al., J. Clin. Microbiol., 1999, 37:937-43.

Sabbatini et al., 2007, Clin. Cancer Res., 13:4170-7.

Saito, et al., "Long-Distance Movement and Viral Assembly of Tobacco Mosaic Virus Mutants" Virology 1990, 176: 329-336.

Santi, V., et al., "Protection conferred by recombinant *Yersinia pestis* antigens produced by a rapid and highly scalable plant expression system," Proc. Natl. Acad. Sci. USA, Jan. 24, 2006, vol. 103, No. 4, pp. 861-866.

Saravolac EG, et al. "Immunoprophylactic strategies against respiratory influenza virus infection." Vaccine, Mar. 21, 2001;19(17-19):2227-32.

Scheiblauer et al., "Pathogenicity of influenza A/Seal/Mass/1/80 virus mutants for mammalian species," *Arch Virol*, (1995), 140: 341-384.
Schell et al., "Transgenic Plants as Tools to Study the Molecular Organization of Plant Genes." *Science* 1987, 237: 1176-1183.
Schild et al. (1975) Bull. World Health Org., 52:223-31.

(56) References Cited

OTHER PUBLICATIONS

Seedorf et al., "Human Papillomavirus Type 16 DNA Sequence," *Virology*, 1985, 145:181.
Sen et al., Appl Biochem Biotechnol., 143(3):212-23, Dec. 2007.
Shima et al., "Hyperthermaphilic and salt-dependent formyltransferase from *Methanopyrus kanleri*," Biochem Soc. Trans., 32:269-272, 2004.
Shimasaki et al., "Rapid diagnostics: the detection of neuraminidase activity as a technology for high-specificity targets," Philosophical transactions of the Royal Society of London. Series B, Biological sciences, 356(1416): 1925-1931 (Dec. 29, 2001).
Shivprasad et al., "Heterologous Sequences Greatly Affect Foreign Gene Expression in Tobacco Mosaic Virus-Based Vectors," *Virology*, 1999, 255(2):312-23.
Singh et al., "Gln277 and Phe544 residues are involved in thermal inactivation of protective antigen of *Bacillus anthracis*," *Biochemical and Biophysical Research Communications*, 2002, vol. 296, pp. 1058-1062.
Singh et al., "Study of Immunization against Anthrax with the Purified Recombinant Protective Antigen of *Bacillus anthracis*," *Infect. Immun.*, 1998, 66, 3447-3448.
Singh et al., "Thermal inactivation of protective antigen of *Bacillus anthracis* and its prevention by polyol osmolytes," *Biochemical and Biophysical Research Communications*, 2004, vol. 322, pp. 1029-1037.
Shoji et al, "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 2009, 27:3467-3470.
Shoji et al., "Plant-expressed HA as a seasonal influenza vaccine candidate," *Vaccine*, vol. 26, No. 23, Jun. 2, 2008, pp. 2930-2934.
Smahel et al., "Modified HPV16 E7 Genes as DNA Vaccine against E7-Containing Oncogenic Cells," *Virology*, 281, 231-238 (2001).
Smahel et al., "Enhancement of immunogenicity of HPV16 E7 oncogene by fusion with *E. coli* β-glucuronidase," The Journal of Gene Medicine, 6(10):1092-1101, 2004.
Snow et al, 2005, Nature, 434:214-7.
Soderlind et al. (1999) Immunotechnol. 4:279.
Soderlind et al. (2000) Nature Biotechnol. 18:852.
Soini et al., "Presence of human papillomavirus DNA and abnormal p53 protein accumulation in lung carcinoma," *Thorax*, 1996, 51:887-893.
Spilliaert et al., "Cloning and sequencing of a *Rhodothermus marinus* gene, bglA, coding for a thermostable beta-glucanase and its expression in *Escherichia coli," Eur. J Biochem.*, vol. 224(3):923-930, Sep. 15, 1994.
Stewart et al., "Mutant barley (1-→3,1-→4)-β-glucan endohydrolases with enhanced thermostability," Protein Engineering, vol. 14, No. 4, pp. 245-253, (2001).
Sweet et al., "Pathogenicity of Influenza Virus"; Microbiological Reviews, Jun. 1980, p. 303-330.
Tacket et al., "Human Immune Responses to a Novel Norwalk Virus Vaccine Delivered in Transgenic Potatoes," *J. Infect. Dis.*, 2000, 182:302-305.
Thanavala et al., "Immunogenicity in humans of an edible vaccine for hepatitis B," Proc. Natl. Acad. Sci., USA, 2005, 102:3378-3382.
Thomas et al., "HPV-18 E6 mediated inhibition of p53 DNA binding activity is independent of E6 induced degradation," Oncogene, 1995, 10:261-8.
Throsby, M. et al., "Heterosubtypic neutralizing monoclonal antibodies cross-protective against H5NI and H1N1 recovered from human IgM+ memory B cells," Plos One 2008 LNKD-PUBMED:19079604, vol. 3, No. 12, 2008, p. E3942.
Toms et al., "Behaviour in Ferrets of Swine Influenza Virus Isolated from Man," The Lancet, Jan. 8, 1977, pp. 68-71.
Tsai et al., "Crystal structure of a natural circularly permuted jellyroll protein: 1,3-1,4-beta-D-glucanase from Fibrobacter succinogens," J Mol Biol., 330(3):607-20, Jul. 11, 2003.
Turpen et al., "Transfection of whole plants from wounds inoculated with *Agrobacterium tumefaciens* containing cDNA of tobacco mosaic virus," J. Virol, Methods, 1993, 42:227.
UniProt Database [Online] EBI Accession No. Q0PDN1, "SubName: Full=Hemagglutinin," Sep. 5, 2006.
UniProt Database [Online] EBI Accession No. A9X0E7, "SubName: Full=Hemagglutinin; Flags: Precursor," Feb. 5, 2008.
UniProt Database accession No. P04107 Nov. 1, 1986.
Van der Kolk, M. et al., Parasitology, Jan. 2005; 130(Pt 1): 13-22 (Erratum in: Parasitology Oct. 2005; 131(Pt 4):578.
Van Der Kuyl et al., "Complementation and Recombination between Alfalfa Mosaic Virus RNA3 Mutants in Tobacco Plants," *Virology*, 1991, 183:731-738.
Van Der Kuyl et al., "Role of Alfalfa Mosaic Virus Coat Protein in Regulation of the Balance between Viral Plus and Minus Strand RNA Synthesis" *Virology*, 1991, 185:496-499.
Van Der Vossen, et al., "Early and Late Functions of Alfalfa Mosaic Virus Coat Protein Can Be Mutated Separately" Virology 1994, 202: 891-903.
Verch et al., "Expression and assembly of a full-length monoclonal antibody in plants using a plant virus vector," *J. Immunol. Methods*, 1998, 220, 69-75.
Voinnet et al. (2003) Plant J. 33:949-56.
Volten-Doting, Plant Viruses Online (http://image.fs.uidaho.edu/vide/descr009.htm) (downloaded May 18, 2002) (11 pgs.).
Wagner et al., "Plant virus expression systems for transient production of recombinant allergens in *Nicotiana benthamiana," Methods: A Companion to Methods in Enzymology*, vol. 32, No. 3, Mar. 1, 2004; pp. 228-232.
Wang et al, "Immunogenicity of *Plasmodium yoelii* merozoite surface protein 4/5 produced in transgenic plants," International Journal of Parasitology, vol. 38, No. 1, Dec. 22, 2007 pp. 103-110.
Wang et al., "Structural Basis for Thermostability of γ-Glycosidase from the Thermophilic *Eubacterium Thermus* Nonproteolyticus HG102," J. Bacteriology, 185: 4248-55, 2003.
Webster et al., "Measles virus hemagglutinin protein expressed in transgenic lettuce induces neutralizing antibodies in mice following mucosal vaccination," *Vaccine*, Apr. 24, 2006, vol. 24, No. 17, pp. 3538-3544.
Webster et al., "Protection of ferrets against influenza challenge with a DNA vaccine to the haemagglutinin," *Vaccine*, (1994), vol. 12, No. 16, pp. 1495-1498.
Webster RG, et al., "Antigenic Structure and Variation in an Influenza Virus N9 Neuraminidase," J. Virology, 61:2910-2916, 1987.
Wiesmuller et al., "Peptide Vaccines and Peptide Libraries," Biol Chem., 382(4): 571-9, Apr. 2001.
Williamson et al., Infect. Immun., 2005, 73:3598-608.
Williamson et al., 2000, Vaccine, 19:566-71.
Williamson et al., 1995, FEMS Immunol. Med. Microbiol., 12:223-30.
Wilson et al., "Structure of the haemagglutinin membrane glycoprotein of influenza virus at 3 Å resolution," *Nature*, 1981, 289:366.
Winter and Milstein (1991) Nature 349:293.
Woo, P. T. K., "The Haematocrit Centrifuge Technique for the Diagnosis of African Trypanosomiasis," Acta Tropica, 27:384, 1970.
The World Health Organization Global Influenza Program Surveillance Network, Evolution of H5N1 Avian Influenza Viruses in Asia, 2005, Emerging Infectious Diseases, vol. 11, No. 10, pp. 1515-1521.
Yang, M. et al., "Production and diagnostic application of monoclonal antibodies against influenza virus H5," Journal of Virological Methods, vol. 162, No. 1-2, Aug. 21, 2009, pp. 194-202.
Yusibov et al., "Antigens Produced in Plants by Infection With Chimeric Plant Viruses Immunize Against Rabies Virus and HIV-1" *Proc. Natl. Acad. Sci. USA* 1997, 94: 5784-5788.
Yusibov et al., "N-Terminal Basic Amino Acids of Alfalfa Mosaic Virus Coat Protein Involved in the Initiation of Infection" *Virology* 1995, 208: 405-407.
Yusibov, et al., "Functional Significance of Three Basic N-Terminal Amino Acids of Alfalfa Mosaic Virus Coat Protein" *Virology* 1998, 242: 1-5.

(56) References Cited

OTHER PUBLICATIONS

Yusibov et al., "Purification, characterization, assembly and crystallization of assembled alfalfa mosaic virus coat protein expressed in *Escherichia coli*," *J Gen. Virol.*, 1996, 77:567-573.
Yusibov et al., "Expression in plants and immunogenicity of plant virus-based experimental rabies vaccine" *Vaccine*, 2002, 20:3155-3164.
Yusibov et al., "An influenza N1 neuraminidase-specific monoclonal antibody with broad inactivating activity against H5N1 viruses," Human Antibodies, 16(1-2):33, 2007.
Yusibov et al., "An influenza N1 neuraminidase-specific monoclonal antibody protects animal against live challenge with homologous H5N1 virus," *Human Antibodies*, vol. 17, No. 1-2, 2008, p. 15.
Yusibov et al., "The Potential of Plant Virus Vectors for Vaccine Production," Drugs in R & D 7(4):203-217), 2006.
Yusibov et al., "Novel approaches to the development of vaccines: progress on anthrax". Joint meeting, Sep. 27-30, 2005, Bergen, Norway. Sep. 1, 2005, p. 13. Retrieved from the Internet: URL:http://www.sgm.ac.uk/meetings/pdfabstractsjbergen2005abs.pdf [retrieved on Jun. 13, 2012], 44 pgs.
Zapata et al., (1995) Prot. Eng., 8:1057.
Zumbach et al., "Antibodies Against Oncoproteins E6 and E7 of Human Papillomavirus Types 16 and 18 in Patients with Head-and-Neck Squamous-Cell Carcinoma," International Journal of Cancer, 2000, 85:815-818.
Advisory Action dated Jan. 15, 2010 for U.S. Appl. No. 11/706,568 (3 pgs.).
Communication dated May 19, 2009 for European Application No. 06850507.2.
Communication dated Sep. 23, 2009 for corresponding European Appln. No. 04 776 107.7 (3 pgs.).
Communication dated Apr. 21, 2010 for EP Appln. No. 04 776 107.7 (4 pgs.).
Communication dated May 20, 2010 for EP Appln. No. 04 776 107.7 (3 pgs.).
Communication dated Feb. 18, 2010 for EP Appln. No. EP 07750905.7 (2 pgs.).
Examiner's First Report dated Aug. 24, 2011 for Australian Appln. No. 2007215082 (3 pgs.).
International Preliminary Report on Patentability dated Apr. 23, 2008 for International Application No. PCT/US2006/030545.
International Preliminary Report on Patentability dated Aug. 19, 2008 for Int'l. Appln. No. PCT/US07/003948 (6 pgs.).
International Preliminary Report on Patentability dated Aug. 19, 2008 for Int'l. Appln. No. PCT/US07/003973 (6 pgs.).
International Preliminary Report on Patentability dated Aug. 19, 2008 for Int'l. Appln. No. PCT/US07/003969 (6 pgs.).
International Preliminary Report on Patentability dated Mar. 17, 2009 for Int'l Appln. No. PCT/US07/004103 (5 pgs.).
International Preliminary Report on Patentability dated Nov. 3, 2009 for Int'l. Appln. No. PCT/US08/061782 (7 pgs).
International Preliminary Report on Patentability dated Jan. 12, 2010 for International Appln. No. PCT/US2008/069860 (5 pgs.).
International Preliminary Report on Patentability dated Mar. 4, 2010 for Int'l. Appln. No. PCT/US08/073776 (6 pgs.).
International Preliminary Report on Patentability dated Mar. 29, 2011 for Int'l Appln. No. PCT/US2009/058669 (12 pgs.).
International Preliminary Report on Patentability for International Appln. No. PCT/US2009/058640 dated Mar. 29, 2011 (7 pgs.).
International Search Report and Written Opinion dated Apr. 4, 2008 for International Application No. PCT/US2006/030545.
International Search Report and Written Opinion dated Aug. 3, 2007 for Int'l. Appln. No. PCT/US07/003973 (9 pgs.).
International Search Report and Written Opinion dated Jun. 18, 2008 for Int'l Appln. No. PCT/US07/003948 (9 pgs.).
International Search Report and Written Opinion dated Sep. 4, 2007 for Int'l. Appln. No. PCT/US07/003969 (10 pgs.).
International Search Report and Written Opinion dated Aug. 7, 2007 for Int'l. Appln. No. PCT/US07/004103 (9 pgs).
International Search Report and Written Opinion dated Oct. 21, 2008 for Int'l. Appln. No. PCT/US08/061782 (10 pgs.).
International Search Report and Written Opinion dated Apr. 24, 2009 for Int'l. Appln. No. PCT/US08/073776 (11 pgs.).
International Search Report dated Dec. 23, 2005 for International Appln. No. PCT/US04/16452 (2 pgs.).
International Search Report and Written Opinion dated May 29, 2009 for International Appln. No. PCT/US2008/069860 (8 pgs.).
International Search Report and Written Opinion dated May 11, 2010 for International Appln. No. PCT/US2009/058488 (20 pgs.).
International Search Report and Written Opinion dated May 19, 2010 for International Appln. No. PCT/US2009/058669 (21 pgs.).
International Search Report and Written Opinion for International Appln. No. PCT/US2009/058640 dated Feb. 2, 2010 (13 pgs.).
International Search Report and Written Opinion dated Jan. 27, 2011 for Int'l Appln. No. PCT/US10/050693 (7 pgs.).
Notification of Defects in Patent Application dated Sep. 16, 2010 for Israeli Patent Appln. No. 193391 (3 pgs.).
Office Action (non-final) dated Nov. 4, 2008 for U.S. Appl. No. 11/706,568 (7 pgs.).
Office Action (non-final) dated Jan. 6, 2009 for U.S. Appl. No. 11/706,568 (8 pgs.).
Office Action (final) dated Jul. 15, 2009 for U.S. Appl. No. 11/706,568 (7 pgs.).
Office Action (restriction requirement) dated Nov. 28, 2007 for U.S. Appl. No. 11/706,573 (8 pgs.).
Office Action (non-final) dated Apr. 16, 2008 for U.S. Appl. No. 11/706,573 (11 pgs.).
Office Action (non-final) dated Jan. 21, 2009 for U.S. Appl. No. 11/706,573 (10 pgs.).
Office Action (non-final) dated Feb. 22, 2010 for U.S. Appl. No. 11/706,573 (11 pgs.).
Office Action (non-final) dated Nov. 24, 2010 for U.S. Appl. No. 11/706,573 (11 pgs.).
Supplementary European Search Report dated May 5, 2010 for European Appln. No. EP 07750784 (8 pages).
Supplementary European Search Report dated Oct. 8, 2009 for European Appln. No. EP 07750950 (5 pages).
Supplementary European Search Report dated Jun. 9, 2010 for European Appln. No. 08780572.
Supplementary European Search Report dated Dec. 5, 2006 for European Appln. No. 04 776 107.7 (2 pgs.).

Figure 3 pp=plant-produced

HUMANIZED NEURAMINIDASE ANTIBODY AND METHODS OF USE THEREOF

CROSS-REFERENCE TO RELATED APPLICATIONS

This application is a divisional of U.S. application Ser. No. 13/121,235, filed Sep. 6, 2011, now U.S. Pat. No. 8,734,803, which is a National Stage application under 35 U.S.C. 371 of International Application No. PCT/US2009/058640, having an International Filing Date of Sep. 28, 2009, which claims benefit of priority from U.S. Provisional Application Ser. No. 61/100,740, filed Sep. 28, 2008, which is incorporated herein by reference in its entirety.

TECHNICAL FIELD

This document relates to antibodies against influenza, and more particularly to an influenza N1 neuraminidase-specific monoclonal antibody that can protect animals against live challenge with homologous H5N1 virus.

BACKGROUND

Influenza has a long history characterized by waves of pandemics, epidemics, resurgences and outbreaks. Influenza is a highly contagious disease with the potential to be devastating both in developing and developed countries. In spite of annual vaccination efforts, influenza infections result in substantial morbidity and mortality each year. Although pandemics do not occur very often, flu strains have recently emerged that increase the potential for an influenza pandemic. An example is the avian influenza virus of the type H5N1, which as caused an epidemic in poultry in Asia as well as in regions of Eastern Europe, and has persistently spread throughout the globe. The rapid spread of infection and the cross species transmission from birds to humans has increased the potential for outbreaks in human populations and the risk of a pandemic. The virus is highly pathogenic, with a mortality rate of over fifty percent in birds as well as the few human cases that have been identified. Human to human transmission of the virus would have the potential to result in rapid, widespread illness and mortality.

The major defense against influenza is vaccination. Influenza viruses are segmented, negative-strand RNA viruses belonging to the family Orthomyxoviridae. Influenza virus hemagglutinin glycoprotein (HA) generally is considered the most important viral antigen with regard to the stimulation of neutralizing antibodies and vaccine design. The presence of viral neuraminidase (NA) has been shown to be important for generating multi-arm protective immune responses against the virus. Antiviral agents that inhibit neuraminidase activity have been developed and can be an additional antiviral treatment upon infection. A third component considered useful in the development of influenza antivirals and vaccines is the ion channel protein M2.

Subtypes of the influenza virus are designated by different HA and NA that are the result of antigenic shift. Furthermore, new strains of the same subtype result from antigenic drift or from mutations in the HA or NA molecules that generate new and different epitopes. Although 15 antigenic subtypes of HA have been documented, only three of these subtypes (H1, H2, and H3) have circulated extensively in humans. Vaccination has become paramount in the quest for improved quality of life in both industrialized and underdeveloped nations. The majority of available vaccines still follow the basic principles of mimicking aspects of infection in order to induce an immune response that could protect against the relevant infection. However, generation of attenuated viruses of various subtypes and combinations can be time consuming and expensive. Along with emerging new technologies, in-depth understanding of a pathogen's molecular biology, pathogenesis, and interactions with an individual's immune system has resulted in new approaches to vaccine development and vaccine delivery. Thus, while technological advances have improved the ability to produce improved influenza antigens vaccine compositions, there remains a need to provide additional sources of protection against to address emerging subtypes and strains of influenza.

SUMMARY

This document relates to antibody compositions and methods for producing antibody compositions, including production in plant systems. This document further relates to vectors encoding antibodies or antigen binding fragments thereof, as well as fusion proteins, plant cells, plants, compositions, and kits comprising antibodies or antigen binding fragments thereof, and therapeutic and diagnostic uses in association with influenza infection in a subject.

This document is based in part on the identification of an anti-H5N1 neuraminidase monoclonal antibody that specifically inhibits N1 neuraminidase activity of highly pathogenic avian influenza (HPAI) strains from clades 1, 2, and 3. The N1NA-specific mAb, 2B9, can inhibit enzymatic activity of NA from several strains of H5N1, including oseltamivir-resistant HPAI isolates. The protective efficacy of this antibody has been demonstrated in animal challenge models (e.g., mouse models) using homologous virus. The specific and effective inhibition of N1NA renders this mAb a useful therapeutic tool in the treatment and/or prevention of human infection. The 2B9 mAb also can be useful for treating and/or preventing infection with drug-(e.g., oseltamivir- and/or zanimivir-) resistant strains of HPAI. In addition, the mAb can be a useful diagnostic tool for typing suspected H5N1 human isolates in conjunction with other diagnostic approaches.

Thus, this document provides antibodies against influenza neuraminidase antigens, as well as antibody components produced in plants. The antibodies can inhibit neuraminidase activity. Also provided are antibody compositions that are reactive against influenza neuraminidase antigen. In addition, methods for production and use of the antibodies and compositions are provided herein.

In one aspect, this document features an isolated monoclonal antibody that binds neuraminidase, wherein the antibody has the ability to inhibit neuraminidase enzyme activity, and wherein the antibody comprises a light chain variable region amino acid sequence as set forth in amino acids 1 to 127 of SEQ ID NO:5, and a heavy chain variable region amino acid sequence as set forth in amino acids 1 to 137 of SEQ ID NO:6. The antibody can be an antigen-binding fragment of an antibody (e.g., an scFv, Fv, Fab', Fab, diabody, linear antibody or F(ab')$_2$ antigen-binding fragment of an antibody, or a CDR, univalent fragment, single domain antibody). The antibody can be a human, humanized or part-human antibody or antigen-binding fragment thereof (e.g., a humanized antibody comprising a heavy chain amino acid sequence set forth in SEQ ID NO:7, a humanized antibody comprising a heavy chain amino acid sequence set forth in SEQ ID NO:8, a humanized antibody comprising a light chain amino acid sequence set forth in SEQ ID NO:9, or a humanized antibody comprising a light chain amino acid sequence set forth in SEQ ID NO:10). The antibody can be a recombinant antibody.

In another aspect, this document features an antibody that binds neuraminidase, wherein the antibody has the ability to inhibit neuraminidase enzyme activity, and wherein the antibody comprises a light chain amino acid sequence that is at least 85 percent identical (e.g., at least 90 percent identical, or at least 95 percent identical) to the amino acid sequence set forth in SEQ ID NO:9 or SEQ ID NO:10, and a heavy chain amino acid sequence that is at least 85 percent identical (e.g., at least 90 percent identical, or at least 95 percent identical) to the amino acid sequence set forth in SEQ ID NO:7 or SEQ ID NO:8.

The antibodies provided herein can be produced in a plant. The antibodies can be operatively attached to a biological agent or a diagnostic agent (e.g., an agent that cleaves a substantially inactive prodrug to release a substantially active drug, such as an anti-influenza agent, or an anti-viral agent such as an anti-influenza agent). The antibodies can be operatively attached to a diagnostic, imaging or detectable agent (e.g., an X-ray detectable compound, a radioactive ion or a nuclear magnetic spin-resonance isotope, such as (a) the X-ray detectable compound bismuth (III), gold (III), lanthanum (III) or lead (II); (b) the detectable radioactive ion copper$^{67}$, gallium$^{67}$, gallium$^{68}$, indium$^{113}$, iodine$^{123}$, iodine$^{125}$, iodine1$^{31}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; or (c) the detectable nuclear magnetic spin-resonance isotope cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III). The antibodies can be operatively attached to biotin, avidin or to an enzyme that generates a colored product upon contact with a chromogenic substrate. The antibodies can be operatively attached to the biological agent as a fusion protein prepared by expressing a recombinant vector that comprises, in the same reading frame, a DNA segment encoding the antibody operatively linked to a DNA segment encoding the biological agent. The antibodies can be operatively attached to the biological agent via a biologically releasable bond or selectively cleavable linker.

In another aspect, this document features a recombinant, plant-produced monoclonal antibody that binds neuraminidase, wherein the antibody has the ability to inhibit neuraminidase enzyme activity, and wherein the antibody comprises a light chain amino acid sequence as set forth in SEQ ID NO:5, and a heavy chain amino acid sequence as set forth in SEQ ID NO:6.

This document also features a pharmaceutical composition comprising an antibody as described herein, and a pharmaceutically acceptable carrier. The composition can be formulated for parenteral administration. The antibody can be a recombinant, plant-produced antibody. The pharmaceutically acceptable composition can be an encapsulated or liposomal formulation. The composition can further comprise a second therapeutic agent.

Also provided herein is a method for treating an influenza infection in a subject in need thereof, comprising administering to the subject an amount of a composition as provided herein that is effective to reduce symptoms of the influenza infection in the subject.

In addition, this document features use of an antibody as described herein for diagnosing a condition due to infection by a human influenza virus, or for typing a human influenza virus, wherein binding of the antibody to the influenza virus is indicative of an N1 virus.

In still another aspect, this document features a method for treating a subject in need thereof, comprising providing a biological sample from the subject, contacting the biological sample with an antibody as provided herein, and, if the antibody shows detectable binding to the biological sample, administering the antibody to the subject. The subject can be a human patient (e.g., a human patient diagnosed as having influenza, and in some cases a human patient diagnosed as having an oseltamivir-resistant strain of influenza).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a depiction of a plasmid construct used to express neuraminidase in plants.

FIG. 2 is a graph plotting results of an ELISA, indicating differential binding of the 2B9 anti-N1 neuraminidase monoclonal antibody to wells coated with NIBRG-14 virions, NINA protein, N2NA protein, and H5HA protein, as indicated.

FIG. 3 is a graph plotting inhibition of N1 neuraminidase activity by 2B9 or, as a control, anti-RSV F protein, using the molar ratios as indicated on the X axis.

FIG. 4 is a graph plotting percent survival of mice treated with 2B9 or PBS prior to challenge with the A/VN/1203/04 H5N1 influenza strain.

FIG. 5 is a picture of a gel stained with Coomassie blue dye, showing the light (lower bands) and heavy (upper bands) chains of humanized, plant-produced 2B9 (h2B9) antibodies.

FIG. 6 is a graph plotting antigen binding by the indicated concentrations of various humanized 2B9 antibodies, as determined by an ELISA.

FIG. 7 is a series of graphs plotting the half life of hybridoma-produced (top panels) or plant-produced (bottom panels) 2B9 antibody, administered to mice intravenously (left panels) or intramuscularly (right panels).

DETAILED DESCRIPTION

Influenza Antigens

Influenza antigen proteins can include any immunogenic protein or peptide capable of eliciting an immune response against influenza virus. Generally, immunogenic proteins of interest include influenza antigens (e.g., influenza proteins), immunogenic portions thereof, or immunogenic variants thereof and combinations of any of the foregoing.

Influenza antigens can include full-length influenza proteins or fragments of influenza proteins. Where fragments of influenza proteins are utilized, such fragments can retain immunological activity (e.g., cross-reactivity with anti-influenza antibodies). Hemagglutinin and neuraminidase have the capacity to induce immunoprotective responses against viral infection, and are primary antigens of interest in generating antibodies.

Amino acid sequences of a variety of different influenza NA proteins (e.g., from different subtypes, or strains or isolates) are known in the art and are available in public databases such as GenBank. Exemplary full length protein sequences for NA of two influenza subtypes are provided below. The italicized portion at the beginning of each sequence represents the anchor peptide for that protein.

```
Vietnam H5N1 NA (NAV):
                                      (SEQ ID NO: 1)
MNPNQKIITIGSICMVTGIVSLMLQIGNMISIWVSHSIHTGNQHQ

SEPISNTNLLTEKAVASVKLAGNSSLCPINGWAVYSKDNSIRIGS

KGDVFVIREPFISCSHLECRTFFLTQGALLNDKHSNGTVKDRSPH

RTLMSCPVGEAPSPYNSRFESVAWSASACHDGTSWLTIGISGPDN

GAVAVLKYNGIITDTIKSWRNNILRTQESECACVNGSCFTVMTDG

PSNGQASHKIFKMEKGKVVKSVELDAPNYHYEECSCYPDAGEITC

VCRDNWHGSNRPWVSFNQNLEYQIGYICSGVFGDNPRPNDGTGSC

GPVSSNGAGGVKGFSFKYGNGVWIGRTKSTNSRSGFEMIWDPNGW

TETDSSFSVKQDIVAITDWSGYSGSFVQHPELTGLDCIRPCFWVE

LIRGRPKESTIWTSGSSISFCGVNSDTVGWSWPDGAELPFTIDK

Wyoming H3N2 NA (NAW):
                                      (SEQ ID NO: 2)
MNPNQKIITIGSVSLTISTICFFMQIAILITTVTLHFKQYEFNSP

PNNQVMLCEPTIIERNITEIVYLTNTTIEKEICPKLAEYRNWSKP

QCNITGFAPFSKDNSIRLSAGGDIWVTREPYVSCDPDKCYQFALG

QGTTLNNVHSNDTVHDRTPYRTLLMNELGVPFHLGTKQVCIAWSS

SSCHDGKAWLHVCVTGDDENATASFIYNGRLVDSIVSWSKKILRT

QESECVCINGTCTVVMTDGSASGKADTKILFIEEGKIVHTSTLSG

SAQHVEECSCYPRYPGVRCVCRDNWKGSNRPIVDINIKDYSIVSS

YVCSGLVGDTPRKNDSSSSSHCLDPNNEEGGHGVKGWAFDDGNDV

WMGRTISEKLRSGYETFKVIEGWSNPNSKLQINRQVIVDRGNRSG

YSGIFSVEGKSCINRCFYVELIRGRKQETEVLWTSNSIVVFCGTS

GTYGTGSWPDGADINLMPI
```

While sequences of exemplary influenza antigens are provided herein, and domains depicted for NA have been provided for exemplary strains, it will be appreciated that any sequence having immunogenic characteristics of a domain of NA can alternatively be employed. One skilled in the art will readily be capable of generating sequences having at least 75%, 80%, 85%, 90%, 95%, or more than 95% identity to the provided antigens. In certain embodiments, influenza antigens can be polypeptides having at least 95%, 96%, 97%, 98%, or more identity to a domain NA, or a portion of a domain NA, wherein the polypeptide retains immunogenic activity. Percent sequence identity is determined as described below. Sequences having sufficient identity to influenza antigen(s) that retain immunogenic characteristics can be capable of binding with antibodies that react with domains (antigen(s)) provided herein Immunogenic characteristics often include three dimensional presentation of relevant amino acids or side groups. One skilled in the art can readily identify sequences with modest differences in sequence (e.g., with difference in boundaries and/or some sequence alternatives, that, nonetheless preserve immunogenic characteristics). Further, one will appreciate that any domains, partial domains or regions of amino acid sequence of influenza antigen (e.g., NA) which are immunogenic can be generated using constructs and methods provided herein. Still further, domains or subdomains can be combined, separately and/or consecutively for production of influenza antigens.

Sequences of particular neuraminidase subtypes have been used as exemplary antigens, as described in detail herein. Various subtypes of influenza virus exist and continue to be identified as new subtypes emerge. It will be understood by one skilled in the art that the methods and compositions provided herein can be adapted to utilize sequences of additional subtypes. Such variation is contemplated and encompassed within the methods and compositions provided herein.

Transgenic plants expressing influenza antigen(s) (e.g., influenza protein(s) or fragments thereof) can be used for production in plant systems. Transgenic plants can be produced using methods well known in the art to generate stable production crops, for example. Plants utilizing transient expression systems also can be used for production of influenza antigen(s). When utilizing plant expression systems, whether transgenic or transient expression in plants is utilized, any of nuclear expression, chloroplast expression, mitochondrial expression, or viral expression can be used according to the applicability of the system to antigen desired. Furthermore, other expression systems for production of antigens can be used. For example, mammalian expression systems (e.g., mammalian cell lines such as CHO cells), bacterial expression systems (e.g., *E. coli*), insect expression systems (e.g., baculovirus), yeast expression systems, and in vitro expression systems (e.g., reticulate lysates) can be used to express antigens.

Production of Influenza Antigens:

Influenza antigens (including influenza protein(s), fragments, and/or variants thereof) can be produced in any desirable system; production is not limited to plant systems. Vector constructs and expression systems are well known in the art and can be adapted to incorporate use of influenza antigens provided herein. For example, influenza antigens (including fragments and/or variants) can be produced in known expression systems, including mammalian cell systems, transgenic animals, microbial expression systems, insect cell systems, and plant systems, including transgenic and transient plant systems.

In some embodiments, influenza antigens can be produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Also, plants can economically produce very large amounts of biomass without requiring sophisticated facilities. Moreover, plants are not subject to contamination with animal pathogens. Like liposomes and microcapsules, plant cells are expected to provide protection for passage of antigen to the gastrointestinal tract.

Plants can be utilized for production of heterologous proteins via use of various production systems. One such system includes use of transgenic/genetically-modified plants where a gene encoding target product is permanently incorporated into the genome of the plant. Transgenic systems can generate crop production systems. A variety of foreign proteins, including many of mammalian origin and many vaccine candidate antigens, have been expressed in transgenic plants and shown to have functional activity (Tacket et al. (2000) *J. Infect. Dis.* 182:302; and Thanavala et al. (2005) *Proc. Natl. Acad. Sci. USA* 102:3378). Additionally, administration of unprocessed transgenic plants expressing hepatitis B major surface antigen to non-immunized human volunteers resulted in production of immune response (Kapusta et al. (1999) *FASEB J.* 13:1796).

Another system for expressing polypeptides in plants utilizes plant viral vectors engineered to express foreign sequences (e.g., transient expression). This approach can allow for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout the entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying desired antigenic epitopes on their surface. This approach allows for time-efficient production of antigen and/or antibody candidates, since the particulate nature of an antigen and/or antibody candidate facilitates easy and cost-effective recovery from plant tissue. Additional advantages include enhanced target-specific immunogenicity, the potential to incorporate multiple antigen determinants and/or antibody sequences, and ease of formulation into antigen and/or antibody that can be delivered nasally or parenterally, for example. As an example, spinach leaves containing recombinant plant viral particles carrying epitopes of virus fused to coat protein have generated immune response upon administration (Modelska et al. (1998) *Proc. Natl. Acad. Sci. USA* 95:2481; and Yusibov et al. (2002) *Vaccine* 19/20:3155).

Plant Expression Systems

Any plant susceptible to incorporation and/or maintenance of heterologous nucleic acid and capable of producing heterologous protein can be utilized. In general, it will often be desirable to utilize plants that are amenable to growth under defined conditions, for example in a greenhouse and/or in aqueous systems. It may be desirable to select plants that are not typically consumed by human beings or domesticated animals and/or are not typically part of the human food chain, so that they can be grown outside without concern that expressed polynucleotide may be undesirably ingested. In some embodiments, however, it will be desirable to employ edible plants. In particular embodiments, it will be desirable to utilize plants that accumulate expressed polypeptides in edible portions of the plant.

Often, certain desirable plant characteristics will be determined by the particular polynucleotide to be expressed. To give but a few examples, when a polynucleotide encodes a protein to be produced in high yield (as will often be the case, for example, when antigen proteins are to be expressed), it will often be desirable to select plants with relatively high biomass (e.g., tobacco, which has additional advantages that it is highly susceptible to viral infection, has a short growth period, and is not in the human food chain). Where a polynucleotide encodes antigen protein whose full activity requires (or is inhibited by) a particular post-translational modification, the ability (or inability) of certain plant species to accomplish relevant modification (e.g., a particular glycosylation) may direct selection. For example, plants are capable of accomplishing certain post-translational modifications (e.g., glycosylation), but plants will not generate sialation patterns which are found in mammalian post-translational modification. Thus, plant production of antigen can result in production of a different entity than the identical protein sequence produced in alternative systems.

In some embodiments, crop plants, or crop-related plants can be used. In some cases, edible plants can be utilized.

Suitable plants include, without limitation, Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Exemplary plants are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.g., pepper), or *Nicotiana* (e.g., tobacco); Umbelliferae, particularly of the genus *Daucus* (e.g., carrot), *Apium* (e.g., celery), or *Rutaceae* (e.g., oranges); Compositae, particularly of the genus *Lactuca* (e.g., lettuce); Brassicaceae (Cruciferae), particularly of the genus *Brassica* or *Sinapis*. In certain aspects, exemplary plants can be plants of the *Brassica* or *Arabidopsis* genus. Some exemplary Brassicaceae family members include *Brassica campestris, B. carinata, B. juncea, B. napus, B. nigra, B. oleraceae, B. tournifortii, Sinapis alba*, and *Raphanus sativus*. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

Introducing Vectors into Plants:

In general, vectors can be delivered to plants according to known techniques. For example, vectors themselves can be directly applied to plants (e.g., via abrasive inoculations, mechanized spray inoculations, vacuum infiltration, particle bombardment, or electroporation). Alternatively or additionally, virions can be prepared (e.g., from already infected plants), and can be applied to other plants according to known techniques.

A wide variety of viruses are known that infect various plant species, and can be employed for polynucleotide expression (see, for example, *The Classification and Nomenclature of Viruses*, "Sixth Report of the International Committee on Taxonomy of Viruses," Ed. Murphy et al., Springer Verlag: New York, 1995, the entire contents of which are incorporated herein by reference; Grierson et al. *Plant Molecular Biology*, Blackie, London, pp. 126-146, 1984; Gluzman et al., *Communications in Molecular Biology: Viral Vectors*, Cold Spring Harbor Laboratory, Cold Spring Harbor, N.Y., pp. 172-189, 1988; and Mathew, *Plant Viruses Online*, available online on the University of Idaho web site at "image 'dot' fs 'dot' uidaho 'dot' edu 'slash' vide 'slash'"). In some embodiments, rather than delivering a single viral vector to a plant cell, multiple different vectors can be delivered that, together, allow for replication (and, optionally cell-to-cell and/or long distance movement) of viral vector(s). Some or all of the proteins can be encoded by the genome of transgenic plants. In certain aspects, described in further detail herein, these systems include one or more viral vector components.

Vector systems that include components of two heterologous plant viruses in order to achieve a system that readily infects a wide range of plant types and yet poses little or no risk of infectious spread. An exemplary system has been described previously (see, e.g., PCT Publication WO 00/25574 and U.S. Patent Publication No. 2005/0026291, which are incorporated herein by reference). As noted herein, viral vectors can be applied to plants (e.g., whole plants, portions of plants, sprouts, etc.) using various methods (e.g., through infiltration or mechanical inoculation, spray, etc.). Where infection is to be accomplished by direct application of a viral genome to a plant, any available technique can be used to prepare the genome. For example, many viruses that can be used have ssRNA genomes. ssRNA can be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that ssRNA vectors often will be prepared by in vitro transcription, particularly with T7 or SP6 polymerase.

In some embodiments, rather than introducing a single viral vector type into a plant, multiple different viral vectors can be introduced. Such vectors can, for example, trans-complement each other with respect to functions such as replication, cell-to-cell movement, and/or long distance movement. Vectors can contain different polynucleotides encoding influenza antigens. Selection for plant(s) or portions thereof that express multiple polypeptides encoding one or more influenza antigen(s) can be performed as described above for single polynucleotides or polypeptides.

Plant Tissue Expression Systems:

As discussed above, influenza antigens can be produced in any suitable system. Vector constructs and expression systems are well known in the art and can be adapted to incorporate use of influenza antigens provided herein. For example, transgenic plant production is known and generation of constructs and plant production can be adapted according to known techniques in the art. In some embodiments, transient expression systems in plants are desired. Two of these systems include production of clonal roots and clonal plant systems, and derivatives thereof, as well as production of sprouted seedlings systems.

Sprouts and Sprouted Seedling Plant Expression Systems:

Systems and reagents for generating a variety of sprouts and sprouted seedlings which are useful for production of influenza antigen(s) have been described previously and are known in the art (see, for example, PCT Publication WO 04/43886, which is incorporated herein by reference). This document further provides sprouted seedlings, which can be edible, as a biomass containing an influenza antigen. In certain aspects, biomass is provided directly for consumption of antigen containing compositions. In some aspects, biomass is processed prior to consumption, for example, by homogenizing, crushing, drying, or extracting. In certain aspects, influenza antigen is purified from biomass and formulated into a pharmaceutical composition.

Additionally provided are methods for producing influenza antigen(s) in sprouted seedlings that can be consumed or harvested live (e.g., sprouts, sprouted seedlings of the *Brassica* genus). In some embodiments, the method can involve growing a seed to an edible sprouted seedling in a contained, regulatable environment (e.g., indoors, in a container, etc.). A seed can be a genetically engineered seed that contains an expression cassette encoding an influenza antigen, which expression is driven by an exogenously inducible promoter. A variety of promoters can be used that are exogenously inducible by, for example, light, heat, phytohormones, or nutrients.

In some embodiments, methods of producing influenza antigen(s) in sprouted seedlings can include first generating a seed stock for a sprouted seedling by transforming plants with an expression cassette that encodes influenza antigen using an *Agrobacterium* transformation system, wherein expression of an influenza antigen is driven by an inducible promoter. Transgenic seeds can be obtained from a transformed plant, grown in a contained, regulatable environment, and induced to express an influenza antigen.

In some embodiments, methods are provided that involves infecting sprouted seedlings with a viral expression cassette encoding an influenza antigen, expression of which can be driven by any of a viral promoter or an inducible promoter. Sprouted seedlings can be grown for two to fourteen days in a contained, regulatable environment or at least until sufficient levels of influenza antigen have been obtained for consumption or harvesting.

This document further provides systems for producing influenza antigen(s) in sprouted seedlings that include a housing unit with climate control and a sprouted seedling containing an expression cassette that encodes one or more influenza antigens, wherein expression is driven by a constitutive or inducible promoter. The systems can provide unique advantages over the outdoor environment or greenhouse, which cannot be controlled. Thus, a grower can precisely time the induction of expression of influenza antigen, which can greatly reduce time and cost of producing influenza antigen(s).

In certain aspects, transiently transfected sprouts contain viral vector sequences encoding an influenza antigen. Seedlings can be grown for a time period so as to allow for production of viral nucleic acid in sprouts, followed by a period of growth wherein multiple copies of virus are produced, thereby resulting in production of influenza antigen(s).

In certain aspects, genetically engineered seeds or embryos that contain a nucleic acid encoding influenza antigen(s) can be grown to sprouted seedling stage in a contained, regulatable environment. The contained, regulatable environment can be a housing unit or room in which seeds can be grown indoors. All environmental factors of a contained, regulatable environment can be controlled. Since sprouts do not require light to grow, and lighting can be expensive, genetically engineered seeds or embryos can be grown to sprouted seedling stage indoors in the absence of light.

Other environmental factors that can be regulated in a contained, regulatable environment include temperature, humidity, water, nutrients, gas (e.g., $O_2$ or $CO_2$ content or air circulation), chemicals (small molecules such as sugars and sugar derivatives or hormones such as such as phytohormones gibberellic or absisic acid, etc.) and the like.

According to certain embodiments, expression of a nucleic acid encoding an influenza antigen can be controlled by an exogenously inducible promoter. Exogenously inducible promoters can be caused to increase or decrease expression of a nucleic acid in response to an external, rather than an internal stimulus. A number of environmental factors can act as inducers for expression of nucleic acids carried by expression cassettes of genetically engineered sprouts. A promoter can be a heat-inducible promoter, such as a heat-shock promoter. For example, using as heat-shock promoter, temperature of a contained environment can simply be raised to induce expression of a nucleic acid. Other promoters include light inducible promoters. Light-inducible promoters can be maintained as constitutive promoters if light in a contained regulatable environment is always on. Alternatively or additionally, expression of a nucleic acid can be turned on at a particular time during development by simply turning on the light. A promoter can be a chemically inducible promoter is used to induce expression of a nucleic acid. According to these embodiments, a chemical could simply be misted or sprayed onto seed, embryo, or seedling to induce expression of nucleic acid. Spraying and misting can be precisely controlled and directed onto target seed, embryo, or seedling to which it is intended. The contained environment is devoid of wind or air currents, which could disperse chemical away from intended target, so that the chemical stays on the target for which it was intended.

Time of expression can be induced can be selected to maximize expression of an influenza antigen in sprouted seedling by the time of harvest. Inducing expression in an embryo at a particular stage of growth, for example, inducing expression in an embryo at a particular number of days after germination, can result in maximum synthesis of an influenza antigen at the time of harvest. For example, inducing expression from the promoter 4 days after germination can result in more protein synthesis than inducing expression from the promoter after 3 days or after 5 days. Those skilled in the art will appreciate that maximizing expression can be achieved by routine experimentation. In some embodiments, sprouted seedlings can be harvested at about 1, 2, 3, 4, 5, 6, 7, 8, 9, 10, 11, 12, 13, 14, 15, 16, 17, 18, 19, 20, 21, 28, or more than 28 days after germination. In some embodiments, sprouted seedlings can be harvested at about In cases where the expression vector has a constitutive promoter instead of an inducible promoter, sprouted seedling may be harvested at a certain time after transformation of sprouted seedling. For example, if a sprouted seedling were virally transformed at an early stage of development, for example, at embryo stage, sprouted seedlings may be harvested at a time when expression is at its maximum post-transformation, e.g., at up to about 1 day, up to about 2 days, up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, up to about 30 days post-transformation. It could be that sprouts develop one, two, three or more months post-transformation, depending on germination of seed.

Generally, once expression of influenza antigen(s) begins, seeds, embryos, or sprouted seedlings can be allowed to grow until sufficient levels of influenza antigen(s) are expressed. In certain aspects, sufficient levels can be levels that would provide a therapeutic benefit to a patient if harvested biomass were eaten raw. Alternatively or additionally, sufficient levels can be levels from which influenza antigen can be concentrated or purified from biomass and formulated into a pharmaceutical composition that provides a therapeutic benefit to a patient upon administration. Typically, influenza antigen is not a protein expressed in sprouted seedling in nature. At any rate, influenza antigen is typically expressed at concentrations above that which would be present in a sprouted seedling in nature.

Once expression of influenza antigen is induced, growth is allowed to continue until sprouted seedling stage, at which time sprouted seedlings can be harvested. Sprouted seedlings can be harvested live. Harvesting live sprouted seedlings has several advantages including minimal effort and breakage. Sprouted seedlings can be grown hydroponically, making harvesting a simple matter of lifting the sprouted seedling from its hydroponic solution. No soil is required for growth of the sprouted seedlings, but may be provided if deemed necessary or desirable by the skilled artisan. Because sprouts can be grown without soil, no cleansing of sprouted seedling material is required at the time of harvest. Being able to harvest the sprouted seedling directly from its hydroponic environment without washing or scrubbing minimizes breakage of the harvested material. Breakage and wilting of plants induces apoptosis. During apoptosis, certain proteolytic enzymes become active, which can degrade pharmaceutical protein expressed in the sprouted seedling, resulting in decreased therapeutic activity of the protein. Apoptosis-induced proteolysis can significantly decrease yield of protein from mature plants. Using methods as described herein, apoptosis can be avoided when no harvesting takes place until the moment proteins are extracted from the plant.

For example, live sprouts can be ground, crushed, or blended to produce a slurry of sprouted seedling biomass, in a buffer containing protease inhibitors. Buffer can be maintained at about 4° C. In some aspects, sprouted seedling biomass is air-dried, spray dried, frozen, or freeze-dried. As in mature plants, some of these methods, such as air-drying, can result in a loss of activity of pharmaceutical protein. However, because sprouted seedlings are very small and have a large surface area to volume ratio, this is much less likely to occur. Those skilled in the art will appreciate that many techniques for harvesting biomass that minimize proteolysis of expressed protein are available and could be applied.

In some embodiments, sprouted seedlings can be edible. In certain embodiments, sprouted seedlings expressing sufficient levels of influenza antigens can be consumed upon harvesting (e.g., immediately after harvest, within minimal period following harvest) so that absolutely no processing occurs before sprouted seedlings are consumed. In this way, any harvest-induced proteolytic breakdown of influenza antigen before administration of influenza antigen to a patient in need of treatment is minimized. For example, sprouted seedlings that are ready to be consumed can be delivered directly to a patient. Alternatively or additionally, genetically engineered seeds or embryos can be delivered to a patient in need of treatment and grown to sprouted seedling stage by a patient. In one aspect, a supply of genetically engineered sprouted seedlings is provided to a patient, or to a doctor who will be treating patients, so that a continual stock of sprouted seedlings expressing certain desirable influenza antigens can be cultivated. This can be particularly valuable for populations in developing countries, where expensive pharmaceuticals are not affordable or deliverable. The ease with which sprouted seedlings can be grown makes sprouted seedlings particularly desirable for such developing populations.

The regulatable nature of the contained environment imparts advantages over growing plants in the outdoor environment. In general, growing genetically engineered sprouted seedlings that express pharmaceutical proteins in plants provides a pharmaceutical product faster (because plants can be harvested younger) and with less effort, risk, and regulatory considerations than growing genetically engineered plants. The contained, regulatable environment can reduce or eliminate risk of cross-pollinating plants in nature.

For example, a heat inducible promoter likely would not be used outdoors because outdoor temperature cannot be controlled. The promoter would be turned on any time outdoor temperature rose above a certain level. Similarly, the promoter would be turned off every time outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as outdoors. Growth of genetically engineered plants in a greenhouse is quite costly. In contrast, in the present system, every variable can be controlled so that the maximum amount of expression can be achieved with every harvest.

In certain embodiments, sprouted seedlings can be grown in trays that can be watered, sprayed, or misted at any time during development of sprouted seedling. For example, a tray can be fitted with one or more watering, spraying, misting, and draining apparatus that can deliver and/or remove water, nutrients, chemicals etc. at specific time and at precise quantities during development of a sprouted seedling. For example, seeds require sufficient moisture to keep them damp. Excess moisture drains through holes in trays into drains in the floor of the room. Typically, drainage water is treated as appropriate for removal of harmful chemicals before discharge back into the environment.

Another advantage of trays is that they can be contained within a very small space. Since no light is required for sprouted seedlings to grow, trays containing seeds, embryos, or sprouted seedlings can be tightly stacked vertically on top of one another, providing a large quantity of biomass per unit floor space in a housing facility constructed specifically for these purposes. In addition, stacks of trays can be arranged in horizontal rows within the housing unit. Once seedlings have grown to a stage appropriate for harvest (about two to fourteen days) individual seedling trays can be moved into a processing facility, either manually or by automatic means, such as a conveyor belt.

The system is unique in that it provides a sprouted seedling biomass, which is a source of an influenza antigen(s). Whether consumed directly or processed into the form of a pharmaceutical composition, because sprouted seedlings can be grown in a contained, regulatable environment, sprouted seedling biomass and/or pharmaceutical composition derived from biomass can be provided to a consumer at low cost. In addition, the fact that the conditions for growth of the sprouted seedlings can be controlled makes the quality and purity of product consistent. The contained, regulatable environment can obviate many safety regulations of the EPA that can prevent scientists from growing genetically engineered agricultural products outdoors.

Transformed Sprouts:

A variety of methods can be used to transform plant cells and produce genetically engineered sprouted seedlings. Two available methods for transformation of plants that require that transgenic plant cell lines be generated in vitro, followed by regeneration of cell lines into whole plants include *Agrobacterium tumefaciens* mediated gene transfer and microprojectile bombardment or electroporation. Viral transformation is a more rapid and less costly method of transforming embryos and sprouted seedlings that can be harvested without an experimental or generational lag prior to obtaining desired product. For any of these techniques, the skilled artisan would appreciate how to adjust and optimize transformation protocols that have traditionally been used for plants, seeds, embryos, or spouted seedlings.

*Agrobacterium* Transformation Expression Cassettes:

*Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines can be produced by the *Agrobacterium* and catabolized by the plant. The bacterial genes responsible for expression of opines are a convenient source of control elements for chimeric expression cassettes. In some cases, an *Agrobacterium* transformation system can be used to generate edible sprouted seedlings, which can be merely harvested earlier than mature plants. *Agrobacterium* transformation methods can easily be applied to regenerate sprouted seedlings expressing influenza antigens.

In general, transforming plants involves transformation of plant cells grown in tissue culture by co-cultivation with an *Agrobacterium tumefaciens* carrying a plant/bacterial vector. The vector contains a gene encoding an influenza antigen. The *Agrobacterium* transfers vector to plant host cell and is then eliminated using antibiotic treatment. Transformed plant cells expressing influenza antigen can be selected, differentiated, and finally regenerated into complete plantlets (Hellens et al. (2000) *Plant Mol. Biol.* 42:819; Pilon-Smits et al. (1999) *Plant Physiolog.* 119:123; Barfield et al. (1991) *Plant Cell Reports* 10:308; and Riva et al. (1998) *J. Biotech.* 1(3).

Expression vectors can include a gene (or expression cassette) encoding an influenza antigen designed for operation in plants, with companion sequences upstream and downstream of the expression cassette. The companion sequences generally can be of plasmid or viral origin and provide necessary characteristics to the vector to transfer DNA from bacteria to the desired plant host.

The basic bacterial/plant vector construct can provide a broad host range prokaryote replication origin, a prokaryote selectable marker. Suitable prokaryotic selectable markers include resistance toward antibiotics such as ampicillin or tetracycline. Other DNA sequences encoding additional functions that are well known in the art can be present in the vector.

*Agrobacterium* T-DNA sequences are required for *Agrobacterium* mediated transfer of DNA to the plant chromosome. The tumor-inducing genes of T-DNA typically are removed and replaced with sequences encoding an influenza antigen. T-DNA border sequences can be retained because they initiate integration of the T-DNA region into the plant genome. If expression of influenza antigen is not readily amenable to detection, the bacterial/plant vector construct can include a selectable marker gene suitable for determining if a plant cell has been transformed, e.g., a nptII kanamycin resistance gene. On the same or different bacterial/plant vector (Ti plasmid) are Ti sequences. Ti sequences include virulence genes, which encode a set of proteins responsible for excision, transfer and integration of T-DNA into the plant genome (Schell (1987) *Science* 237:1176). Other sequences suitable for permitting integration of heterologous sequence into the plant genome can include transposon sequences, and the like, for homologous recombination.

Certain constructs will include an expression cassette encoding an antigen protein. One, two, or more expression cassettes can be used in a given transformation. The recombinant expression cassette contains, in addition to an influenza antigen encoding sequence, at least the following elements: a promoter region, plant 5' untranslated sequences, initiation codon (depending upon whether or not an expressed gene has its own), and transcription and translation termination sequences. In addition, transcription and translation terminators can be included in expression cassettes or chimeric genes. Signal secretion sequences that allow processing and translocation of a protein, as appropriate, can be included in the expression cassette. A variety of promoters, signal sequences, and transcription and translation terminators are described (see, for example, Lawton et al. (1987) *Plant Mol. Biol.* 9:315; U.S. Pat. No. 5,888,789, incorporated herein by reference). In addition, structural genes for antibiotic resistance are commonly utilized as a selection factor (Fraley et al. (1983) *Proc. Natl. Acad. Sci. USA* 80:4803, incorporated herein by reference). Unique restriction enzyme sites at the 5' and 3' ends of a cassette allow for easy insertion into a pre-existing vector. Other binary vector systems for *Agrobacterium*-mediated transformation, carrying at least one T-DNA border sequence are described in PCT/EP99/07414, incorporated herein by reference.

Regeneration:

Seeds of transformed plants can be harvested, dried, cleaned, and tested for viability and for the presence and expression of a desired gene product. Once this has been determined, seed stock is typically stored under appropriate conditions of temperature, humidity, sanitation, and security to be used when necessary. Whole plants then can be regenerated from cultured protoplasts as described (see, e.g., Evans et al. *Handbook of Plant Cell Cultures*, Vol. 1: MacMillan Publishing Co. New York, 1983; and Vasil (ed.), *Cell Culture and Somatic Cell Genetics of Plants*, Acad. Press, Orlando, Fla., Vol. I, 1984, and Vol. III, 1986, incorporated herein by reference). In certain aspects, plants can be regenerated only to sprouted seedling stage. In some aspects, whole plants can be regenerated to produce seed stocks and sprouted seedlings can be generated from seeds of the seed stock.

All plants from which protoplasts can be isolated and cultured to give whole, regenerated plants can be transformed so that whole plants can be recovered that contain a transferred gene. It is known that practically all plants can be regenerated from cultured cells or tissues, including, but not limited to, all major species of plants that produce edible sprouts. Some suitable plants include *Nicotiana* species such as tobacco, alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, and edible flowers such as sunflower, etc.

Means for regeneration vary from one species of plants to the next. However, those skilled in the art will appreciate that generally a suspension of transformed protoplasts containing copies of a heterologous gene is first provided. Callus tissue is formed and shoots can be induced from callus and subsequently rooted. Alternatively or additionally, embryo formation can be induced from a protoplast suspension. These embryos germinate as natural embryos to form plants. Steeping seed in water or spraying seed with water to increase the moisture content of the seed to between 35-45% initiates germination. For germination to proceed, seeds typically can be maintained in air saturated with water under controlled temperature and airflow conditions. The culture media will generally contain various amino acids and hormones, such as auxin and cytokinins. It is advantageous to add glutamic acid and proline to the medium, especially for such species as alfalfa. Shoots and roots normally develop simultaneously. Efficient regeneration will depend on the medium, the genotype, and the history of the culture. If these three variables can be controlled, then regeneration is fully reproducible and repeatable.

The mature plants, grown from transformed plant cells, can be selfed and non-segregating, homozygous transgenic plants can be identified. An inbred plant can produce seeds containing antigen-encoding sequences. Such seeds can be germinated and grown to sprouted seedling stage to produce influenza antigen(s).

In related embodiments, seeds can be formed into seed products and sold with instructions on how to grow seedlings to the appropriate sprouted seedling stage for administration or harvesting into a pharmaceutical composition. In some embodiments, hybrids or novel varieties embodying desired traits can be developed from inbred plants.

Direct Integration:

Direct integration of DNA fragments into the genome of plant cells by microprojectile bombardment or electroporation can be used (see, e.g., Kikkert et al. (1999) *In Vitro Cellular & Developmental Biology. Plant: Journal of the Tissue Culture Association* 35:43; and Bates (1994) *Mol. Biotech.* 2:135). More particularly, vectors that express influenza antigen(s) can be introduced into plant cells by a variety of techniques. As described above, vectors can include selectable markers for use in plant cells. Vectors can include sequences that allow their selection and propagation in a secondary host, such as sequences containing an origin of replication and selectable marker. Typically, secondary hosts include bacteria and yeast. In one embodiment, a secondary host is bacteria (e.g., *Escherichia coli*, the origin of replication is a colE1-type origin of replication) and a selectable marker is a gene encoding ampicillin resistance. Such sequences are well known in the art and are commercially available (e.g., Clontech, Palo Alto, Calif. or Stratagene, La Jolla, Calif.).

Vectors can be modified to intermediate plant transformation plasmids that contain a region of homology to an *Agrobacterium tumefaciens* vector, a T-DNA border region from *Agrobacterium tumefaciens*, and antigen encoding nucleic acids or expression cassettes described above. Further vectors can include a disarmed plant tumor inducing plasmid of *Agrobacterium tumefaciens.*

Direct transformation of vectors can involve microinjecting vectors directly into plant cells by use of micropipettes to mechanically transfer recombinant DNA (see, e.g., Crossway (1985) *Mol. Gen. Genet.* 202:179). Genetic material can be transferred into a plant cell using polyethylene glycols (see, e.g., Krens et al. (1982) *Nature* 296:72). Another method of introducing nucleic acids into plants via high velocity ballistic penetration by small particles with a nucleic acid either within the matrix of small beads or particles, or on the surface (see, e.g., Klein et al. (1987) *Nature* 327:70; and Knudsen et al. (1991) *Planta* 185:330). Yet another method of introduction is fusion of protoplasts with other entities, either minicells, cells, lysosomes, or other fusible lipid-surfaced bodies (see, e.g., Fraley et al. (1982) *Proc. Natl. Acad. Sci. USA* 79:1859). Vectors can be introduced into plant cells by, for example, electroporation (see, e.g., Fromm et al. (1985) *Proc. Natl. Acad. Sci. USA* 82:5824). According to this technique, plant protoplasts can be electroporate in the presence of plasmids containing a gene construct. Electrical impulses of high field strength reversibly permeabilize biomembranes allowing introduction of plasmids. Electroporated plant protoplasts reform the cell wall divide and form plant callus, which can be regenerated to form sprouted seedlings. Those skilled in the art will appreciate how to utilize these methods to transform plants cells that can be used to generate edible sprouted seedlings.

Viral Transformation:

Similar to conventional expression systems, plant viral vectors can be used to produce full-length proteins, including full length antigen. Plant virus vectors can be used to infect and produce antigen(s) in seeds, embryos, sprouted seedlings, etc. Viral system that can be used to express everything from short peptides to large complex proteins. Specifically, using tobamoviral vectors is described (see, for example, McCormick et al. (1999) *Proc. Natl. Acad. Sci. USA* 96:703; Kumagai et al. (2000) *Gene* 245:169; and Verch et al. (1998) *J. Immunol. Methods* 220:69). Thus, plant viral vectors have a demonstrated ability to express short peptides as well as large complex proteins.

In certain embodiments, transgenic sprouts, which express influenza antigen, can be generated utilizing a host/virus system. Transgenic sprouts produced by viral infection provide a source of transgenic protein that has already been demonstrated to be safe. For example, sprouts are free of contamination with animal pathogens. In addition, a virus/sprout system offers a much simpler, less expensive route for scale-up and manufacturing, since transgenes can be introduced into virus, which can be grown up to a commercial scale within a few days. In contrast, transgenic plants can require up to 5-7 years before sufficient seeds or plant material is available for large-scale trials or commercialization.

Plant RNA viruses can have certain advantages that make them attractive as vectors for foreign protein expression. The molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once infectious virus material enters a susceptible host cell, it replicates to high levels and spreads rapidly throughout the entire sprouted seedling (one to ten days post inoculation). Virus particles are easily and economically recovered from infected sprouted seedling tissue. Viruses have a wide host range, enabling use of a single construct for infection of several susceptible species. These characteristics are readily transferable to sprouts.

Foreign sequences can be expressed from plant RNA viruses, typically by replacing one of viral genes with desired sequence, by inserting foreign sequences into the virus genome at an appropriate position, or by fusing foreign peptides to structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (AlMV), and chimeras thereof.

TMV, the prototype of tobamoviruses, has a genome consisting of a single plus-sense RNA encapsidated with a 17.0 kD CP, which results in rod-shaped particles (300 nm in length). CP is the only structural protein of TMV and is required for encapsidation and long distance movement of virus in an infected host (Saito et al. (1990) *Virology* 176: 329). 183 and 126 kD proteins are translated from genomic RNA and are required for virus replication (Ishikawa et al. (1986) *Nucleic Acids Res.* 14:8291). 30 kD protein is the cell-to-cell movement protein of virus (Meshi et al. (1987) *EMBO J.* 6:2557). Movement and coat proteins are translated from subgenomic mRNAs (Hunter et al. (1976) *Nature* 260: 759; Bruening et al. (1976) *Virology* 71:498; and Beachy et al. (1976) *Virology* 73:498; each of which is incorporated herein by reference).

Other methods of transforming plant tissues include transforming the flower of the plant. Transformation of *Arabidopsis thaliana* can be achieved by dipping plant flowers into a solution of *Agrobacterium tumefaciens* (Curtis et al. (2001) *Transgenic Research* 10:363; Qing et al. (2000) *Molecular Breeding: New Strategies in Plant Improvement* 1:67). Transformed plants can be formed in the population of seeds generated by "dipped" plants. At a specific point during flower development, a pore exists in the ovary wall through which *Agrobacterium tumefaciens* gains access to the interior of the ovary. Once inside the ovary, the *Agrobacterium tumefaciens* proliferates and transforms individual ovules (Desfeux et al. (2000) *Plant Physiol.* 123:895). Transformed ovules follow the typical pathway of seed formation within the ovary.

Production and Isolation of Antigen:

In general, standard methods known in the art can be used for culturing or growing plants, plant cells, and/or plant tissues (e.g., clonal plants, clonal plant cells, leaves, sprouts, and sprouted seedlings) for production of antigen(s). A wide variety of culture media and bioreactors have been employed to culture hairy root cells, root cell lines, and plant cells (see, for example, Giri et al. (2000) *Biotechnol. Adv.* 18:1; Rao et al. (2002) *Biotechnol. Adv.* 20:101; and references in both of the foregoing, all of which are incorporated herein by reference. Clonal plants can be grown in any suitable manner.

In some embodiments, an influenza antigen can be expressed in a plant or portion thereof. Proteins can be isolated and purified in accordance with conventional conditions and techniques known in the art. These include methods such as extraction, precipitation, chromatography, affinity chromatography, electrophoresis, and the like. This document provides for purification and affordable scaling up of production of influenza antigen(s) using any of a variety of plant expression systems known in the art and provided herein, including viral plant expression systems described herein.

In some embodiments, it can be desirable to isolate influenza antigen(s) for generation of antibody products and/or desirable to isolate influenza antibody or antigen binding fragment produced. Where a protein is produced from plant tissue(s) or a portion thereof, e.g., roots, root cells, plants, plant cells, that express them, methods described in further detail herein, or any applicable methods known in the art can be used for any of partial or complete isolation from plant material. Where it is desirable to isolate the expression product from some or all of plant cells or tissues that express it, any available purification techniques can be employed. Those of ordinary skill in the art are familiar with a wide range of fractionation and separation procedures (see, for example, Scopes et al., *Protein Purification: Principles and Practice*, 3$^{rd}$ Ed., Janson et al., 1993; *Protein Purification: Principles, High Resolution Methods, and Applications*, Wiley-VCH, 1998; Springer-Verlag, NY, 1993; and Roe, *Protein Purification Techniques*, Oxford University Press, 2001; each of which is incorporated herein by reference). In some embodiments, it can be desirable to render the product more than about 50%, 60%, 70%, 80%, 85%, 90%, 91%, 92%, 93%, 94%, 95%, 96%, 97%, 98%, or 99% pure. See, e.g., U.S. Pat. Nos. 6,740,740 and 6,841,659 for discussion of certain methods useful for purifying substances from plant tissues or fluids.

Those skilled in the art will appreciate that a method of obtaining desired influenza antigen(s) product(s) is by extraction. Plant material (e.g., roots, leaves, etc.) can be extracted to remove desired products from residual biomass, thereby increasing the concentration and purity of product. Plants can be extracted in a buffered solution. For example, plant material can be transferred into an amount of ice-cold water at a ratio of one to one by weight that has been buffered with, e.g., phosphate buffer. Protease inhibitors can be added as required. Plant material can be disrupted by vigorous blending or grinding while suspended in buffer solution and extracted biomass removed by filtration or centrifugation. The product carried in solution can be further purified by additional steps or converted to a dry powder by freeze-drying or precipitation. Extraction can be carried out by pressing. Plants or roots can be extracted by pressing in a press or by being crushed as they are passed through closely spaced rollers. Fluids expressed from crushed plants or roots are collected and processed according to methods well known in the art. Extraction by pressing allows release of products in a more concentrated form. However, overall yield of product may be lower than if product were extracted in solution.

Antibodies

This document provides anti-influenza neuraminidase antibodies that can be used, for example, for therapeutic and/or prophylactic purposes, such as treatment of influenza infection. In some embodiments, anti-influenza antibodies can be produced by plant(s) or portions thereof (e.g., roots, cells, sprouts, or cell line), using materials and methods described herein, for example. In some cases, influenza antibodies can be expressed in plants, plant cells, and/or plant tissues (e.g., sprouts, sprouted seedlings, leaves, roots, root culture, clonal cells, clonal cell lines, and clonal plants), and can be used directly from plant or partially purified or purified in preparation for pharmaceutical administration to a subject.

Monoclonal Antibodies:

Various methods for generating monoclonal antibodies (mAbs) are well known in the art. See, e.g., the methods described in U.S. Pat. No. 4,196,265, incorporated herein by reference. The most standard monoclonal antibody generation techniques generally begin along the same lines as those for preparing polyclonal antibodies (*Antibodies: A Laboratory Manual*, Cold Spring Harbor Laboratory, 1988, which is hereby incorporated by reference). Typically, a suitable animal can be immunized with a selected immunogen to stimulate antibody-producing cells. Rodents such as mice and rats are exemplary animals, although rabbits, sheep, frogs, and chickens also can be used. Mice can be particularly useful (e.g., BALB/c mice are routinely used and generally give a higher percentage of stable fusions).

Following immunization, somatic cells with the potential for producing the desired antibodies, specifically B lymphocytes (B cells), can be selected for use in MAb generation and fusion with cells of an immortal myeloma cell, generally one of the same species as the animal that was immunized. Myeloma cell lines suited for use in hybridoma-producing fusion procedures typically are non-antibody-producing, have high fusion efficiency, and enzyme deficiencies that render then incapable of growing in certain selective media which support the growth of only the desired fused cells (hybridomas). Any one of a number of myeloma cells can be used, as are known to those of skill in the art. For example, where the immunized animal is a mouse, one can use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one can use R210.RCY3, Y3-Ag 1.2.3, IR983F, 4B210 or one of the above listed mouse cell lines. U-266, GM1500-GRG2, LICR-LON-HMy2 and UC729-6, all can be useful in connection with human cell fusions.

This culturing can provide a population of hybridomas from which specific hybridomas can be selected, followed by serial dilution and cloning into individual antibody producing lines, which can be propagated indefinitely for production of antibody.

MAbs produced generally can be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

As described in the Examples below, the 2B9 anti-N1NA monoclonal antibody has a light chain amino acid sequence as set forth in SEQ ID NO:5 and a heavy chain amino acid sequence as set forth in SEQ ID NO:6. The variable region of the light chain is encoded by amino acids 1-127 of SEQ ID NO:5, and the variable region of the heavy chain is encoded by amino acids 1-137 of SEQ ID NO:6. Thus, this document provides an isolated monoclonal antibody that binds neuraminidase, wherein the antibody includes a light chain variable region amino acid sequence as set forth in amino acids 1 to 127 of SEQ ID NO:5, and a heavy chain variable region amino acid sequence as set forth in amino acids 1 to 137 of SEQ ID NO:6, and wherein the antibody has the ability to inhibit neuraminidase enzyme activity. The ability of a particular antibody to inhibit neuraminidase activity can be evaluated using, for example, the methods disclosed in the Examples herein.

Antibody Fragments and Derivatives:

Irrespective of the source of the original antibody against a neuraminidase, either the intact antibody, antibody multimers, or any one of a variety of functional, antigen-binding regions of the antibody can be used. Exemplary functional regions include scFv, Fv, Fab', Fab and F(ab')$_2$ fragments of antibodies. Techniques for preparing such constructs are well known to those in the art and are further exemplified herein.

The choice of antibody construct can be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Antibody fragments can be obtained by proteolysis of the whole immunoglobulin by the non-specific thiolprotease, papain. Papain digestion yields two identical antigen-binding fragments, termed "Fab fragments," each with a single antigen-binding site, and a residual "Fc fragment." The various fractions can be separated by protein A-Sepharose or ion exchange chromatography.

The usual procedure for preparation of F(ab')$_2$ fragments from IgG of rabbit and human origin is limited proteolysis by the enzyme pepsin. Pepsin treatment of intact antibodies yields an F(ab')$_2$ fragment that has two antigen-combining sites and is still capable of cross-linking antigen.

A Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')$_2$ antibody fragments were originally produced as pairs of Fab' fragments that have hinge cysteines between them. Other chemical couplings of antibody fragments are known.

An "Fv" fragment is the minimum antibody fragment that contains a complete antigen-recognition and binding site. This region consists of a dimer of one heavy chain and one light chain variable domain in tight, con-covalent association. It is in this configuration that three hypervariable regions of each variable domain interact to define an antigen-binding site on the surface of the V$_H$-V$_L$ dimer Collectively, six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments (now known as "single chains") comprise the $V_H$ and $V_L$ domains of an antibody, wherein these domains can be present in a single polypeptide chain. Generally, the Fv polypeptide further comprises a polypeptide linker between $V_H$ and $V_L$ domains that enables sFv to form the desired structure for antigen binding.

The following patents are incorporated herein by reference for the purposes of even further supplementing the present teachings regarding the preparation and use of functional, antigen-binding regions of antibodies, including scFv, Fv, Fab', Fab and F(ab')$_2$ fragments of antibodies: U.S. Pat. Nos. 5,855,866; 5,877,289; 5,965,132; 6,093,399; 6,261,535; and 6,004,555. WO 98/45331 is also incorporated herein by reference for purposes including even further describing and teaching the preparation of variable, hypervariable and complementarity determining (CDR) regions of antibodies.

"Diabodies" are small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between two domains on the same chain, the domains can be forced to pair with the complementary domains of another chain and create two antigen-binding sites. Diabodies are described in EP 404,097 and WO 93/11161, each of which is incorporated herein by reference. "Linear antibodies," which can be bispecific or monospecific, comprise a pair of tandem Fd segments ($V_H$-$C_H$1-$V_H$-$C_H$1) that form a pair of antigen binding regions, as described (see, for example, Zapata et al. (1995) Prot. Eng. 8:1057, incorporated herein by reference).

In using a Fab' or antigen binding fragment of an antibody, with the attendant benefits on tissue penetration, one can derive additional advantages from modifying the fragment to increase its half-life. A variety of techniques can be employed, such as manipulation or modification of the antibody molecule itself, and conjugation to inert carriers. Any conjugation for the sole purpose of increasing half-life, rather than to deliver an agent to a target, should be approached carefully in that Fab' and other fragments can be chosen to penetrate tissues. Nonetheless, conjugation to non-protein polymers, such PEG and the like, is contemplated.

Modifications other than conjugation therefore are based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either N-terminal or C-terminal, or both, which is generally used to prolong half-life of biological molecules. By way of example only, one may wish to modify termini by acylation or amination.

Bispecific Antibodies:

Bispecific antibodies in general can be employed, so long as one arm binds to an aminophospholipid or anionic phospholipid and the bispecific antibody is attached, at a site distinct from the antigen binding site, to a therapeutic agent.

In general, the preparation of bispecific antibodies is well known in the art. One method involves the separate preparation of antibodies having specificity for the aminophospholipid or anionic phospholipid, on the one hand, and a therapeutic agent on the other. Peptic F(ab')$_2$ fragments can be prepared from two chosen antibodies, followed by reduction of each to provide separate Fab'$_{SH}$ fragments. SH groups on one of two partners to be coupled then can be alkylated with a cross-linking reagent such as O-phenylenedimaleimide to provide free maleimide groups on one partner. This partner then can be conjugated to the other by means of a thioether linkage, to give the desired F(ab')$_2$ heteroconjugate. Other techniques are known wherein cross-linking with SPDP or protein A is carried out, or a trispecific construct is prepared.

One method for producing bispecific antibodies is by the fusion of two hybridomas to form a quadroma. As used herein, the term "quadroma" is used to describe the productive fusion of two B cell hybridomas. Using now standard techniques, two antibody producing hybridomas can be fused to give daughter cells, and those cells that have maintained the expression of both sets of clonotype immunoglobulin genes then can be selected.

CDR Technologies:

Antibodies are comprised of variable and constant regions. The term "variable," as used herein in reference to antibodies, means that certain portions of the variable domains differ extensively in sequence among antibodies, and are used in the binding and specificity of each particular antibody to its particular antigen. However, the variability is concentrated in three segments termed "hypervariable regions," both in the light chain and the heavy chain variable domains.

The more highly conserved portions of variable domains are called the framework region (FR). Variable domains of native heavy and light chains each comprise four FRs (FR1, FR2, FR3 and FR4, respectively), largely adopting a beta-sheet configuration, connected by three hypervariable regions, which form loops connecting, and in some cases, forming part of, the beta-sheet structure.

The hypervariable regions in each chain are held together in close proximity by the FRs and, with hypervariable regions from the other chain, contribute to the formation of the antigen-binding site of antibodies (Kabat et al. (1991), *Sequences of proteins of immunological interest,* 5th ed. Bethesda, Md.: National Institutes of Health, incorporated herein by reference). Constant domains are not involved directly in binding an antibody to an antigen, but exhibit various effector functions, such as participation of the antibody in antibody-dependent cellular toxicity.

The term "hypervariable region," as used herein, refers to amino acid residues of an antibody that are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-56 (H2) and 95-102 (H3) in the heavy chain variable domain; Kabat et al. (1991), supra) and/or those residues from a "hypervariable loop" (i.e. residues 26-32 (L1), 50-52(L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

The DNA and deduced amino acid sequences of Vh and V kappa chains of the 2B9 antibody encompass CDR1-3 of variable regions of heavy and light chains of the antibody. In light of the sequence and other information provided herein, and the knowledge in the art, a range of 2B9-like and improved antibodies and antigen binding regions can now be prepared and are thus encompassed herein.

In some embodiments, this document provides at least one CDR of the antibody produced by the hybridoma 2B9. In some embodiments, this document provides a CDR, antibody, or antigen binding region thereof, which binds to at least a neuraminidase, and which comprises at least one CDR of the antibody produced by the hybridoma 2B9.

In a particular embodiment, this document provides an antibody or antigen binding region thereof in which the framework regions of the 2B9 antibody have been changed from mouse to a human IgG, such as human IgG1 or other IgG subclass to reduce immunogenicity in humans. In some embodiments, sequences of the 2B9 antibody can be examined for the presence of T-cell epitopes, as is known in the art. The underlying sequence can then be changed to remove T-cell epitopes, i.e., to "deimmunize" the antibody.

The availability of DNA and amino acid sequences of Vh and V kappa chains of the 2B9 antibody means that a range of antibodies can now be prepared using CDR technologies. In particular, random mutations can be made in the CDRs and products screened to identify antibodies with higher affinities and/or higher specificities. Such mutagenesis and selection is routinely practiced in the antibody arts. These methods can be particularly suitable for use in the methods described herein, given the advantageous screening techniques disclosed herein. A convenient way for generating such substitutional variants is affinity maturation using phage display.

CDR shuffling and implantation technologies can be used with the 2B9 antibodies provided herein, for example. CDR shuffling inserts CDR sequences into a specific framework region (Jirholt et al. (1998) *Gene* 215:471, incorporated herein by reference). CDR implantation techniques permit random combination of CDR sequences into a single master framework (Soderlind et al. (1999) *Immunotechnol.* 4:279; and Soderlind et al. (2000) *Nature Biotechnol.* 18:852, each incorporated herein by reference). Using such techniques, CDR sequences of the 2B9 antibody, for example, can be mutagenized to create a plurality of different sequences, which can be incorporated into a scaffold sequence and the resultant antibody variants screened for desired characteristics, e.g., higher affinity.

Antibodies from Phagemid Libraries:

Recombinant technology allows for preparation of antibodies having a desired specificity from recombinant genes encoding a range of antibodies. Certain recombinant techniques involve isolation of antibody genes by immunological screening of combinatorial immunoglobulin phage expression libraries prepared from RNA isolated from spleen of an immunized animal (Morrison et al. (1986) *Mt. Sinai J. Med.* 53:175; Winter and Milstein (1991) *Nature* 349:293; Barbas et al. (1992) *Proc. Natl. Acad. Sci. USA* 89:4457; each incorporated herein by reference). For such methods, combinatorial immunoglobulin phagemid libraries can be prepared from RNA isolated from spleen of an immunized animal, and phagemids expressing appropriate antibodies can be selected by panning using cells expressing antigen and control cells. Advantage of this approach over conventional hybridoma techniques include approximately $10^4$ times as many antibodies can be produced and screened in a single round, and that new specificities can be generated by H and L chain combination, which can further increase the percentage of appropriate antibodies generated.

One method for the generation of a large repertoire of diverse antibody molecules in bacteria utilizes the bacteriophage lambda as the vector (Huse et al. (1989) *Science* 246:1275; incorporated herein by reference). Production of antibodies using the lambda vector involves the cloning of heavy and light chain populations of DNA sequences into separate starting vectors. Vectors subsequently can be randomly combined to form a single vector that directs co-expression of heavy and light chains to form antibody fragments. The general technique for filamentous phage display is described (U.S. Pat. No. 5,658,727, incorporated herein by reference). In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate a gene that encodes the member from the library. Additional methods for screening phagemid libraries are described (U.S. Pat. Nos. 5,580,717; 5,427,908; 5,403,484; and 5,223,409, each incorporated herein by reference).

One method for the generation and screening of large libraries of wholly or partially synthetic antibody combining sites, or paratopes, utilizes display vectors derived from filamentous phage such as M13, fl or fd (U.S. Pat. No. 5,698,426, incorporated herein by reference). Filamentous phage display vectors, referred to as "phagemids," yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al. (1991) *Proc. Natl. Acad. Sci. USA* 88:4363; and Barbas et al. (1991) *Proc. Natl. Acad. Sci. USA* 88:7978; each incorporated herein by reference). The surface expression library is screened for specific Fab fragments that bind neuraminidase molecules by standard affinity isolation procedures. The selected Fab fragments can be characterized by sequencing the nucleic acids encoding the polypeptides after amplification of the phage population.

One method for producing diverse libraries of antibodies and screening for desirable binding specificities is described (U.S. Pat. Nos. 5,667,988 and 5,759,817, each incorporated herein by reference). The method involves the preparation of libraries of heterodimeric immunoglobulin molecules in the form of phagemid libraries using degenerate oligonucleotides and primer extension reactions to incorporate degeneracies into CDR regions of immunoglobulin variable heavy and light chain variable domains, and display of mutagenized polypeptides on the surface of the phagemid. Thereafter, the display protein is screened for the ability to bind to a preselected antigen. A further variation of this method for producing diverse libraries of antibodies and screening for desirable binding specificities is described U.S. Pat. No. 5,702,892, incorporated herein by reference). In this method, only heavy chain sequences are employed, heavy chain sequences are randomized at all nucleotide positions that encode either the CDR1 or CDRIII hypervariable region, and the genetic variability in the CDRs can be generated independent of any biological process.

Transgenic Mice Containing Human Antibody Libraries:

Recombinant technology is available for the preparation of antibodies. In addition to the combinatorial immunoglobulin phage expression libraries disclosed above, one molecular cloning approach is to prepare antibodies from transgenic mice containing human antibody libraries. Such techniques are described (U.S. Pat. No. 5,545,807, incorporated herein by reference).

In a most general sense, these methods involve the production of a transgenic animal that has inserted into its germline genetic material that encodes for at least part of an immunoglobulin of human origin or that can rearrange to encode a repertoire of immunoglobulins. The inserted genetic material can be produced from a human source, or can be produced synthetically. The material can code for at least part of a known immunoglobulin or can be modified to code for at least part of an altered immunoglobulin.

The inserted genetic material is expressed in the transgenic animal, resulting in production of an immunoglobulin derived at least in part from the inserted human immunoglobulin genetic material. The inserted genetic material can be in the form of DNA cloned into prokaryotic vectors such as plasmids and/or cosmids. Larger DNA fragments can be inserted using yeast artificial chromosome vectors (Burke et al. (1987) *Science* 236:806; incorporated herein by reference), or by introduction of chromosome fragments. The inserted genetic material can be introduced to the host in conventional manner, for example by injection or other procedures into fertilized eggs or embryonic stem cells.

Once a suitable transgenic animal has been prepared, the animal is simply immunized with the desired immunogen. Depending on the nature of the inserted material, the animal can produce a chimeric immunoglobulin, e.g. of mixed mouse/human origin, where the genetic material of foreign origin encodes only part of the immunoglobulin; or the animal can produce an entirely foreign immunoglobulin, e.g. of wholly human origin, where the genetic material of foreign origin encodes an entire immunoglobulin.

Polyclonal antisera can be produced from the transgenic animal following immunization. Immunoglobulin-producing cells can be removed from the animal to produce the immunoglobulin of interest. Generally, monoclonal antibodies can be produced from the transgenic animal, e.g., by fusing spleen cells from the animal with myeloma cells and screening the resulting hybridomas to select those producing the desired antibody. Suitable techniques for such processes are described herein.

In one approach, the genetic material can be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg can develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals can be employed to produce human antibodies of a single isotype, more specifically an isotype that is essential for B cell maturation, such as IgM and possibly IgD. Another method for producing human antibodies is described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes.

In the method described in U.S. Pat. Nos. 5,545,806; 5,569,825; 5,625,126; 5,633,425; 5,661,016; and 5,770,429, human immunoglobulin transgenes contained within a transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Humanized Antibodies:

Human antibodies generally have at least three potential advantages for use in human therapy. First, because the effector portion is human, it can interact better with other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, half-life in human circulation will be similar to naturally occurring human antibodies, allowing smaller and less frequent doses to be given.

Various methods for preparing human antibodies are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" antibody are well known to those of skill in the art.

A number of methods have been described to produce humanized antibodies. Controlled rearrangement of antibody domains joined through protein disulfide bonds to form new, artificial protein molecules or "chimeric" antibodies can be utilized (Konieczny et al. (1981) *Haematologia* (Budap.) 14:95; incorporated herein by reference). Recombinant DNA technology can be used to construct gene fusions between DNA sequences encoding mouse antibody variable light and heavy chain domains and human antibody light and heavy chain constant domains (Morrison et al. (1984) *Proc. Natl. Acad. Sci. USA* 81:6851; incorporated herein by reference).

DNA sequences encoding antigen binding portions or complementarity determining regions (CDR's) of murine monoclonal antibodies can be grafted by molecular means into DNA sequences encoding frameworks of human antibody heavy and light chains (Jones et al. (1986) *Nature* 321:522; Riechmann et al. (1988) *Nature* 332:323; each incorporated herein by reference). Expressed recombinant products are called "reshaped" or humanized antibodies, and comprise the framework of a human antibody light or heavy chain and antigen recognition portions, CDR's, of a murine monoclonal antibody.

One method for producing humanized antibodies is described in U.S. Pat. No. 5,639,641, incorporated herein by reference. A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to CDR's, amino acids from the donor immunoglobulin framework that are capable of interacting with CDR's to effect binding affinity, such as one or more amino acids that are immediately adjacent to a CDR in the donor immunoglobulin or those within about 3 Å as predicted by molecular modeling. Heavy and light chains can each be designed by using any one, any combination, or all of various position criteria described in U.S. Pat. Nos. 5,693,762; 5,693,761; 5,585,089; and 5,530,101, each incorporated herein by reference. When combined into an intact antibody, humanized immunoglobulins can be substantially non-immunogenic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries described herein. In a general sense, the method utilizes sequences from the antigen binding site of an antibody or population of antibodies directed against an antigen of interest. Thus for a single rodent antibody, sequences comprising part of the antigen binding site of the antibody can be combined with diverse repertoires of sequences of human antibodies that can, in combination, create a complete antigen binding site.

Antigen binding sites created by this process differ from those created by CDR grafting, in that only the portion of sequence of the original rodent antibody is likely to make contacts with antigen in a similar manner. Selected human sequences are likely to differ in sequence and make alternative contacts with the antigen from those of the original binding site. However, constraints imposed by binding of the portion of original sequence to antigen and shapes of the antigen and its antigen binding sites, are likely to drive new contacts of human sequences to the same region or epitope of the antigen. This process has therefore been termed "epitope imprinted selection," or "EIS."

Starting with an animal antibody, one process results in the selection of antibodies that are partly human antibodies. Such antibodies can be sufficiently similar in sequence to human antibodies to be used directly in therapy or after alteration of a few key residues. In EIS, repertoires of antibody fragments can be displayed on the surface of filamentous phase and genes encoding fragments with antigen binding activities selected by binding of the phage to antigen.

Yet additional methods for humanizing antibodies are described in U.S. Pat. Nos. 5,750,078; 5,502,167; 5,705,154; 5,770,403; 5,698,417; 5,693,493; 5,558,864; 4,935,496; and 4,816,567, each incorporated herein by reference.

As discussed in the above techniques, the advent of methods of molecular biology and recombinant technology, it is now possible to produce antibodies by recombinant means and thereby generate gene sequences that code for specific amino acid sequences found in the polypeptide structure of antibodies. This has permitted the ready production of antibodies having sequences characteristic of inhibitory antibodies from different species and sources, as discussed above. In accordance with the foregoing, the antibodies useful in the methods described herein are anti-neuraminidase antibodies, specifically antibodies whose specificity is toward the same epitope of neuraminidase as 2B9 and include all therapeutically active variants and antigen binding fragments thereof whether produced by recombinant methods or by direct synthesis of the antibody polypeptides.

As described below, the 2B9 anti-N1NA monoclonal antibody was humanized. Two humanized heavy chain sequences (designated "G2" and "G5" herein) are set forth in SEQ ID NOS:9 and 10, respectively. Two humanized light chain sequences (designated "K3" and "K4" herein) are set forth in SEQ ID NOS:11 and 12, respectively.

In some embodiments, an antibody containing variant amino acid sequences with respect to humanized SEQ ID NOS:9-12 can be produced and used in the compositions and methods described herein. In some cases, for example, an antibody as provided herein can include a light chain or a heavy chain having an amino acid sequence with at least 85% (e.g., 85%, 86%, 87%, 88%, 89%, 90%, 91%, 92%, 93%, 94%, 95%, 96%, 97%, 97.5%, 98%, 98.5%, 99.0%, 99.5%, 99.6%, 99.7%, 99.8%, 99.9%, or 100%) sequence identity to the heavy and light chain sequences set forth in SEQ ID NOS:9-12. Thus, this document provides antibodies that bind neuraminidase and that have the ability to inhibit neuraminidase enzyme activity, and wherein the antibody comprises a light chain amino acid sequence that is at least 85 percent (e.g., at least 90 percent, at least 95 percent, at least 96 percent, at least 97 percent, at least 98 percent, or at least 99 percent) identical to the amino acid sequence set forth in SEQ ID NO:9 or SEQ ID NO:10, and a heavy chain amino acid sequence that is at least 85 percent (e.g., at least 90 percent, at least 95 percent, at least 98 percent, or at least 99 percent) identical to the amino acid sequence set forth in SEQ ID NO:7 or SEQ ID NO:8.

Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

Percent sequence identity is determined by comparing a target nucleic acid or amino acid sequence to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site ("fr 'dot' com 'slash' blast") or the U.S. government's National Center for Biotechnology Information web site ("ncbi 'dot' nlm 'dot' nih 'dot' gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq c:\seq1.txt -j c:\seq2.txt -p blastn -o c:\output.txt -q −1 -r 2. If the target sequence shares homology with any portion of the identified sequence, the designated output file will present those regions of homology as aligned sequences. If the target sequence does not share homology with any portion of the identified sequence, the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) a target sequence that is 450 amino acids in length is compared to the sequence set forth in SEQ ID NO:7, (2) the Bl2seq program presents 447 amino acids from the target sequence aligned with a region of the sequence set forth in SEQ ID NO:7 where the first and last amino acids of that 447 amino acid region are matches, and (3) the number of matches over those 447 aligned amino acids is 445, then the 450 amino acid target sequence contains a length of 447 and a percent identity over that length of (i.e., 445) 447×100=99.6%).

The percent identity over the full length of an amino acid sequence is determined by counting the number of matched positions over the entire length of the query sequence (e.g., SEQ ID NO:7), dividing that number by the length of the query sequence, and multiplying by 100. For example, if the Bl2seq program presents 447 amino acids from the 450 amino acid target sequence aligned with and matching the 464 amino acids in the SEQ ID NO:7 query sequence, then the 450 amino acid target sequence is 96.3 percent identical to SEQ ID NO:7 (447/464=96.3%).

It will be appreciated that different regions within a single amino acid or nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Variant antibodies having one or more amino acid substitution relative to the amino acid sequences set forth in SEQ DI NOS:9-12, for example, can be prepared and modified as described herein Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

In some embodiments, an antibody can include one or more non-conservative substitutions. Non-conservative substitutions typically entail exchanging a member of one of the classes described above for a member of another class. Such production can be desirable to provide large quantities or alternative embodiments of such compounds. Whether an amino acid change results in a functional polypeptide can readily be determined by assaying the specific activity of the peptide variant.

Plant Production of Antibodies:

It is to be noted that the materials and methods described herein for expressing antigenic polypeptides in plants also can be used to generate plant-produced antibodies (e.g., the 2B9 monoclonal antibodies described herein). When an antibody is expressed in plants, it is to be understood that the heavy and light chains can be expressed from the same vector, or from two separate vectors. In some embodiments, antibody polypeptides can be produced in a plant using an agrobacterial vector that launches a viral construct (i.e., an RNA with characteristics of a plant virus) encoding the polypeptide of interest. The RNA can have characteristics of (and/or include sequences of), for example, TMV.

A "launch vector" typically contains agrobacterial sequences including replication sequences, and also contains plant viral sequences (including self-replication sequences) that carry a gene encoding a polypeptide of interest. See, e.g., Musiychuk et al. (2006) *Influenza and Other Respiratory Viruses*, Blackwell Publishing Ltd, 1:19-25; incorporated herein by reference). A launch vector can be introduced into plant tissue (e.g., by agroinfiltration), which allows substantially systemic delivery. For transient transformation, non-integrated T-DNA copies of the launch vector remain transiently present in the nucleolus and are transcribed leading to the expression of the carrying genes (Kapila et al. (1997) *Plant Science* 122:101; incorporated herein by reference). *Agrobacterium*-mediated transient expression, differently from viral vectors, cannot lead to the systemic spreading of the expression of the gene of interest. One advantage of this system is the possibility to clone genes larger than 2 kb to generate constructs that would be impossible to obtain with viral vectors (Voinnet et al. (2003) *Plant J.* 33:949; incorporated herein by reference). Furthermore, using such techniques, it is possible to transform a plant with more than one transgene, such that multimeric proteins (e.g., antibodies or subunits of complexed proteins) can be expressed and assembled. Furthermore, the possibility of co-expression of multiple transgenes by means of co-infiltration with different *Agrobacterium* can be taken advantage of, either by separate infiltration or using mixed cultures.

In some embodiments, a launch vector can include sequences that allow for selection (or at least detection) in *Agrobacteria* and also for selection/detection in infiltrated tissues. Furthermore, a launch vector typically includes sequences that are transcribed in the plant to yield viral RNA production, followed by generation of viral proteins. Production of viral proteins and viral RNA can yield rapid production of multiple copies of RNA encoding the pharmaceutically active protein of interest. Such production can result in rapid protein production of the target of interest in a relatively short period of time. Thus, a highly efficient system for protein production can be generated.

The agroinfiltration technique utilizing viral expression vectors can be used to produce limited quantity of protein of interest in order to verify the expression levels before deciding if it is worth generating transgenic plants. Alternatively or additionally, the agroinfiltration technique utilizing viral expression vectors is useful for rapid generation of plants capable of producing huge amounts of protein as a primary production platform. Thus, this transient expression system can be used on industrial scale.

Further provided are any of a variety of different Agrobacterial plasmids, binary plasmids, or derivatives thereof such as pBIV, pBI1221, pGreen, etc., which can be used in the methods provided herein. Numerous suitable vectors are known in the art and can be directed and/or modified according to methods known in the art, or those described herein so as to utilize in the methods described provided herein.

An exemplary launch vector, pBID4, contains the 35S promoter of cauliflower mosaic virus (a DNA plant virus) that drives initial transcription of the recombinant viral genome following introduction into plants, and the nos terminator, the transcriptional terminator of *Agrobacterium* nopaline synthase. The vector further contains sequences of the tobacco mosaic virus genome including genes for virus replication (126/183K) and cell-t-cell movement (MP). The vector further contains a gene encoding a polypeptide of interest, inserted into a unique cloning site within the tobacco mosaic virus genome sequences and under the transcriptional control of the coat protein subgenomic mRNA promoter. Because this "target gene" (i.e., gene encoding a protein or polypeptide of interest) replaces coding sequences for the TMV coat protein, the resultant viral vector is naked self-replicating RNA that is less subject to recombination than CP-containing vectors, and that cannot effectively spread and survive in the environment. Left and right border sequences (LB and RB) delimit the region of the launch vector that is transferred into plant cells following infiltration of plants with recombinant *Agrobacterium* carrying the vector. Upon introduction of *agrobacteria* carrying this vector into plant tissue (typically by agroinfiltration but alternatively by injection or other means), multiple single-stranded DNA (ssDNA) copies of sequence between LB and RB are generated and released in a matter of minutes. These introduced sequences are then amplified by viral replication. Translation of the target gene results in accumulation of large amounts of target protein or polypeptide in a short period of time. A launch vector can include coat proteins and movement protein sequences.

Once produced in a plant, any suitable method can be used to partially or completely isolate an expressed antibody from plant material. As discussed above, a wide range of fractionation and separation procedures are known for purifying substances from plant tissues or fluids. See, also, the methods described in Example 5 herein.

Therapeutic Compositions and Uses Thereof

The antibodies provided herein, as well as plants, plant cells, and plant tissues expressing the antibodies provided herein, can have pharmaceutical activity when administered to a subject in need thereof (e.g., a vertebrate such as a mammal, including mammals such as humans, as well as veterinary animals such as bovines, ovines, canines, and felines). Thus, this document provides therapeutic compositions containing the antibodies, plants, and/or plant tissues and cells described herein. Also provided herein is the use of an antibody, plant, or portion of a plant as described herein in the manufacture of a medicament for treating or preventing influenza infection.

Treatment of a subject with an influenza antibody can elicit a physiological effect. An antibody or antigen binding fragment thereof can have healing curative or palliative properties against a disorder or disease and can be administered to ameliorate relieve, alleviate, delay onset of, reverse or lessen symptoms or severity of a disease or disorder. An antibody composition can have prophylactic properties and can be used to prevent or delay the onset of a disease or to lessen the severity of such disease, disorder, or pathological condition when it does emerge.

The pharmaceutical preparations can be administered in a wide variety of ways to a subject, such as, for example, orally, nasally, enterally, parenterally, intramuscularly or intravenously, rectally, vaginally, topically, ocularly, pulmonarily, or by contact application. In some embodiments, an anti-influenza antibody expressed in a plant, or a portion thereof, can be extracted and/or purified, and used for preparation of a pharmaceutical composition. It may be desirable to formulate such isolated products for their intended use (e.g., as a pharmaceutical agent, antibody composition, etc.). In some embodiments, it will be desirable to formulate products together with some or all of plant tissues that express them. In cases where it is desirable to formulate product together with the plant material, it will often be desirable to have utilized a plant that is not toxic to the relevant recipient (e.g., a human or other animal). Relevant plant tissue (e.g., cells, roots, leaves) can simply be harvested and processed according to techniques known in the art, with due consideration to maintaining activity of the expressed product.

An antibody or antigen binding fragment thereof (i.e., an anti-influenza antibody or antigen binding fragment thereof) can be formulated according to known techniques. For example, an effective amount of an antibody product can be formulated together with one or more organic or inorganic, liquid or solid, pharmaceutically suitable carrier materials. An antibody or antigen binding fragment thereof can be employed in dosage forms such as tablets, capsules, troches, dispersions, suspensions, solutions, gelcaps, pills, caplets, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

In general, compositions can comprise any of a variety of different pharmaceutically acceptable carrier(s) or vehicle(s), or a combination of one or more such carrier(s) or vehicle(s). As used herein the language "pharmaceutically acceptable carrier, adjuvant, or vehicle" includes solvents, dispersion media, coatings, antibacterial and antifungal agents, isotonic and absorption delaying agents, and the like, compatible with pharmaceutical administration. Materials that can serve as pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening agents, flavoring agents, and perfuming agents, preservatives, and antioxidants can be present in the composition, according to the judgment of the formulator (see also *Remington's Pharmaceutical Sciences*, Fifteenth Edition, E. W. Martin, Mack Publishing Co., Easton, Pa., 1975). For example, antibody or antigen binding fragment product can be provided as a pharmaceutical composition by means of conventional mixing granulating dragee-making, dissolving, lyophilizing, or similar processes.

Additional Components:

Compositions can include additionally any suitable components to enhance the effectiveness of the composition when administered to a subject. In certain situations, it can be desirable to prolong the effect of an antibody or antigen binding fragment thereof by slowing the absorption of one or more components of the antibody product (e.g., protein) that is subcutaneously or intramuscularly injected. This can be accomplished by use of a liquid suspension of crystalline or amorphous material with poor water solubility. The rate of absorption of product then depends upon its rate of dissolution, which in turn, can depend upon size and form. Alternatively or additionally, delayed absorption of a parenterally administered product is accomplished by dissolving or suspending the product in an oil vehicle. Injectable depot forms are made by forming microcapsule matrices of protein in biodegradable polymers such as polylactide-polyglycolide. Depending upon the ratio of product to polymer and the nature of the particular polymer employed, rate of release can be controlled. Examples of biodegradable polymers include poly(orthoesters) and poly(anhydrides). Depot injectable formulations can be prepared by entrapping product in liposomes or microemulsions that are compatible with body tissues.

Enterally administered preparations of antibody can be introduced in solid, semi-solid, suspension or emulsion form and can be compounded with any pharmaceutically acceptable carriers, such as water, suspending agents, and emulsifying agents. In some cases, antibodies can be administered by means of pumps or sustained-release forms, especially when administered as a preventive measure, so as to prevent the development of disease in a subject or to ameliorate or delay an already established disease. Supplementary active compounds, e.g., compounds independently active against the disease or clinical condition to be treated, or compounds that enhance activity of a compound as provided herein, can be incorporated into or administered with compositions. Flavorants and coloring agents can be used.

Root lines, cell lines, plants, extractions, powders, dried preparations and purified protein or nucleic acid products, etc., can be in encapsulated form with or without one or more excipients as noted above. Solid dosage forms such as tablets, dragees, capsules, pills, and granules can be prepared with coatings and shells such as enteric coatings, release controlling coatings and other coatings well known in the pharmaceutical formulating art. In such solid dosage forms active agent can be mixed with at least one inert diluent such as sucrose, lactose or starch. Such dosage forms can comprise, as is normal practice, additional substances other than inert diluents, e.g., tableting lubricants and other tableting aids such as magnesium stearate and microcrystalline cellulose. In the case of capsules, tablets and pills, the dosage forms can comprise buffering agents. They optionally can contain opacifying agents and can be of a composition that they release the active ingredient(s) only, or substantially, in a certain part of the intestinal tract, and/or in a delayed manner. Examples of embedding compositions that can be used include polymeric substances and waxes.

Pharmaceutical compositions can be administered therapeutically or prophylactically. The compositions can be used to treat or prevent a disease. For example, any individual who suffers from a disease or who is at risk of developing a disease can be treated. It will be appreciated that an individual can be considered at risk for developing a disease without having been diagnosed with any symptoms of the disease. For example, if the individual is known to have been, or to be intended to be, in situations with relatively high risk of exposure to influenza infection, that individual will be considered at risk for developing the disease. Similarly, if members of an individual's family or friends have been diagnosed with influenza infection, the individual can be considered to be at risk for developing the disease.

Compositions for rectal or vaginal administration can be suppositories or retention enemas, which can be prepared by mixing the compositions provided herein with suitable non-irritating excipients or carriers such as cocoa butter, polyethylene glycol or a suppository wax which can be solid at ambient temperature but liquid at body temperature and therefore melt in the rectum or vaginal cavity and release the active protein.

Dosage forms for topical, transmucosal or transdermal administration of a composition include ointments, pastes, creams, lotions, gels, powders, solutions, sprays, inhalants or patches. The active agent, or preparation thereof, is admixed under sterile conditions with a pharmaceutically acceptable carrier and any needed preservatives or buffers as can be required. For transmucosal or transdermal administration, penetrants appropriate to the barrier to be permeated can be used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, ointments, salves, gels, or cream formulations as generally known in the art can be used. Ophthalmic formulations, eardrops, and eye drops also are contemplated. Also contemplated is the use of transdermal patches, which have the added advantage of providing controlled delivery of a protein to the body. Such dosage forms can be made by suspending or dispensing the product in the proper medium. Absorption enhancers can be used to increase the flux of the protein across the skin. The rate can be controlled by either providing a rate controlling membrane or by dispersing the protein in a polymer matrix or gel.

This document provides methods for using the antibodies and compositions provided herein to treat or prevent an influenza infection in a subject. Compositions can be administered in such amounts and for such time as is necessary to achieve the desired result. In some embodiments, a "therapeutically effective amount" of a pharmaceutical composition is that amount effective for treating, attenuating, or preventing a disease in a subject. Thus, the "amount effective to treat, attenuate, or prevent disease," as used herein, refers to a nontoxic but sufficient amount of the pharmaceutical composition to treat, attenuate, or prevent disease in any subject. For example, the "therapeutically effective amount" can be an amount to treat, attenuate, or prevent infection (e.g., viral infection, influenza infection), etc.

The exact amount required can vary from subject to subject, depending on the species, age, and general condition of the subject, the stage of the disease, the particular pharmaceutical mixture, its mode of administration, and the like. Influenza antibodies, including plants expressing antibodies and/or preparations thereof can be formulated in dosage unit form for ease of administration and uniformity of dosage. The expression "dosage unit form," as used herein, refers to a physically discrete unit of composition appropriate for the patient to be treated. It will be understood, however, that the total daily usage of the compositions typically is decided by an attending physician within the scope of sound medical judgment. The specific therapeutically effective dose level for any particular patient or organism can depend upon a variety of factors including the severity or risk of infection; the activity of the specific compound employed; the specific composition employed; the age, body weight, general health, sex of the patient, diet of the patient, pharmacokinetic condition of the patient, the time of administration, route of administration, and rate of excretion or degradation of the specific antibodies employed; the duration of the treatment; drugs used in combination or coincidental with the composition employed; and like factors well known in the medical arts.

It will be appreciated that the compositions provided herein can be employed in combination therapies (e.g., combination vaccine therapies). That is, pharmaceutical compositions can be administered concurrently with, prior to, or subsequent to, one or more other desired pharmaceutical and/or vaccination procedures. The particular combination of therapies (e.g., vaccines, therapeutic treatment of influenza infection) to employ in a combination regimen will generally take into account compatibility of the desired therapeutics and/or procedures and the desired therapeutic effect to be achieved. It will be appreciated that the therapies and/or vaccines employed can achieve a desired effect for the same disorder (for example, an influenza antibody can be administered concurrently with an antigen), or they can achieve different effects.

In some embodiments, a method as provided herein can include the steps of providing a biological sample (e.g., blood, serum, urine, sputum, tissue scrapings, cerebrospinal fluid, pleural fluid, peritoneal fluid, bladder washings, oral washings, touch preps, or fine-needle aspirates) from a subject (e.g., a human or another mammal), contacting the biological sample with an antibody as described herein (e.g., a 2B9 mAb), and, if the antibody shows detectable binding to the biological sample, administering the antibody to the subject. In some cases, the subject can have been diagnosed as having influenza.

As described in the Examples below, the 2B9 antibody can bind to oseltamivir-resistant influenza strains. Thus, in some embodiments, the antibodies provided herein can be particularly useful for treating strains of influenza that are resistant to oseltamivir. The antibodies also may be useful against zanamivir-resistant influenza strains.

Methods for Typing Influenza Strains

The antibodies provided herein also can be useful in methods for typing influenza strains. For example, the 2B9 antibody binds to NA of the N1 type, but not to N2NA. See, Example 5 below. Thus, an antibody can be used at least to determine whether a particular influenza strain is likely to be an N1 strain.

Articles of Manufacture

This document also provides articles of manufacture that contain anti-influenza antibodies as described herein. The articles of manufacture can be used for diagnostic or therapeutic purposes. In some embodiments, for example, an article can include live sprouted seedlings, clonal entity or plant producing an antibody or antigen binding fragment thereof, or preparations, extracts, or pharmaceutical compositions containing antibody in one or more containers filled with optionally one or more additional ingredients of pharmaceutical compositions. In some embodiments, an article of manufacture can include a therapeutic agent in addition to an anti-influenza antibody (e.g., an influenza vaccine) for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents. In some embodiments, an anti-influenza antibody can be provided in an injectable formulation for administration. In other embodiments, an anti-influenza antibody can be provided in an inhalable formulation for administration. Pharmaceutical doses or instructions therefore can be provided in the kit for administration to an individual suffering from or at risk for influenza infection.

In some embodiments, a kit can be used for diagnosis or virus typing. An antibody can be provided in a kit, and can be used to contact a biological sample from a subject to determine whether that subject has influenza. Further, since an antibody such as 2B9 may to NA of one type but not another type (e.g., may bind to N1NA, but not to N2NA), a kit can be used to determine whether an particular influenza virus is likely to be of a particular strain (e.g., N1 vs. N2).

The invention will be further described in the following examples, which do not limit the scope of the invention described in the claims.

EXAMPLES

Example 1

Generation of Antigen Constructs

Generation of Antigen Sequences from Influenza Virus Neuraminidase:

Nucleotide sequences encoding neuraminidase of influenza virus type Vietnam H5N1 (NAV) were synthesized and confirmed as being correct. The nucleotide and amino acid sequences were as follows.

```
NAV(N1)(nt):
                                        (SEQ ID NO: 3)
GGATCCTTAATTAAAATGGGATTCGTGCTTTTCTCTCAGCTTCCTT

CTTTCCTTCTTGTGTCTACTCTTCTTCTTTTCCTTGTGATTTCTCA

CTCTTGCCGTGCTCAAAATGTCGACCTTATGCTTCAGATTGGAAAC

ATGATTTCTATTTGGGTGTCACACTCTATTCACACTGGAAACCAGC

ATCAGTCTGAGCCAATTTCTAACACTAACCTTTTGACTGAGAAGGC

TGTGGCTTCTGTTAAGTTGGCTGGAAACTCTTCTCTTTGCCCTATT

AACGGATGGGCTGTGTACTCTAAGGATAACTCTATTAGGATTGGAT

CTAAGGGAGATGTGTTCGTGATTAGGGAGCCATTCATTTCTTGCTC

TCACCTTGAGTGCCGTACTTTCTTCCTTACTCAGGGTGCTCTTCTT

AACGATAAGCACTCTAACGGAACTGTGAAGGATAGGTCTCCACACA

GGACTCTTATGTCTTGTCCAGTTGGAGAAGCTCCATCTCCATACAA

CTCTAGATTCGAGTCTGTTGCTTGGAGTGCTTCTGCTTGCCATGAT

GGAACTTCATGGCTTACTATTGGAATTTCTGGACCAGATAACGGAG

CTGTTGCTGTGCTTAAGTACAACGGAATTATTACTGATACCATCAA

GTCTTGGAGGAACAACATTCTTAGGACTCAGGAGTCTGAGTGTGCT

TGCGTTAACGGATCTTGCTTCACTGTGATGACTGATGGACCATCTA

ATGGACAGGCTTCTCACAAGATTTTCAAGATGGAGAAGGGAAAGGT

TGTGAAGTCTGTGGAACTTGATGCTCCAAACTACCATTACGAGGAG

TGTTCTTGCTATCCAGATGCTGGAGAGATTACTTGTGTGTGCCGTG

ATAATTGGCATGGATCTAACAGGCCATGGGTGTCATTCAATCAGAA

CCTTGAGTACCAGATTGGTTACATTTGCTCTGGAGTGTTCGGAGAT

AATCCAAGGCCAAACGATGGAACTGGATCTTGTGGACCAGTGTCAT

CTAATGGAGCTGGAGGAGTGAAGGGATTCTCTTTCAAGTACGAAA

CGGAGTTTGGATTGGAAGGACTAAGTCTACTAACTCTAGGAGTGGA
```

-continued
```
TTCGAGATGATTTGGGACCCAAACGGATGGACTGAGACTGATTCTT

CTTTCTCTGTGAAGCAGGATATTGTGGCTATTACTGATTGGAGTGG

ATACTCTGGATCTTTCGTTCAGCACCCAGAGCTTACTGGACTTGAT

TGCATTAGGCCATGCTTCTGGGTTGAACTTATTAGGGGAAGGCCAA

AGGAGTCTACTATTTGGACTTCTGGATCTTCTATTTCTTTCTGCGG

AGTGAATTCTGATACTGTGGGATGGTCTTGGCCAGATGGAGCTGAG

CTTCCATTCACTATTGATAAGGTCGACCATCATCATCATCACCACA

AGGATGAGCTTTGACTCGAG

NAV(N1) (aa):
                                            (SEQ ID NO: 4)
LMLQIGNMISIWVSHSIHTGNQHQSEPISNTNLLTEKAVASVKLAG

NSSLCPINGWAVYSKDNSIRIGSKGDVFVIREPFISCSHLECRTPF

LTQGALLNDKHSNGTVKDRSPHRTLMSCPVGEAPSPYNSRFESVAW

SASACHDGTSWLTIGISGPDNGAVAVLKYNGIITDTIKSWRNNILR

TQESECACVNGSCFTVMTDGPSNGQASHKIFKMEKGKVVKSVELDA

PNYHYEECSCYPDAGEITCVCRDNWHGSNRPWVSFNQNLEYQIGYI

CSGVFGDNPRPNDGTGSCGPVSSNGAGGVKGFSFKYGNGVWIGRTK

STNSRSGFEMIWDPNGWTETDSSFSVKQDIVAITDWSGYSGSFVQH

PELTGLDCIRPCFWVELIRGRPKESTIWTSGSSISFCGVNSDTVGW

SWPDGAELPFTIDK
```

Example 2

Generation of Antigen Vectors

The NA target antigen constructs were subcloned into the viral vector pBI-D4. pBI-D4 is a pBI121-derived binary vector in which the reporter gene coding for the *Escherichia coli* beta-D-glucuronidase (GUS) is replaced by a "polylinker" where, between the XbaI and SacI sites, a TMV-derived vector is inserted. pBI-D4 is a TMV-based construct in which a foreign gene to be expressed (e.g., target antigen) replaces the coat protein (CP) gene of TMV. The virus retains the TMV 126/183 kDa gene, the movement protein (MP) gene, and the CP subgenomic mRNA promoter (sgp), which extends into the CP open reading frame (ORF). The start codon for CP has been mutated. The virus lacks CP and therefore cannot move throughout the host plant via phloem. However, cell-to-cell movement of viral infection remains functional, and the virus can move slowly to the upper leaves in this manner. A multiple cloning site (PacI-PmeI-AgeI-XhoI) has been engineered at the end of sgp for expression of foreign genes, and is followed by the TMV 3' non-translated region (NTR). The 35S promoter is fused at the 5' end of the viral sequence, the vector sequence is positioned between the BamH1 and Sac1 sites of pBI121, and the hammerhead ribozyme is placed 3' of the viral sequence (Chen et al. (2003) *Mol. Breed.* 11:287).

These constructs were generated to include fusions of sequences encoding NA to sequences encoding the signal peptide from tobacco PR-1a protein, a 6× His tag and the ER-retention anchor sequence KDEL. For constructs containing sequence encoding PR-NA-KDEL, the coding DNA was introduced into pBI-D4 as PacI-XhoI fragments. NAV (NA Vietnam) was introduced directly as a PacI-XhoI fragment into pB1-D4. Nucleotide sequences were subsequently verified spanning the subcloning junctions of the final expression constructs.

Example 3

Generation of Plants and Antigen Production

*Agrobacterium* Infiltration of Plants:
*Agrobacterium*-mediated transient expression system achieved by *Agrobacterium* infiltration was utilized (Turpen et al. (1993) *J. Virol. Methods* 42:227). Healthy leaves of *Nicotiana benthamiana* were infiltrated with *A. rhizogenes* containing viral vectors engineered to express N1NA.

The *A. tumifaciens* strain A4 (ATCC 43057; ATCC, Manassas, Va.) was transformed with the constructs pB1-D4-PR-NA-KDEL and pB1-D4-PR-NA-VAC. *Agrobacterium* cultures were grown and induced as described (Kapila et al. (1997) *Plant Sci.* 122:101). A 2 ml starter-culture (picked from a fresh colony) was grown overnight in YEB (5 g/l beef extract, 1 g/l yeast extract, 5 g/l peptone, 5 g/l sucrose, 2 mM $MgSO_4$) with 25 µg/ml kanamycin at 28° C. The starter culture was diluted 1:500 into 500 ml of YEB with 25 µg/ml kanamycin, 10 mM 2-4(-morpholino)ethanesulfonic acid (MES) pH 5.6, 2 mM additional $MgSO_4$ and 20 µM acetosyringone. The diluted culture was then grown overnight to an $O.D._{600}$ of ~1.7 at 28° C. The cells were centrifuged at 3,000×g for 15 minutes and re-suspended in MMA medium (MS salts, 10 mM MES pH 5.6, 20 g/l sucrose, 200 µM acetosyringone) to an $O.D._{600}$ of 2.4, kept for 1-3 hour at room temperature, and used for *Agrobacterium*-infiltration. *N. benthamiana* leaves were injected with the *Agrobacterium*-suspension using a disposable syringe without a needle. Infiltrated leaves were harvested 6 days post-infiltration. Plants were screened for the presence of target antigen expression by immunoblot analysis. Zymogram analysis revealed the expression of NA proteins in the *N. benthamiana* transgenic roots tested.

Example 4

Production of Antigen 100 mg samples of *N. benthamiana* infiltrated leaf material were harvested at 4, 5, 6 and 7 days post-infection. The fresh tissue was analysed for protein expression right after being harvested or collected at −80° C. for the preparation of subsequent crude plants extracts or for fusion protein purification.

Fresh samples were resuspended in cold PBS 1× plus protease inhibitors (Roche) in a 1/3 w/v ratio (1 ml/0.3 g of tissue) and ground with a pestle. The homogenates were boiled for 5 minutes in SDS gel loading buffer and then clarified by centrifugation for 5 minutes at 12,000 rpm at 4° C. The supernatants were transferred to fresh tubes, and 20 µl, 1 µl, or dilutions thereof were separated by 12% SDS-PAGE and analyzed by Western analysis using anti-$His_6$-HA mouse polyclonal antibodies.

NA expression in *N. benthamiana* plants infiltrated either with *A. tumefaciens* containing the plasmid pBID4-NA-KDEL led to a specific band corresponding to the molecular weight of NA-KDEL. Quantification of NA-KDEL expressed in crude extract was made by immunoblotting both on manually infiltrated tissues and on vacuum-infiltrated tissues.

Purification of Antigens:
Leaves from plants infiltrated with recombinant *A. tumefaciens containing the pBID4-NA-KDEL construct were* ground by homogenization. Extraction buffer with "EDTA-free" protease inhibitors (Roche) and 1% Triton X-100 was used at a ratio of 3× (w/v) and rocked for 30 minutes at 4° C. Extracts were clarified by centrifugation at 9000×g for 10 minutes at 4° C. Supernatants were sequentially filtered through Mira cloth, centrifuged at 20,000×g for 30 minutes at 4° C., and filtered through a 0.45-μm filter before chromatographic purification.

The resulting extracts were cut using ammonium sulfate precipitation. Briefly, $(NH_4)_2SO_4$ was added to 20% saturation, incubated on ice for 1 hour, and spun down at 18,000×g for 15 minutes. Pellets were discarded and $(NH_4)_2SO_4$ was added slowly to 60% saturation, incubated on ice for 1 hour, and spun down at 18,000×g for 15 minutes. Supernatants were discarded and the resulting pellets were resuspended in buffer, maintained on ice for 20 minutes, and centrifuged at 18,000×g for 30 minutes. Supernatants were dialyzed overnight against 10,000 volumes of washing buffer.

His-tagged NA-KDEL proteins were purified using Ni-NTA sepharose ("Chelating Sepharose Fast Flow Column"; Amersham) at room temperature under gravity. The purification was performed under non-denaturing conditions. Proteins were collected as 0.5 ml fractions that were unified, combined with 20 mM EDTA, dialyzed against 1×PBS overnight at 4° C., and analyzed by SDS-PAGE. Alternatively, fractions were collected, unified, combined with 20 mM EDTA, dialyzed against 10 mM $NaH_2PO_4$ overnight at 4° C., and purified by anion exchange chromatography. For NA-KDEL purification, anion exchange column Q Sepharose Fast Flow (Amersham Pharmacia Biosciences) was used. Samples of the NA-KDEL affinity or ion-exchange purified proteins were separated on 12% polyacrylamide gels followed by Coomassie staining.

After dialysis, samples were analyzed by immunoblotting using the mAb α-anti-His$_6$. The His-tag was maintained by the expressed proteins, and the final concentration of the purified protein was determined using GeneTools software from Syngene (Frederick, Md.).

Example 5

Derivation of a Murine Hybridoma Secreting Monoclonal Antibody

A 10 week-old female A/J mouse was injected intraperitoneally with crudely-purified, plant-expressed vaccine material comprised of 50 μg of full-length N1 neuraminidase. Soluble protein was delivered in 300 μl with no adjuvant. Identical doses were given 14 days and 24 days later.

Seventy-two hours after the second boost, 45 million spleen cells were fused with 5 million P3XAg8.653 murine myeloma cells using polyethylene glycol. The resulting 50 million fused cells were plated at 5×10$^5$ cells per well in 10×96 well plates. HAT (hypoxanthine, aminopterin, and thymidine) selection followed 24 hours later and continued until colonies arose. All immunoglobulin-secreting hybridomas were subcloned by three rounds of limiting dilution in the presence of HAT.

Figure 2:
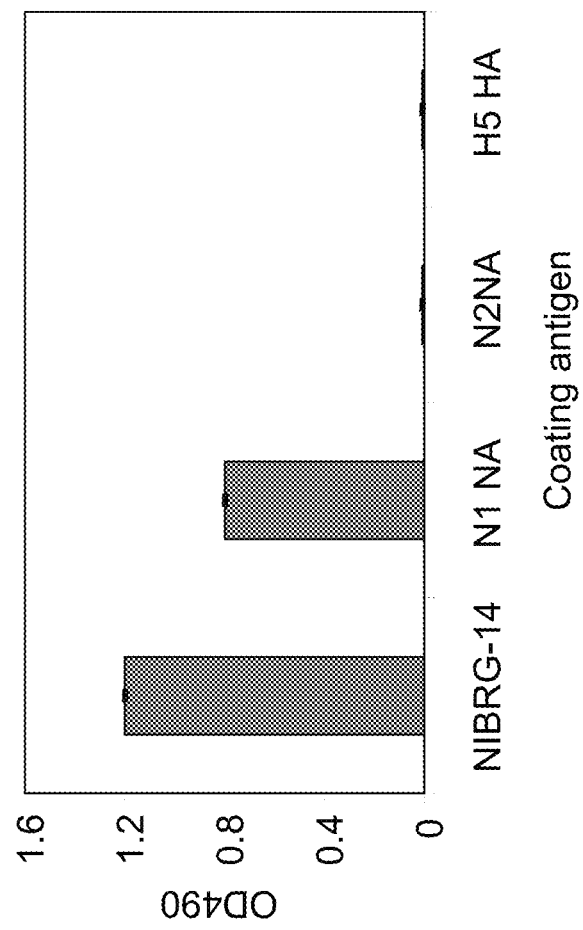
Figure 4:
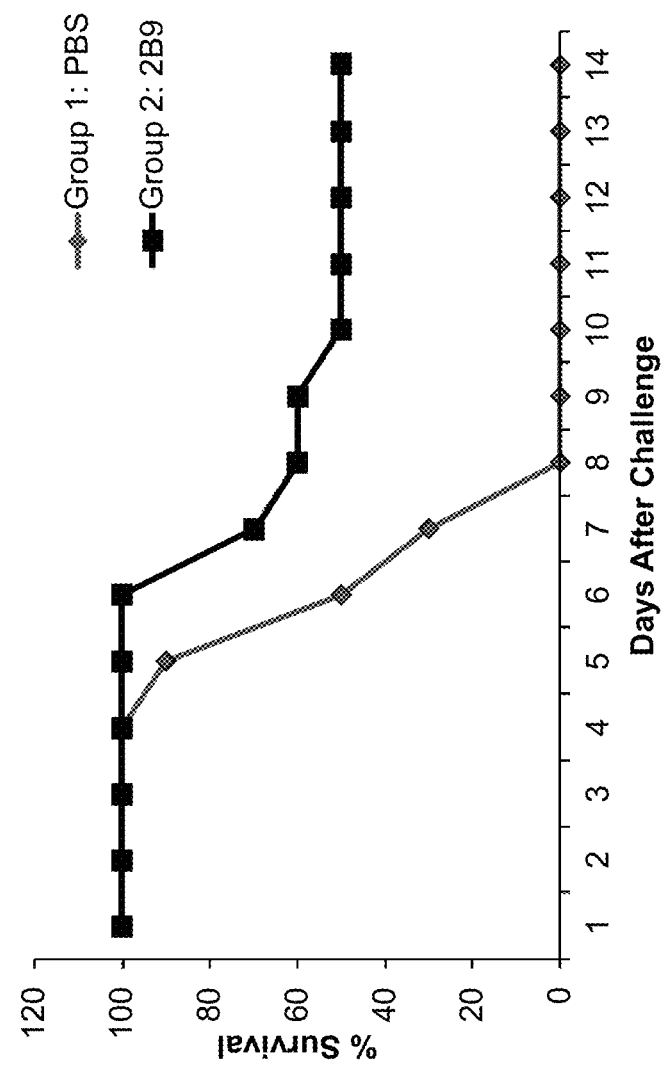

Potential hybridomas were screened on ELISA plates for IgG specific for NIBRG-14, a reverse genetics-derived clone of A/Vietnam/1194/04 (NIBSC, Mill Hill, UK). Hybridoma 2B9 had a very high specific signal. The specificity of this monoclonal antibody was tested further by ELISA against plant-expressed antigens. Supernatant from 10$^6$ cells, cultured for 48 hours in 2.5 ml of Iscoves minimally essential medium supplemented with 10% fetal bovine serum, was strongly reactive against NIBRG-14 and N1 neuraminidase, but not against N2 neuraminidase or H5 hemagglutinin (FIG. 2).

Using an ELISA, the isotype and subclass of the 2B9 anti-N1 monoclonal antibody was determined to be IgG2b'κ.

Example 6

Engineering of mAb 2B9 in Plants

RT-PCR was performed on RNA purified from 2B9 hybridoma cells using a Novagen kit to determine the sequence of variable regions. Specific primers then were designed to clone the full-length antibody light and heavy chain cDNAs. The nucleotide sequences were obtained using an automated sequencer, and were translated to determine amino acid sequences for the light and heavy chains:

```
2B9 light chain sequence:
                                         (SEQ ID NO: 5)
MRFPAQFLGLLLVWLTGARCDIQMTQSPASLSESVGETVTITCRAS

ENIYSYLAWYQQKQGKSPQLLVYFAKTLAEGVPSTFSGSGSGTLFS

LKINSLQPEDFGNYYCQHHYGTPYTFGGGTKLEIKRADAAPTVSIF

PPSSEQLTSGGASVVCFLNNFYPKDINVKWKIDGSERQNGVLNSWT

DQDSKDSTYSMSSTLTLTKDEYERHNSYTCEATHKTSTSPIVKSFN

RNEC

2B9 mAb heavy chain sequence:
                                         (SEQ ID NO: 6)
MGWSWIFLLSVTAGVHSQVQLQQSGAELVRPGTSVKMSCKAAGYTF

TNYWIGWVKQRPGHGLEWIGDIYPENDFSNYNEKFKDKATLTADTS

SRTAYMQLSSLTSEDSAIYYCVRANEGWYLDVWGTGTTVSVSSAKT

TPPSVYPLAPGCGDTTGSSVTLGCLVKGYFPESVTVTWNSGSLSSS

VHTFPALLQSGLYTMSSSVTVPSSTWPSQTVTCSVAHPASSTTVDK

KLEPSGPTSTINPCPPCKECHKCPAPNLEGGPSVFIFPPNIKDVLM

ISLTPKVTCVVVDVSEDDPDVQISWFVNNVEVLTAQTQTHREDYNS

TIRVVSALPIQHQDWMSGKEFKCKVNNKDLPAPIERTISKIKGIVR

APQVYILSPPPEQLSRKDVSLTCLAVGFSPEDISVEWTSNGHTEEN

YKNTAPVLDSDGSYFIYSKLDIKTSKWEKTDSFSCNVRHEGLHSYY

LKKTISRSPGK
```

Example 6

Characterization of Antibody Inhibitory Activity

For characterization of antibody activity, an assay based on the recommended WHO neuraminidase assay protocol was used, with minor modifications. For each assay, reactions were conducted in triplicate and consisted of:

a) 1 μl fresh extract prepared from plant tissue that had been infiltrated with an expression vector encoding neuraminidase (N1) lacking the N-terminal transmembrane domain; to prepare the plant extracts 1 μl of buffer was used for each mg of plant tissue.

b) no antibody (positive control) or a volume of monoclonal antibody (either Ab αN1 [from hybridoma 2B9] or Ab RSV [antibody against viral RSV F protein raised in mouse]), such that the molar ratio of neuraminidase to antibody was 1:1, 1:10, 1:20 or 1:30

It is noted that the neuraminidase antibody and RSV F antibody were of the same isotype (murine IgG2b). Reactions were incubated at room temperature for 30 minutes to give the antibodies the opportunity to recognize the plant-produced neuraminidase. Reactions were then incubated at 37° C., an optimum temperature for neuraminidase activity. Product (sialic acid) accumulation was assessed colorimetrically at 549 nm using a spectrophotometer, and quantified against sialic acid standards.

The percentage of neuraminidase inhibition was calculated using the equation % inhibition=([PC−Tr]/PC)×100, where PC is the neuraminidase activity of the positive control, and Tr is the neuraminidase activity of the antibody/neuraminidase combination.

Figure 3:
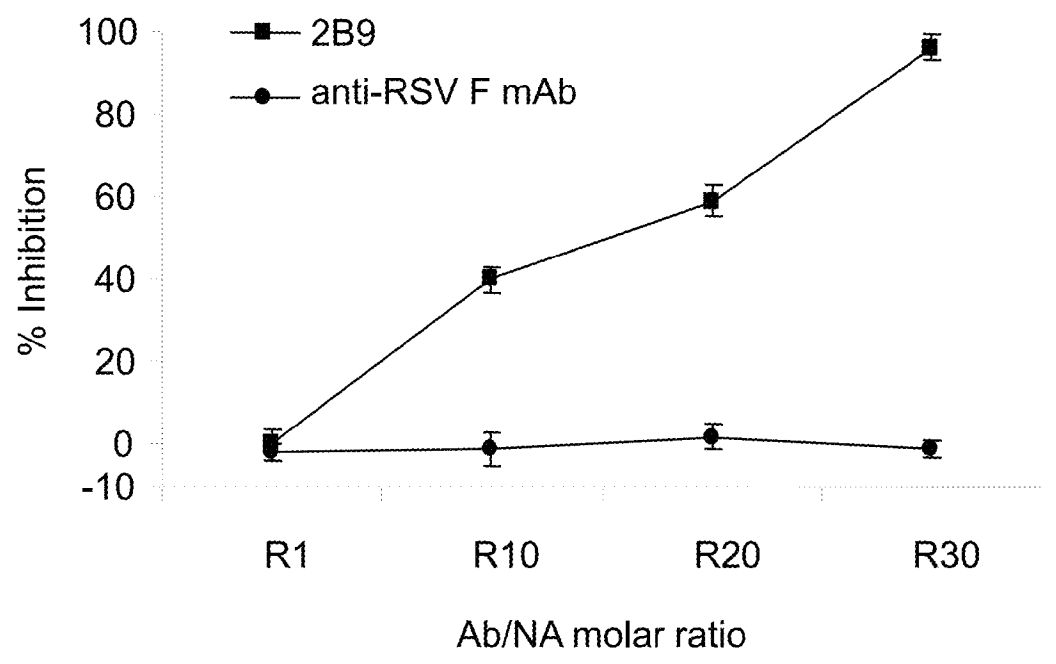

A molar comparison of the antibody's ability to inhibit viral neuraminidase is depicted in FIG. 3. Percent neuraminidase inhibition (calculated according to the equation above) is shown on the y-axis and the molar ratio of neuraminidase to antibody (1:1, 1:10, 1:20 or 1:30) is shown on the x-axis as R1, R10, R20 or R30, respectively. Standard errors are shown for p<0.05.

Inhibition of plant-expressed neuraminidase activity was observed in the presence of the murine monoclonal antibody that was generated against this same plant-expressed neuraminidase. For comparison, the inability of an unrelated (RSV) antibody to inhibit the same plant produced neuraminidase also is shown (FIG. 3).

To determine whether anti-NA 2B9 is capable of recognizing N1 antigens from influenza strains besides the strain from which the 2B9 antigen was originally derived, neuraminidase assays were performed using three different H5N1 strains (A/Vietnam/1203/04, A/Hong Kong/156/97, and A/Indonesia/05), one H1N1 strain (A/New Caldonia/99), and one H3N2 strain (A/Udorn/72). In these experiments, NA inhibition was measured using 2'-(4-Methylumbelliferyl)-α-D-N-acetylneuraminic acid, which liberates a quantifiable fluorescent tag in response to sialidase activity. MDNA has absorption and fluorescence emission maxima of approximately 365 and 450, respectively, and signal can be detected fluorometrically with a sensitivity as low as $10^6$ virus particles/ml ($10^4$ particles total) with a broad linear range of 0-30 fold dilutions of the virus stock. The system used amplified live virus which was diluted to the appropriate concentration in reaction buffer (100 mM sodium acetate, pH 6.5, 10 mM $CaCl_2$) and added directly to plates containing 2-fold serial dilutions of the tested antibody. Because active NA is located on the viral surface, no purification of NA protein was necessary to measure enzymatic activity. The antibody was 2-fold serially-diluted and aliquoted in triplicate into 384 microplate wells. Titrated virus (also diluted in reaction buffer) was added to the plate wells, followed by a 30 minute incubation. MDNA was diluted to 0.2 mM in reaction buffer and added to the plate wells, and the reaction was allowed to proceed for and additional 30 minutes. The reaction was stopped by addition of 200 mM sodium carbonate, pH 9.5.

Titration of each cell-culture amplified virus strain was performed prior to the assay to establish the linear range of NA activity detection. Oseltamivir carboxylate (Tamiflu®, 2 μM) was used as a control drug for this assay. Oseltamivir carboxylate is a specific inhibitor of influenza virus NA activity and is available from the SRI chemical respository.

Antibody dilutions and controls were run in triplicate assays (Table 1). Antibody concentrations from 1-250 μg/ml (final well volume) were tested, and oseltamivir carboxylate (2 μM final well concentration) was included as a positive inhibition control. A summary of the $IC_{50}$ results for each virus strain is presented in Table 1.

TABLE 1

| NA assay $IC_{50}$* results | |
|---|---|
| Virus | Antibody $IC_{50}$ (μg/ml) |
| A/Udorn/72 | N/D** |
| A/NC/99 | 125-250 |
| A/VN/04 | <1 |
| A/HK/97 | 16-33 |
| A/Indo/05 | 4-8 |

*$IC_{50}$ = 50% inhibitory concentration
**N/D = not determined

Example 7

Inhibition of NA from Cross-Clade 2B9

The inhibitory effect of the 2B9 antibody against other influenza strains, including strains resistant to oseltamivir, also was examined Results are presented in Table 2. 2B9 demonstrated the highest level of inhibition against the A/Vietnam/1203/04 virus, and inhibited NA from isolates in different clades, including oseltamivir-resistant strains. The $IC_{50}$ for 2B9 was slightly higher when tested with A/HongKong/156/97, suggesting that 2B9 may inhibit NA from recent H5N1 isolates more efficiently.

TABLE 2

| $IC_{50}$ of 2B9 against various influenza strains | | |
|---|---|---|
| Virus | Oseltamivir | $IC_{50}$* μg/ml |
| H3N2 | S§ | N/D† |
| A/Udorn/72<br>H1N1 | | |
| A/New Caledonia/20/99<br>H5N1<br>Clade 1 | S | 125-250 |
| A/Vietnam/1203/04 | S | ≤1 |
| A/Vietnam/HN/30408/05<br>Clade 2.1 | R | 0.5-1 |
| A/Indoesia/05/05<br>Clade 2.2 | S | 4-8 |
| A/Egypt-2/14724/NAMRU3/06 | R | 1-2 |
| A/Egypt/14725/NAMRU3/06<br>Clade 2.3 | R | 1-2 |
| A/Hong Kong/156/97<br>Clade 3 | S | 16-33 |
| A/duck/Hong Kong/380.5/01 | R | 0.3-0.5 |

*$IC_{50}$, 50% inhibitory concentration
§S, oseltamivir sensitive; R, oseltamivir resistant
†N/D, not determined

Example 8

Mouse Challenge with a/Vn/1203/04

Mice were administered 500 ng of ascites purified 2B9 intravenously for 5 days beginning at 1 hour before challenge with A/VN/1203/04. PBS was used as a control. As shown in FIG. 4, no mice treated with PBS survived more than 8 days, whereas about half of the mice treated with 2B9 were still alive at the 2-week endpoint of the study.

Example 9

Humanized 2B9

The 2B9 heavy and light chain sequences were directly subcloned into a pBI121-based vector, one each for heavy (HC) and light chain (LC). Humanized sequences were obtained from Antitope Ltd. (Cambridge, UK). Sequences were optimized for plant expression by GeneArt, Inc. (Burlingame, Calif.) before being cloned into the pBI121 expression vector.

For transient expression of the 2B9 mAb in plants, *Agrobacterium tumefaciens* strain GV3101 was transformed with appropriate vectors. Bacterial cultures were grown overnight, diluted to $OD_{600}$=0.5, mixed at a ratio of 2:1 (HC:LC), and used in agroinfiltration of *Nicotiana benthamiana* leaves. The leaves were harvested 5 days post-infiltration.

To purify the plant-produced mAb, plant tissue was homogenized in 3 volumes of extraction buffer (50 mM Tris-HCl pH 7.5, 10 mM EDTA) containing 10 mM sodium diethyldithiocarbamate, 0.5% Triton X-100 and centrifuged for 30 minutes at 15,000×g at 4° C. The supernatant was filtered through Miracloth and spun at 75,000×g for 30 minutes, followed by microfiltration through 0.2 μm syringe filters. The antibodies were purified using 5 ml HiTrap MabSelect SuRe column (GE Healthcare, Piscataway, N.J.). The antibody concentration was estimated on Coomassie stained 10% SDS-PAGE gel using whole human IgG (Jackson Immunoresearch Laboratories, West Grove, Pa.) as a standard.

Figure 5:
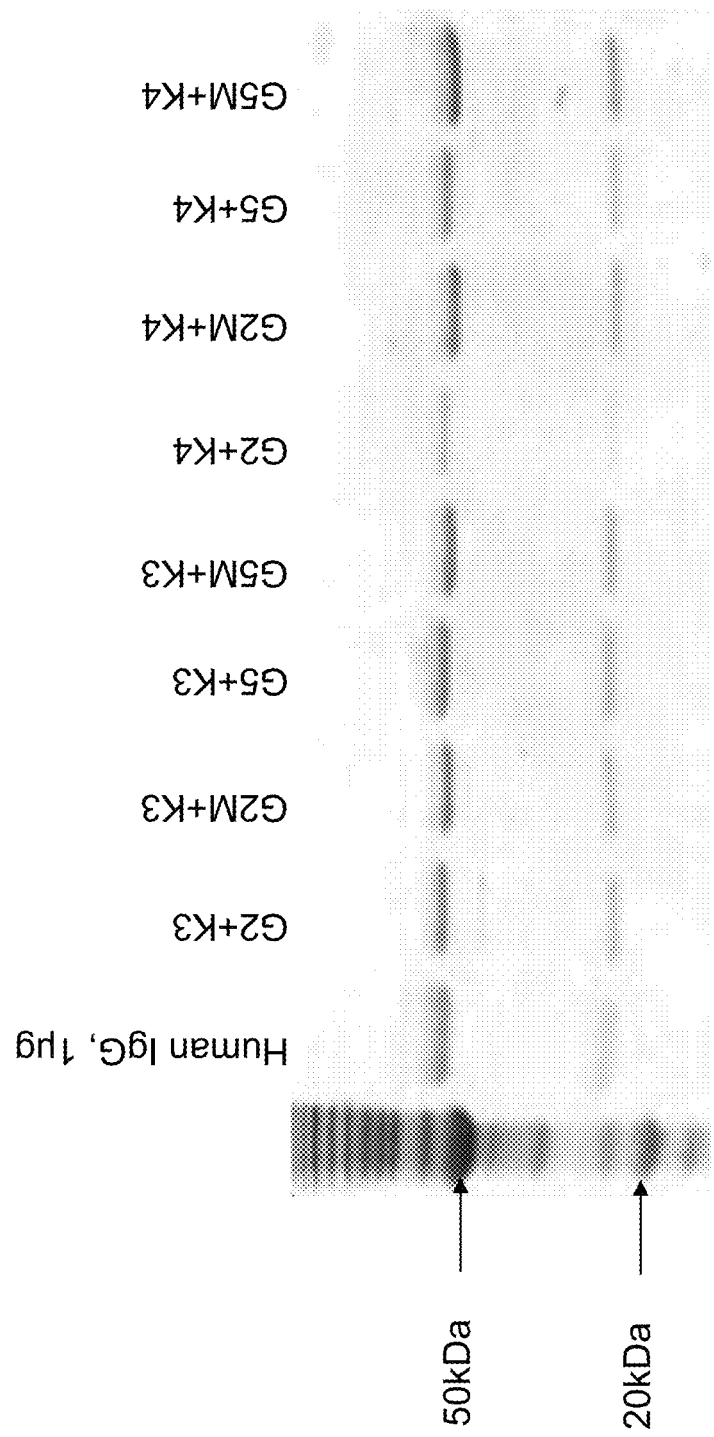

Two humanized light chains and two humanized heavy chains were generated, and were produced in each possible combination, as shown in the gel depicted in FIG. 5. The sequences of the humanized light and heavy chains are shown below.

```
h2B9 heavy chain (G2):
                                      (SEQ ID NO: 7)
MGWSLILLFLVAVATRVHSQVQLVQSGSELKKPGASVKMSCKAAGY

TFTNYWIGWVRQAPGQGLEWIGDIYPENDFSNYNEKFKDRATLTAD

TSTRTAYMELSSLRSEDTAVYYCVRANEGWYLDVWGQGTTVTVSSA

STKGPSVFPLAPCSRSTSESTAALGCLVKDYFPEPVTVSWNSGALT

SGVHTFPAVLQSSGLYSLSSVVTVPSSSLGTKTYTCNVDHKPSNTK

VDKRVESKYGPPCPSCPAPEFLGGPSVFLFPPKPKDTLMISRTPEV

TCVVVDVSQEDPEVQFNWYVDGVEVHNAKTKPREEQFNSTYRVVSV

LTVLHQDWLNGKEYKCKVSNKGLPSSIEKTISKAKGQPREPQVYTL

PPSQEEMTKNQVSLTCLVKGFYPSDIAVEWESNGQPENNYKTTPPV

LDSDGSFFLYSRLTVDKSRWQEGNVFSCSVMHEALHNHYTQKSLSL

SLGK h2B9 heavy chain (G5):
                                      (SEQ ID NO: 8)
MGWSLILLFLVAVATRVHSQVQLVQSGSELKKPGASVKVSCKAAGY

TFTNYWIGWVRQAPGQGLEWIGDIYPENDFSNYNEKFKDRVTITAD

TSTSTAYMELSSLRSEDTAVYYCVRANEGWYLDVWGQGTTVTVSSA

STKGPSVFPLAPCSRSTSESTAALGCLVKDYFPEPVTVSWNSGALT
```

-continued

```
SGVHTFPAVLQSSGLYSLSSVVTVPSSSLGTKTYTCNVDHKPSNTK

VDKRVESKYGPPCPSCPAPEFLGGPSVFLFPPKPKDTLMISRTPEV

TCVVVDVSQEDPEVQFNWYVDGVEVHNAKTKPREEQFNSTYRVVSV

LTVLHQDWLNGKEYKCKVSNKGLPSSIEKTISKAKGQPREPQVYTL

PPSQEEMTKNQVSLTCLVKGFYPSDIAVEWESNGQPENNYKTTPPV

LDSDGSFFLYSRLTVDKSRWQEGNVFSCSVMHEALHNHYTQKSLSL

SLGK h2B9 light chain (K3):
                                      (SEQ ID NO: 9)
MRVPAQLLGLLLLWLPGARCDIQMTQSPSSLSASVGDRVTITCRAS

ENIYSYLAWYQQKPGKAPKLLVYFAKTLAEGVPSRFSGSGSGTEFT

LTISSLQPDDFANYYCQHHYGTPYTFGQGTKLEIKRTVAAPSVFIF

PPSDEQLKSGTASVVCLLNNFYPREAKVQWKVDNALQSGNSQESVT

EQDSKDSTYSLSSTLTLSKADYEKHKVYACEVTHQGLSSPVTKSFN

RGEC h2B9 light chain (K4):
                                     (SEQ ID NO: 10)
MRVPAQLLGLLLLWLPGARCDIQMTQSPSSLSASVGDRVTITCRAS

ENIYSYLAWYQQKPGKAPKLLVYFAKTLAEGVPSRFSGSGSGTEFT

LTISSLQPDDFATYYCQHHYGTPYTFGQGTKLEIKRTVAAPSVFIF

PPSDEQLKSGTASVVCLLNNFYPREAKVQWKVDNALQSGNSQESVT

EQDSKDSTYSLSSTLTLSKADYEKHKVYACEVTHQGLSSPVTKSFN

RGEC
```

In addition, humanized antibodies were generated in which the heavy chain glycosylation sites were mutated. These are designated as "G2M" and "G5M" in FIG. 5, for example.

Figure 6:
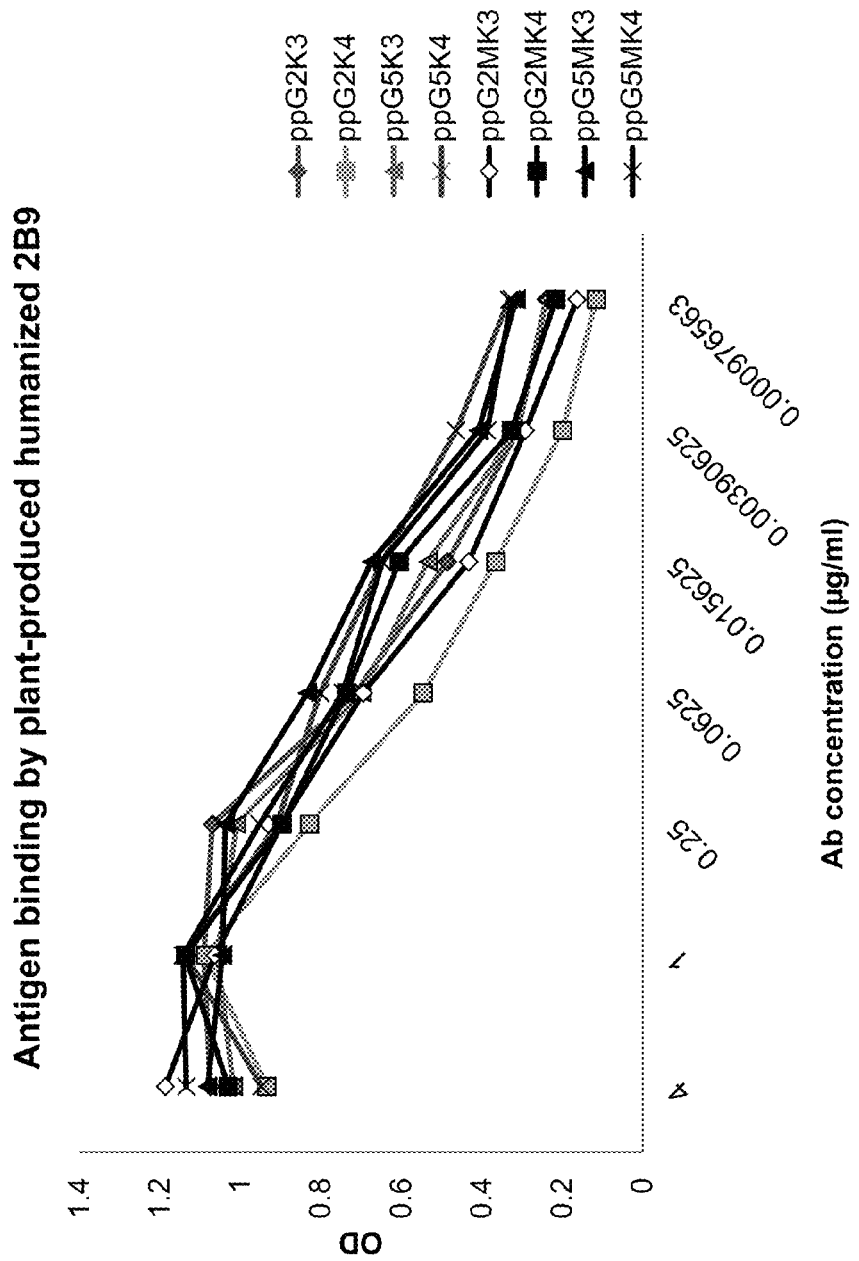

The various humanized 2B9 antibodies were produced in plants and examined by ELISA for antigen binding. As shown in FIG. 6, antibody concentration was correlated directly with antigen binding, although the different combinations of heavy and light humanized chains had somewhat varying antigen binding capabilities. For example, at the lowest concentration studied, antibodies with a mutated glycosylation site in their heavy chain demonstrated greater antigen binding than antibodies without a mutated heavy chain glycosylation site, with the exception of the G5K4 combination.

Experiments also were conducted to measure inhibition of NA activity by humanized 2B9 antibodies produced in plants or in CHO cells. The data presented in Table 3 show the $IC_{50}$ values for the various h2B9 antibodies, as indicated. The $IC_{50}$ of 2B9 from mouse ascites was 0.82 (±0.09) μg/ml.

TABLE 3

Inhibition of NA activity by plant-produced h2B9

| CHO-produced humanized 2B9 | IC$_{50}$ (μg/ml) | Plant-produced humanized 2B9 | IC$_{50}$ (μg/ml) | Plant-produced humanized 2B9 | IC$_{50}$ (μg/ml) |
|---|---|---|---|---|---|
| VH2VK3 | 2.28 | G2K3 | 0.50 (±0.09) | G2MK3 | 0.51 (±0.3) |
| VH2VK4 | 0.42 (±0.16) | G2K4 | 1.16 (±0.17) | G2MK4 | 0.77 (±0.07) |
| VH5VK3 | 0.72 (±0.02) | G5K3 | 0.45 (±0.12) | G5MK3 | 0.54 (±0.05) |
| VH5VK4 | 0.53 (±0.19) | G5K4 | 0.21 (±0.01) | G5MK4 | 0.35 (±0.06) |

Figure 7:
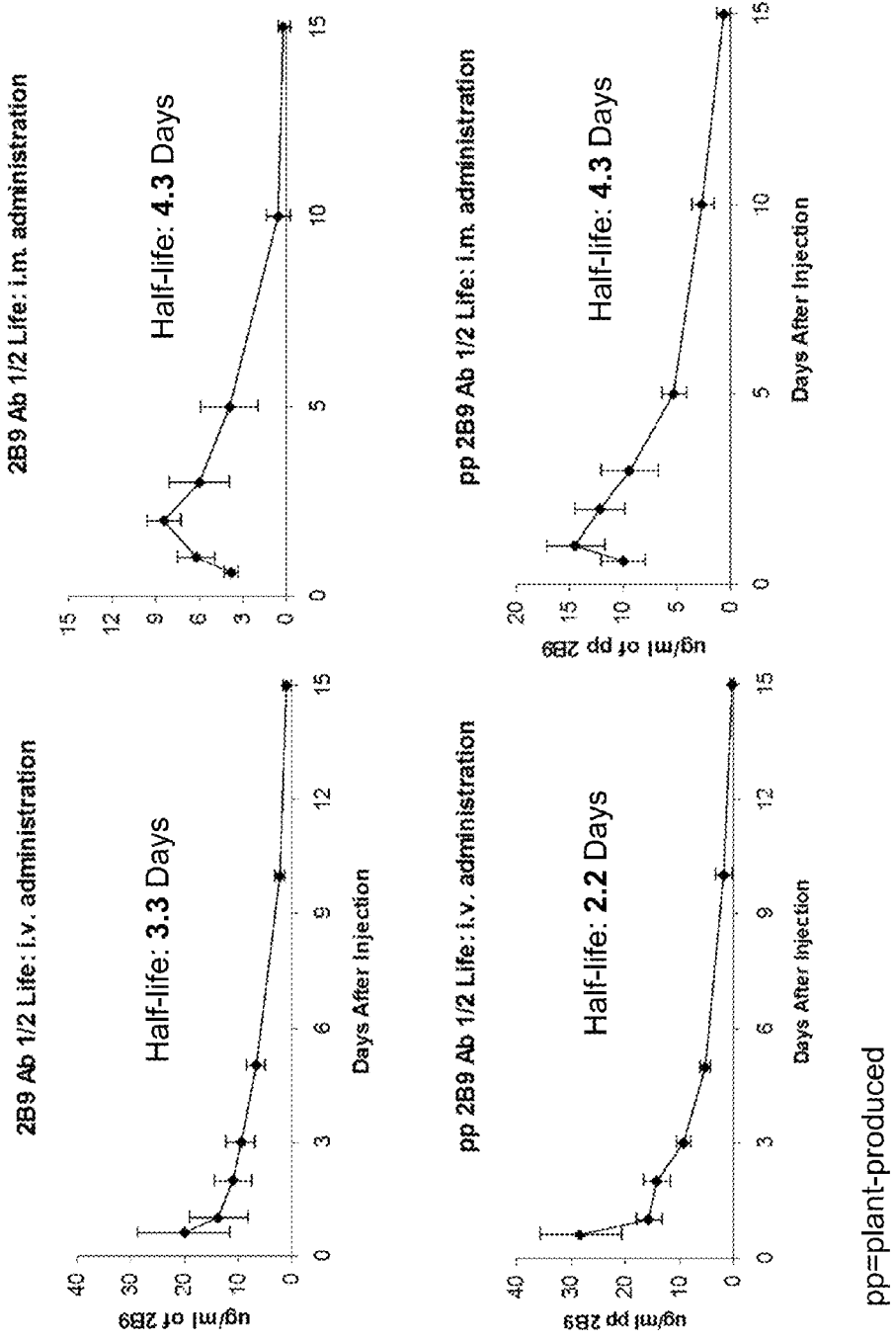

The half life of hybridoma- or plant-produced 2B9 was examined by injecting the antibody into mice either intramuscularly or intravenously. Hybridoma- and plant-produced 2B9 had a half life of 4.3 days when administered intramuscularly (FIG. 7). The half life of the antibody was less when it was administered intravenously, at 3.3 days for the hybridoma-produced version and 2.2 days for the plant preparation.

Taken together, the data presented herein demonstrate that the N1NA-specific monoclonal antibody, 2B9, has broad cross-reactivity to strains of influenza from clades 1, 2, and 3, including drug-resistant strains. 2B9 also provides protection against homologous virus challenge in vivo, and it may be useful for diagnostics and for post- and pre-exposure treatment for influenza. The plant-produced h2B9 antibody had IC$_{50}$ values similar to that of hybridoma-produced 2B9.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All references cited herein are incorporated by reference in their entirety.

What is claimed is:

1. A method for treating an influenza infection in a subject in need thereof, comprising administering to the subject an amount a composition that is effective to reduce symptoms of the influenza infection in the subject, wherein the composition comprises a pharmaceutically acceptable carrier and an antibody that binds neuraminidase, wherein the antibody has the ability to inhibit neuraminidase enzyme activity, and wherein the antibody comprises the light chain amino acid sequence set forth in SEQ ID NO:9 or SEQ ID NO:10, and wherein the antibody comprises the heavy chain amino acid sequence set forth in SEQ ID NO:7 or SEQ ID NO:8.

2. The method of claim 1, wherein the subject is a human patient.

3. The method of claim 2, wherein the human patient is diagnosed as having influenza.

4. The method of claim 3, wherein the human patient is diagnosed as having an oseltamivir-resistant strain of influenza.

* * * * *

```
                        SEQUENCE LISTING

<160> NUMBER OF SEQ ID NOS: 12

<210> SEQ ID NO 1
<211> LENGTH: 449
<212> TYPE: PRT
<213> ORGANISM: Influenza A virus

<400> SEQUENCE: 1

Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Leu Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190
```

```
Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asp Ala Gly Glu Ile Thr Cys Val Cys
                260                 265                 270

Arg Asp Asn Trp His Gly Ser Asn Arg Pro Trp Val Ser Phe Asn Gln
                275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Gly Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
                340                 345                 350

Met Ile Trp Asp Pro Asn Gly Trp Thr Glu Thr Asp Ser Ser Phe Ser
                355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400

Cys Phe Trp Val Glu Leu Ile Arg Gly Arg Pro Lys Glu Ser Thr Ile
                405                 410                 415

Trp Thr Ser Gly Ser Ser Ile Ser Phe Cys Gly Val Asn Ser Asp Thr
                420                 425                 430

Val Gly Trp Ser Trp Pro Asp Gly Ala Glu Leu Pro Phe Thr Ile Asp
                435                 440                 445

Lys

<210> SEQ ID NO 2
<211> LENGTH: 469
<212> TYPE: PRT
<213> ORGANISM: Influenza A virus

<400> SEQUENCE: 2

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
                100                 105                 110
```

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
        130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
            195                 200                 205

Gly Arg Leu Val Asp Ser Ile Val Ser Trp Ser Lys Lys Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
            290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
            355                 360                 365

Lys Leu Arg Ser Gly Tyr Glu Thr Phe Lys Val Ile Glu Gly Trp Ser
            370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
450                 455                 460

Asn Leu Met Pro Ile
465

<210> SEQ ID NO 3
<211> LENGTH: 1446
<212> TYPE: DNA
<213> ORGANISM: Artificial Sequence
<220> FEATURE:
<221> NAME/KEY:
<223> OTHER INFORMATION: synthetic polynucleotide

<400> SEQUENCE: 3

```
ggatccttaa ttaaaatggg attcgtgctt ttctctcagc ttccttcttt ccttcttgtg      60
tctactcttc ttctttttcct tgtgatttct cactcttgcc gtgctcaaaa tgtcgacctt    120
atgcttcaga ttggaaacat gatttctatt tgggtgtcac actctattca cactggaaac    180
cagcatcagt ctgagccaat tctaacact aaccttttga ctgagaaggc tgtggcttct     240
gttaagttgg ctgaaactc ttctctttgc cctattaacg gatgggctgt gtactctaag     300
gataactcta ttaggattgg atctaaggga gatgtgttcg tgattaggga gccattcatt    360
tcttgctctc accttgagtg ccgtactttc ttccttactc agggtgctct tcttaacgat    420
aagcactcta acggaactgt gaaggatagg tctccacaca ggactcttat gtcttgtcca    480
gttggagaag ctccatctcc atacaactct agattcgagt ctgttgcttg gagtgcttct    540
gcttgccatg atggaacttc atggcttact attggaattt ctggaccaga taacggagct    600
gttgctgtgc ttaagtacaa cggaattatt actgatacca tcaagtcttg gaggaacaac    660
attcttagga ctcaggagtc tgagtgtgct tgcgttaacg atcttgctt cactgtgatg     720
actgatggac catctaatgg acaggcttct cacaagattt tcaagatgga aagggaaag    780
gttgtgaagt ctgtggaact tgatgctcca aactaccatt cgaggagtg ttcttgctat     840
ccagatgctg gagagattac ttgtgtgtgc cgtgataatt ggcatggatc taacaggcca    900
tgggtgtcat tcaatcagaa ccttgagtac cagattggtt acatttgctc tggagtgttc    960
ggagataatc caaggccaaa cgatggaact ggatcttgtg gaccagtgtc atctaatgga   1020
gctggaggag tgaagggatt ctcttcaag tacggaaacg gagtttggat tggaaggact    1080
aagtctacta actctaggag tggattcgag atgatttggg acccaaacgg atggactgag   1140
actgattctt ctttctctgt gaagcaggat attgtggcta ttactgattg gagtggatac   1200
tctggatctt tcgttcagca cccagagctt actggacttg attgcattag gccatgcttc   1260
tgggttgaac ttattagggg aaggccaaag gagtctacta tttggacttc tggatcttct   1320
atttctttct gcggagtgaa ttctgatact gtgggatggt cttggccaga tggagctgag   1380
cttccattca ctattgataa ggtcgaccat catcatcatc accacaagga tgagctttga   1440
ctcgag                                                              1446
```

<210> SEQ ID NO 4
<211> LENGTH: 428
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 4

```
Leu Met Leu Gln Ile Gly Asn Met Ile Ser Ile Trp Val Ser His Ser
1               5                   10                  15

Ile His Thr Gly Asn Gln His Gln Ser Glu Pro Ile Ser Asn Thr Asn
            20                  25                  30

Leu Leu Thr Glu Lys Ala Val Ala Ser Val Lys Leu Ala Gly Asn Ser
        35                  40                  45

Ser Leu Cys Pro Ile Asn Gly Trp Ala Val Tyr Ser Lys Asp Asn Ser
    50                  55                  60

Ile Arg Ile Gly Ser Lys Gly Asp Val Phe Val Ile Arg Glu Pro Phe
65                  70                  75                  80

Ile Ser Cys Ser His Leu Glu Cys Arg Thr Phe Phe Leu Thr Gln Gly
```

85                  90                  95
Ala Leu Leu Asn Asp Lys His Ser Asn Gly Thr Val Lys Asp Arg Ser
            100                 105                 110

Pro His Arg Thr Leu Met Ser Cys Pro Val Gly Glu Ala Pro Ser Pro
            115                 120                 125

Tyr Asn Ser Arg Phe Glu Ser Val Ala Trp Ser Ala Ser Ala Cys His
            130                 135                 140

Asp Gly Thr Ser Trp Leu Thr Ile Gly Ile Ser Gly Pro Asp Asn Gly
145                 150                 155                 160

Ala Val Ala Val Leu Lys Tyr Asn Gly Ile Ile Thr Asp Thr Ile Lys
                165                 170                 175

Ser Trp Arg Asn Asn Ile Leu Arg Thr Gln Glu Ser Glu Cys Ala Cys
            180                 185                 190

Val Asn Gly Ser Cys Phe Thr Val Met Thr Asp Gly Pro Ser Asn Gly
            195                 200                 205

Gln Ala Ser His Lys Ile Phe Lys Met Glu Lys Gly Lys Val Val Lys
            210                 215                 220

Ser Val Glu Leu Asp Ala Pro Asn Tyr His Tyr Glu Glu Cys Ser Cys
225                 230                 235                 240

Tyr Pro Asp Ala Gly Glu Ile Thr Cys Val Cys Arg Asp Asn Trp His
                245                 250                 255

Gly Ser Asn Arg Pro Trp Val Ser Phe Asn Gln Asn Leu Glu Tyr Gln
            260                 265                 270

Ile Gly Tyr Ile Cys Ser Gly Val Phe Gly Asp Asn Pro Arg Pro Asn
            275                 280                 285

Asp Gly Thr Gly Ser Cys Gly Pro Val Ser Ser Asn Gly Ala Gly Gly
            290                 295                 300

Val Lys Gly Phe Ser Phe Lys Tyr Gly Asn Gly Val Trp Ile Gly Arg
305                 310                 315                 320

Thr Lys Ser Thr Asn Ser Arg Ser Gly Phe Glu Met Ile Trp Asp Pro
                325                 330                 335

Asn Gly Trp Thr Glu Thr Asp Ser Ser Phe Ser Val Lys Gln Asp Ile
            340                 345                 350

Val Ala Ile Thr Asp Trp Ser Gly Tyr Ser Gly Ser Phe Val Gln His
            355                 360                 365

Pro Glu Leu Thr Gly Leu Asp Cys Ile Arg Pro Cys Phe Trp Val Glu
            370                 375                 380

Leu Ile Arg Gly Arg Pro Lys Glu Ser Thr Ile Trp Thr Ser Gly Ser
385                 390                 395                 400

Ser Ile Ser Phe Cys Gly Val Asn Ser Asp Thr Val Gly Trp Ser Trp
                405                 410                 415

Pro Asp Gly Ala Glu Leu Pro Phe Thr Ile Asp Lys
            420                 425

<210> SEQ ID NO 5
<211> LENGTH: 234
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 5

Met Arg Phe Pro Ala Gln Phe Leu Gly Leu Leu Leu Val Trp Leu Thr
1               5                   10                  15

```
Gly Ala Arg Cys Asp Ile Gln Met Thr Gln Ser Pro Ala Ser Leu Ser
                20                  25                  30

Glu Ser Val Gly Glu Thr Val Thr Ile Thr Cys Arg Ala Ser Glu Asn
            35                  40                  45

Ile Tyr Ser Tyr Leu Ala Trp Tyr Gln Gln Lys Gln Gly Lys Ser Pro
        50                  55                  60

Gln Leu Leu Val Tyr Phe Ala Lys Thr Leu Ala Glu Gly Val Pro Ser
65                  70                  75                  80

Thr Phe Ser Gly Ser Gly Ser Gly Thr Leu Phe Ser Leu Lys Ile Asn
                85                  90                  95

Ser Leu Gln Pro Glu Asp Phe Gly Asn Tyr Tyr Cys Gln His His Tyr
            100                 105                 110

Gly Thr Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 6
<211> LENGTH: 471
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 6

Met Gly Trp Ser Trp Ile Phe Leu Leu Ser Val Thr Ala Gly Val His
1               5                   10                  15

Ser Gln Val Gln Leu Gln Gln Ser Gly Ala Glu Leu Val Arg Pro Gly
                20                  25                  30

Thr Ser Val Lys Met Ser Cys Lys Ala Ala Gly Tyr Thr Phe Thr Asn
            35                  40                  45

Tyr Trp Ile Gly Trp Val Lys Gln Arg Pro Gly His Gly Leu Glu Trp
        50                  55                  60

Ile Gly Asp Ile Tyr Pro Glu Asn Asp Phe Ser Asn Tyr Asn Glu Lys
65                  70                  75                  80

Phe Lys Asp Lys Ala Thr Leu Thr Ala Asp Thr Ser Ser Arg Thr Ala
                85                  90                  95

Tyr Met Gln Leu Ser Ser Leu Thr Ser Glu Asp Ser Ala Ile Tyr Tyr
            100                 105                 110

Cys Val Arg Ala Asn Glu Gly Trp Tyr Leu Asp Val Trp Gly Thr Gly
        115                 120                 125

Thr Thr Val Ser Val Ser Ser Ala Lys Thr Thr Pro Pro Ser Val Tyr
130                 135                 140
```

Pro Leu Ala Pro Gly Cys Gly Asp Thr Thr Gly Ser Ser Val Thr Leu
145                 150                 155                 160

Gly Cys Leu Val Lys Gly Tyr Phe Pro Glu Ser Val Thr Val Thr Trp
                165                 170                 175

Asn Ser Gly Ser Leu Ser Ser Ser Val His Thr Phe Pro Ala Leu Leu
            180                 185                 190

Gln Ser Gly Leu Tyr Thr Met Ser Ser Ser Val Thr Val Pro Ser Ser
        195                 200                 205

Thr Trp Pro Ser Gln Thr Val Thr Cys Ser Val Ala His Pro Ala Ser
210                 215                 220

Ser Thr Thr Val Asp Lys Lys Leu Glu Pro Ser Gly Pro Thr Ser Thr
225                 230                 235                 240

Ile Asn Pro Cys Pro Pro Cys Lys Glu Cys His Lys Cys Pro Ala Pro
                245                 250                 255

Asn Leu Glu Gly Gly Pro Ser Val Phe Ile Phe Pro Pro Asn Ile Lys
            260                 265                 270

Asp Val Leu Met Ile Ser Leu Thr Pro Lys Val Thr Cys Val Val Val
        275                 280                 285

Asp Val Ser Glu Asp Asp Pro Asp Val Gln Ile Ser Trp Phe Val Asn
290                 295                 300

Asn Val Glu Val Leu Thr Ala Gln Thr Gln Thr His Arg Glu Asp Tyr
305                 310                 315                 320

Asn Ser Thr Ile Arg Val Val Ser Ala Leu Pro Ile Gln His Gln Asp
                325                 330                 335

Trp Met Ser Gly Lys Glu Phe Lys Cys Lys Val Asn Asn Lys Asp Leu
            340                 345                 350

Pro Ala Pro Ile Glu Arg Thr Ile Ser Lys Ile Lys Gly Ile Val Arg
        355                 360                 365

Ala Pro Gln Val Tyr Ile Leu Ser Pro Pro Glu Gln Leu Ser Arg
370                 375                 380

Lys Asp Val Ser Leu Thr Cys Leu Ala Val Gly Phe Ser Pro Glu Asp
385                 390                 395                 400

Ile Ser Val Glu Trp Thr Ser Asn Gly His Thr Glu Glu Asn Tyr Lys
                405                 410                 415

Asn Thr Ala Pro Val Leu Asp Ser Asp Gly Ser Tyr Phe Ile Tyr Ser
            420                 425                 430

Lys Leu Asp Ile Lys Thr Ser Lys Trp Glu Lys Thr Asp Ser Phe Ser
        435                 440                 445

Cys Asn Val Arg His Glu Gly Leu His Ser Tyr Tyr Leu Lys Lys Thr
450                 455                 460

Ile Ser Arg Ser Pro Gly Lys
465                 470

<210> SEQ ID NO 7
<211> LENGTH: 464
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 7

Met Gly Trp Ser Leu Ile Leu Leu Phe Leu Val Ala Val Ala Thr Arg
1               5                   10                  15

Val His Ser Gln Val Gln Leu Val Gln Ser Gly Ser Glu Leu Lys Lys

-continued

```
                20                  25                  30
Pro Gly Ala Ser Val Lys Met Ser Cys Lys Ala Gly Tyr Thr Phe
            35                  40                  45
Thr Asn Tyr Trp Ile Gly Trp Val Arg Gln Ala Pro Gly Gln Gly Leu
        50                  55                  60
Glu Trp Ile Gly Asp Ile Tyr Pro Glu Asn Asp Phe Ser Asn Tyr Asn
65                  70                  75                  80
Glu Lys Phe Lys Asp Arg Ala Thr Leu Thr Ala Asp Thr Ser Thr Arg
                85                  90                  95
Thr Ala Tyr Met Glu Leu Ser Ser Leu Arg Ser Glu Asp Thr Ala Val
            100                 105                 110
Tyr Tyr Cys Val Arg Ala Asn Glu Gly Trp Tyr Leu Asp Val Trp Gly
        115                 120                 125
Gln Gly Thr Thr Val Thr Val Ser Ser Ala Ser Thr Lys Gly Pro Ser
    130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Lys Thr Tyr Thr Cys Asn Val Asp His
    210                 215                 220
Lys Pro Ser Asn Thr Lys Val Asp Lys Arg Val Glu Ser Lys Tyr Gly
225                 230                 235                 240
Pro Pro Cys Pro Ser Cys Pro Ala Pro Glu Phe Leu Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser Gln Glu Asp Pro
        275                 280                 285
Glu Val Gln Phe Asn Trp Tyr Val Asp Gly Val Glu Val His Asn Ala
    290                 295                 300
Lys Thr Lys Pro Arg Glu Glu Gln Phe Asn Ser Thr Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Gly Leu Pro Ser Ser Ile Glu Lys Thr
            340                 345                 350
Ile Ser Lys Ala Lys Gly Gln Pro Arg Glu Pro Gln Val Tyr Thr Leu
        355                 360                 365
Pro Pro Ser Gln Glu Glu Met Thr Lys Asn Gln Val Ser Leu Thr Cys
    370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Arg Leu Thr Val Asp Lys Ser
            420                 425                 430
Arg Trp Gln Glu Gly Asn Val Phe Ser Cys Ser Val Met His Glu Ala
        435                 440                 445
```

Leu His Asn His Tyr Thr Gln Lys Ser Leu Ser Leu Ser Leu Gly Lys
        450                 455                 460

<210> SEQ ID NO 8
<211> LENGTH: 464
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 8

Met Gly Trp Ser Leu Ile Leu Leu Phe Leu Val Ala Val Ala Thr Arg
1               5                   10                  15

Val His Ser Gln Val Gln Leu Val Gln Ser Gly Ser Glu Leu Lys Lys
            20                  25                  30

Pro Gly Ala Ser Val Lys Val Ser Cys Lys Ala Ala Gly Tyr Thr Phe
        35                  40                  45

Thr Asn Tyr Trp Ile Gly Trp Val Arg Gln Ala Pro Gly Gln Gly Leu
    50                  55                  60

Glu Trp Ile Gly Asp Ile Tyr Pro Glu Asn Asp Phe Ser Asn Tyr Asn
65                  70                  75                  80

Glu Lys Phe Lys Asp Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Val Arg Ala Asn Glu Gly Trp Tyr Leu Asp Val Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Ser Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr

```
                340             345             350
Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
            450                 455                 460

<210> SEQ ID NO 9
<211> LENGTH: 234
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 9

Met Arg Val Pro Ala Gln Leu Leu Gly Leu Leu Leu Leu Trp Leu Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Tyr Leu Ala Trp Tyr Gln Gln Lys Pro Gly Lys Ala Pro
    50                  55                  60

Lys Leu Leu Val Tyr Phe Ala Lys Thr Leu Ala Glu Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Asn Tyr Tyr Cys Gln His His Tyr
            100                 105                 110

Gly Thr Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

-continued

```
<210> SEQ ID NO 10
<211> LENGTH: 234
<212> TYPE: PRT
<213> ORGANISM: Artificial Sequence
<220> FEATURE:
<221> NAME/KEY:
<223> OTHER INFORMATION: synthetic polypeptide

<400> SEQUENCE: 10

Met Arg Val Pro Ala Gln Leu Leu Gly Leu Leu Leu Leu Trp Leu Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Glu Asn
        35                  40                  45

Ile Tyr Ser Tyr Leu Ala Trp Tyr Gln Gln Lys Pro Gly Lys Ala Pro
    50                  55                  60

Lys Leu Leu Val Tyr Phe Ala Lys Thr Leu Ala Glu Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln His His Tyr
            100                 105                 110

Gly Thr Pro Tyr Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 6
<212> TYPE: PRT
<213> ORGANISM: Artificial Sequence
<220> FEATURE:
<221> NAME/KEY:
<223> OTHER INFORMATION: synthetic 6xHis tag

<400> SEQUENCE: 11

His His His His His His
1               5

<210> SEQ ID NO 12
<211> LENGTH: 4
<212> TYPE: PRT
<213> ORGANISM: Artificial Sequence
<220> FEATURE:
<221> NAME/KEY:
<223> OTHER INFORMATION: synthetic peptide
```

```
<400> SEQUENCE: 12

Lys Asp Glu Leu
1
```